US009447083B2

(12) United States Patent
Choi et al.

(10) Patent No.: US 9,447,083 B2
(45) Date of Patent: Sep. 20, 2016

(54) N-ACYLHYDRAZONE DERIVATIVES FOR SELECTIVE T CELL INHIBITOR AND ANTI-LYMPHOID MALIGNANCY DRUG

(71) Applicants: CHONG KUN DANG PHARMACEUTICAL CORP., Seoul (KR); INJE UNIVERSITY INDUSTRY-ACADEMIC COOPERATION FOUNDATION, Gimhae-si (KR)

(72) Inventors: HoJin Choi, Yongin-si (KR); JaeWon Lee, Yongin-si (KR); ChangGon Lee, Yongin-si (KR); NiNa Ha, Yongin-si (KR); Su Kil Seo, Busan (KR); SunMi Lee, Busan (KR); Song-Min Lee, Sangju-si (KR)

(73) Assignees: CHONG KUN DANG PHARMACEUTICAL CORP. (KR); INJE UNIVERSITY INDUSTRY-ACADEMIC COOPERATION FOUNDATION (KR)

( * ) Notice: Subject to any disclaimer, the term of this patent is extended or adjusted under 35 U.S.C. 154(b) by 0 days.

(21) Appl. No.: 14/424,749

(22) PCT Filed: Aug. 29, 2013

(86) PCT No.: PCT/KR2013/007751
§ 371 (c)(1),
(2) Date: Feb. 27, 2015

(87) PCT Pub. No.: WO2014/035149
PCT Pub. Date: Mar. 6, 2014

(65) Prior Publication Data
US 2015/0252030 A1 Sep. 10, 2015

(30) Foreign Application Priority Data

Aug. 30, 2012 (KR) .................. 10-2012-0095729
Sep. 28, 2012 (KR) .................. 10-2012-0108972

(51) Int. Cl.
| | |
|---|---|
| C07D 409/12 | (2006.01) |
| C07D 209/08 | (2006.01) |
| C07D 409/14 | (2006.01) |
| C07D 403/12 | (2006.01) |
| C07D 401/14 | (2006.01) |
| C07D 235/08 | (2006.01) |
| C07D 401/12 | (2006.01) |
| C07D 405/12 | (2006.01) |
| C07D 285/14 | (2006.01) |

(52) U.S. Cl.
CPC ........... *C07D 409/14* (2013.01); *C07D 209/08* (2013.01); *C07D 235/08* (2013.01); *C07D 285/14* (2013.01); *C07D 401/12* (2013.01); *C07D 401/14* (2013.01); *C07D 403/12* (2013.01); *C07D 405/12* (2013.01); *C07D 409/12* (2013.01)

(58) Field of Classification Search
CPC ........................... C07D 409/12; C07D 209/08
See application file for complete search history.

(56) References Cited

U.S. PATENT DOCUMENTS

2009/0163545 A1  6/2009  Goldfarb

FOREIGN PATENT DOCUMENTS

| DE | 102004037515 A1 | 3/2005 |
| WO | 2006121684 A2 | 11/2006 |
| WO | 2008121877 A2 | 10/2008 |
| WO | 2009155362 A1 | 12/2009 |
| WO | 2013-032907 | 3/2013 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Kieseier et al; "A critical appraisal of treatment decisions in multiple sclerosis—old versus new," O. Nat. Rev. Neurol., May 2011, pp. 255-262, vol. 7.
Socie et al; "Acute graft-versus-host disease: from the bench to the bedside," Blood, Nov. 12, 2009, vol. 114, No. 20, pp. 4327-4336.
Miller et al; "Chemotherapy Alone Compared with Chemotherapy Plus Radiotherapy for Localized Intermediate- and High-Grade Non-Hodgkin's Lymphoma," The New England Journal of Medicine, Jul. 2, 1998, vol. 339, No. 1, pp. 21-26.
Bashir et al; "Current Immunotherapy in Multiple Sclerosis," Immunology and Cell Biology, 1998, vol. 76, pp. 55-64.
McNally et al; "Eliminating Encephalitogenic T Cells Without Undermining Protective Immunity," The Journal of Immunology, 2014, vol. 192, pp. 73-83.
Ferrara et al; "Graft-versus-host disease," thelancet.com, May 2, 2009, vol. 373, pp. 1550-1561.
Welniak et al; "Immunobiology of Allogeneic Hematopoietic Stem Cell Transplantation," Annu. Rev. Immunol., 2007, vol. 25, pp. 139-170.

(Continued)

*Primary Examiner* — Shawquia Jackson
(74) *Attorney, Agent, or Firm* — Heslin, Rothenberg, Farley & Mesiti P.C.

(57) ABSTRACT

The present invention relates to novel N-acylhydrazone derivatives, and more particularly to novel N-acylhydrazone derivatives having selective T cell inhibitory activity and/or anti-lymphoid malignancy activity, stereoisomers thereof, pharmaceutically acceptable salts thereof, the use thereof for preparing pharmaceutical compositions, pharmaceutical compositions containing the same, treatment methods using the compositions, and methods for preparing the novel N-acylhydrazone derivatives.

8 Claims, 5 Drawing Sheets

(56) References Cited

OTHER PUBLICATIONS

He et al; "Inhibition of histone methylation arrests ongoing graft-versus-host disease in mice by selectively inducing apoptosis of alloreactive effector T cells," Blood, Feb. 2, 2012, vol. 119, No. 5, pp. 1274-1282.

Webster et al; "Neuroendocrine Regulation of Immunity," Annu. Rev. Immunol., 2002, vol. 12, pp. 125-163.

Parekh et al; "New molecular targets in mantle cell lymphoma," Seminars in Cancer Biology, 2011, vol. 21, pp. 335-346.

Murphy et al; "New strategies for preventing graft-versus-host disease," Current Opinion in Immunology, 1999, vol. 11, pp. 509-515.

Lopez-Diego et al; "Novel therapeutic strategies for multiple sclerosis—a multifaceted adversary," Nature Reviews Drug Discovery, Nov. 2008, vol. 7, pp. 909-925.

William M. Carroll; "Oral Therapy for Multiple Sclerosis—Sea Change or Incremental Step?," New England Journal of Medicine, Feb. 4, 2010, vol. 362, No. 5, pp. 456-458.

LV et al; "The Antiepileptic Drug Valproic Acid Restores T Cell Homeostasis and Ameliorates Pathogenesis of Experimental Autoimmune Encephalomyelitis," The Journal of Biological Chemistry, Aug. 17, 2012, vol. 287, No. 34, pp. 28656-28665.

Dasmahapatra et al; "The Bruton tyrosine kinase (BTK) inhibitor PCI-32765 synergistically increases proteasome inhibitor activity in diffuse large-B cell lymphoma (DLBCL) and mantle cell lymphoma (MCL) cells sensitive or resistant to bortezomib," British Journal of Haematology, 2013, vol. 161, pp. 43-56.

Pui et al; "Treatment of Acute Lymphoblastic Leukemia," The New England Journal of Medicine, Jan. 12, 2006, vol. 354, No. 2, pp. 166-178.

Luznik et al; "Durable engraftment of major histocompatibility complex-incompatible cells after nonmyeloablative conditioning with fludarabine, low-dose total body irradiation, and post-transplantation cyclophosphamide," Blood, Dec. 1, 2001, vol. 98, No. 12, pp. 3456-3464.

International Search Report for PCT/KR2013/007751 dated Nov. 29, 2013.

Germain, et al; "Identification of a selective small molecule inhibitor of breast cancer stem cells," Bioorganic & Medicinal Chemistry Letters, May 2012, vol. 22, pp. 3571-3574.

Database CAPLUS, Caesar Access No. 1724, referencing Misra, et al., Synthesis of 2-Substituted Phenyl-3-Aryloxyacetyl Hydrazono Methylenyl-Indoles as Central Nervous System Active Agents, Document No. 96:142622, Accession No. 1982:142622.

Database CAPLUS, Caesar Access No. 1720, Kobrakov, et al., Synthesis and Spectral Characteristics of Hydrazones and N-Acylhydrazones, Containing Dichloropyridyl Fragments, Document No. 145:45892, Accession No. 2005:1039430.

Lack, et al., Journal of Medicinal Chemistry, "Targeting the Binding Function 3 (BF3) Site of the Human Androgen Receptor through Virtual Screening," 2011, vol. 54, pp. 8563-8573.

Kobrakov, ct al., Synthesis and Spectral Characteristics of Hydrazones and N-Acylhydrazones Containing Dichloropyridyl Units, A.N. Kosygin Moscow State Textile University, 2005, vol. 48, No. 5, pp. 6-11, Moscow, Russia. (English Translation).

\* cited by examiner

N-ACYLHYDRAZONE DERIVATIVES FOR SELECTIVE T CELL INHIBITOR AND ANTI-LYMPHOID MALIGNANCY DRUG

CROSS-REFERENCE TO RELATED APPLICATION

This application is the National Phase filing under 35 U.S.C. §371 of PCT International Application No. PCT/KR2013/007751 filed Aug. 29, 2013, and published under PCT Article 21(2) in English as WO 2014/035149 A1 on Mar. 6, 2014, which claims priority to Korean Application No. 10-2012-0095729, filed Aug. 30, 2012, and Korean Application No. 10-2012-0108972 filed on Sep. 28, 2012. The contents of each of the prior applications are incorporated by reference herein in their entirety.

TECHNICAL FIELD

The present invention relates to novel N-acylhydrazone derivatives, and more particularly to novel N-acylhydrazone derivatives having selective T cell inhibitory activity and/or anti-lymphoid malignancy activity, stereoisomers thereof, pharmaceutically acceptable salts thereof, the use thereof for preparing pharmaceutical compositions, pharmaceutical compositions containing the same, treatment methods using the compositions, and methods for preparing the novel N-acylhydrazone derivatives.

BACKGROUND ART

Immunosuppressant Drugs

The key issue of the transplantation field is to suppress the immune responses leading to graft rejection. Thus, the development of immunosuppressive drugs capable of selectively and effectively regulating immune responses specific to grafts is a key issue to increase the success rate of transplantation. T cells are the major target to prevent the transplant rejection, and most immunosuppressive drugs clinically used inhibit the T cell responses.

Azathioprine is the first immunosuppressant used in organ transplantation. However, azathioprine inhibits DNA synthesis, resulting in side effects such as leukopenia, bone marrow suppression and macrocytosis, and thus was converted to a second-line therapy after the introduction of cyclosporine. Cyclosporine and tacrolimus, which are calcineurin inhibitors, are currently being used as first-line therapy in organ transplantation.

The two drugs block the expression of interleukin-2 (IL-2) by inhibitoin of calcineurin. Further, these drugs can suppress the T cell activation in the initial stage, and thus strongly suppress the immune responses leading to graft rejection. However, these drugs are required to be administered over a long period and cause side effects, including nephrotoxicity, anemia and hypertension, as well as infectious diseases and tumors caused by a weakening in the immune system. In recent years, in order to reduce the side effects of the calcineurin inhibitors, mycophenolate mofetil that is an inhibitor of nucleotide synthesis has been administered in combination with the calcineurin inhibitor, but has shown side effects such as digestive disease, leukopenia and anemia.

Sirolimus and everolimus, which are inhibitors of mTOR (mammalian target of rapamycin), are drugs that inhibit the proliferation of T cells by blockade of IL-2 receptor signaling. These drugs are mainly administered in combination with the calcineurin inhibitor, because the efficacy is mild when these are administered alone. However, these drugs increase the side effects of the calcineurin inhibitor, such as hyperlipidemia and thrombocytopenia.

FTY720, an antagonist of sphingosine-1-phosphate, is a drug that reduces immune responses by blocking the T cell migration from lymphoid organs to grafts, and has an advantage of low toxicity compared to other drugs. However, FTY720 can cause heart attack when it is administered with other drugs (e.g., general anesthetics and beta-blockers). In the organ transplantation field, combination therapy with cyclosporine is in clinical trials (see N Engl J Med. 351, 2715-2729; N Engl J Med. 352, 1371-1373; Nat Med. 11, 605-613; Business Insights. 2010, BI100022-067).

As described above, the current immunosuppressants for preventing transplant rejection are toxic and cause many side effects such as the occurrence of infection and tumors by weakening the immune system. Thus, the development of new drugs capable of selectively depleting T cells that respond to transplantation antigens is required.

Graft-Versus-Host Disease

Allogeneic haematopoietic stem cell transplantation (HSCT) is the most effective and permanent treatment method for various malignant blood diseases and immune deficiency diseases and is being used for treatment of about 20,000 or more patients annually worldwide (as reported by the Center for International Blood and Marrow Transplant Research). In recent years, the application of the HSCT to autoimmune diseases, solid cancers and the organ transplantation field has been attempted. Despite the rapid development of allogeneic haematopoietic stem cell transplantation (e.g., the development of HLA identification technology and new immunosuppressants) during the past 20 years, graft-versus-host disease (GVHD) that is a complication caused by donor T cells still remains as the major cause of post transplantation mortality. Acute GVHD (grades II-IV) that occurs mainly before 100 days after transplantation appears in 25-60% of the patients in the case of HLA matching between blood relations and 45-70% of the patients in the case of non-blood relation, and 70% or more of patients with the disease (grades III-IV) die. Acute GVHD develops in three stages. In the first stage, proinflammatory factors (TNF-α and LPS) produced by high-dose chemotherapy and systemic radiotherapy before transplantation, activate the dendritic cells of peripheral lymphoid organs. In the second stage, alloantigen-specific T cells proliferate by activated dendritic cells and differentiate into effector cells. In the final stage, the alloantigen-specific effector T cells migrate the gut, the liver and the skin, which are major target organs, and cause inflammatory injury to tissues.

The response rate of the calcineurin inhibitor that is a first-line therapy for preventing acute GVHD is about less than 50%, and thus the prevention rate is very low compared to that of organ transplantation. Treatment after GVHD development depends on steroid therapy, but the steroid therapy shows a response rate of less than 50%, and thus is classified as high-risk therapy having high therapy-related mortality (see Annu Rev Immunol. 25, 139-170; Blood. 114, 4327-4336; Lancet. 373, 1550-1561, Curr Opin Immunol. 11, 509-515). Thus, the development of new effective drugs for the prevention and treatment of acute GVHD is urgently required.

Multiple Sclerosis

Multiple sclerosis is an inflammatory disease of the central nervous system (CNS), which is an autoimmune disease caused by T cells reacting to the myelin-derived antigen. It shows a relapse-remitting pattern in the initial stage of development, and then progresses into secondary progressive multiple sclerosis due to the progressive accumulation of brain and spinal cord lesions. The accumulation of brain and spinal cord lesions leads to visual loss, movement and balance disorders, language and sensory disorders, paraplegia, sexual function impairment, and disturbances of urination and evacuation, and when the accumulation is severe, it causes systemic paralysis.

Therapies for treating multiple sclerosis are largely divided into management of acute exacerbations, disease-modifying therapy, symptomatic therapy, and preventive therapy. The management of acute exacerbations are performed to weaken inflammation and provide immunosuppressant effects, and the disease-modifying therapy is performed to retard the progression of the disease so as to prevent the disease from developing into progressive multiple sclerosis.

In the management of acute exacerbations, a high dose (500-1000 mg/kg) of glucocorticoid is administered intravenously for 3-5 days in order to alleviate the symptoms and prevent permanent injury. Glucocorticoid functions to inhibit the migration of immune cells into the brain or reduce edema, thereby inhibiting inflammation that occurred in the acute stage (see Immunology and Cell Biology. 76, 55-64; Annu. Rev. Immunol. 20, 125-163). Although glucocorticoid exhibits an excellent effect in the acute stage, it cannot prevent the progression of the disease in the disease-modifying therapy.

In the disease-modifying therapy, immunotherapy is performed in order to treat the disease and prevent the recurrence of the disease. Drugs approved by the US FDA for immunotherapy include interferon-beta (IFN-β), glatiramer acetate (GA), mitoxantrone and natalizumab. However, they show the following side effect (see N Engl J Med. 362, 456-458):

IFN-β, a drug that is currently most popularly used, has anti-inflammatory and antiviral effects and acts to inhibit the expression of antigens and prevent the activation of T cells. In addition, IFN-β activates co-stimulatory molecules to induce the apoptosis of self-reactive cells. However, IFN-β can be administered only by an intramuscular or subcutaneous route, and thus when it is administered for a long period of time, it causes erythema and edema at the injected site and involves side effects, including muscular pain, chills and autoimmune disease.

Mitoxantrone (novatrone) has very low molecular weight, and thus passes through the meninges to inhibit the proliferation of T cells, B cells and macrophages in the meninges and the antigen presenting function of antigen presenting cells (APCs), thereby alleviating the symptom of multiple sclerosis. However, mitoxantrone has a defect in that the dose should be limited, because it places a heavy burden on the heart.

Glatiramer acetate (GA) is an analogue of myelin basic protein (MBP). GA forms a GA/MHC complex when MBP binds to a HLA class II molecule, and thus it inhibits the activation of MBP-reactive T cells by competition with MBP when it binds to T cell receptor (TCR). GA has the effects of reducing the number of relapses of relapsing-remitting multiple sclerosis and alleviating the symptom of multiple sclerosis upon the relapse of multiple sclerosis, like IFN-β, but shows an increase frequency of development of permanent black holes in the central nervous system compared to IFN-β.

Natalizumab is a humanized monoclonal antibody that binds directly to the α4 subunit (CD49; adhesion molecule on the surface of leukocytes) of integrin VLA 4 (very late antigen 4) to prevent the binding between leukocytes and vascular endothelial cells, thereby preventing active T cells from entering the central nervous system. It shows excellent effects on relapsing-remitting multiple sclerosis, but causes a side effect of progressive multifocal leukoencephalopathy (PML) in 0.3-0.9% of the patients after 2 years of administration.

Fingolimod is a synthetic analogue of S1P (sphingosine 1-phosphate) receptor for myriocin and is the first orally administered drug recently approved by the US FDA.

Fingolimod acts to prevent activated lymphocytes from moving from secondary lymphoid tissues to the central nervous system by binding of S1PR to the surface of activated type 1 helper T cells. However, the drugs in developing were reported to have side effects, including infection, macular edema, headache, influenza, diarrhea, lumbago and an increase in liver enzyme (see Nat. Rev. Neurol. 7, 255-262; Nat Rev Drug Discov. 11, 909-925).

Thus, there is a need for the development of new drugs that can block the progression to secondary progressive multiple sclerosis while showing high therapeutic effects by short-term oral administration (see N Engl J Med. 362, 456-458).

Lymphoid Malignancy

As used herein, the term "lymphoid malignancy" refers to a tumor of lymphoid cells (B cells, T cells and NK/T cells) in bone marrow and lymphoid tissue. Lymphoid malignancy is largely classified into leukemia, lymphoma and multiple myeloma. Lymphoid leukemia is a blood tumor in which immature lymphocytes in bone marrow change to cancer cells that are accumulated in tissue and spread systemically through blood. Lymphoid leukemia is largely classified into acute lymphoid leukemia and chronic lymphoid leukemia. Lymphoma is a blood tumor in which lymphocytes in lymphoid tissue change to cancer cells that are accumulated in the tissue and spread to peripheral blood and bone marrow. It is classified into Hodgkin's lymphoma and non-Hodgkin's lymphoma. Multiple myeloma is a blood tumor in which plasma cells in peripheral lymphoid tissue change to cancer cells that are then accumulated in bone marrow (see J Clin Invest. 2012; 122:3396-3397; Blood. 1994; 84:1361-1392; Lancet. 2012; 380:848-857).

Treatment of lymphoid malignancy is performed by standard chemotherapy using a combination of cyclophosphamide, doxorubicin, vincristine and prednisone. With respect to the initial response effects of the drugs, the remission rate of adult patients is as high as about 85%, but the recurrence rate is high, and thus the 5-year disease-free survival is only 30-40%.

In addition, the drugs show a high risk of infection due to their high cytotoxicity and frequently cause side effects, including neurotoxicity, digestive problems and bleeding (see N Engl J Med. 1998; 339:21-26; N Engl J Med 2006; 354:166-78; Nat Rev Drug Discov. 2007; 6:149-165).

Recently, it has been reported that drugs having cytotoxic effects on specific cells also have anti-tumor effects when the same cells change to cancer cells. The B cell immunosuppressant ibrutinib that inhibits Bruton's tyrosine kinase (BTK), a signaling mediator of B cell receptor (BCR), was reported to have an anticancer effect against relapsing or drug-refractory B cell lymphoma. Bortezomib that is an inhibitor of NF-κB activity is used as an immunosuppressant for inhibiting memory T cells and B cells. Bortezomib was approved by the US FDA as a therapeutic agent for treating multiple sclerosis and has also recently been used in combination with ibrutinib for B cell lymphoma. Suberoylanilide hydroxamic acid (SAHA) that is histone deacetylase inhibitor (HDACi) is known to have an anticancer effect against cutaneous T cell lymphoma. Since the inhibitory effect of SAHA against graft-versus-host disease (GVHD) was recently found in animal models, SAHA has received new attention as an immunosuppressant (see Semin Cancer Biol. 2011 November; 21:335-46; Br J Haematol. 2013; 161:43-56; N Engl J Med. 2008; 359:906-917; Nat Rev Drug Discov. 2006; 5:769-784; J. Clin. Invest. 2008; 118: 2562-2573). Thus, an immunosuppressive drug that targets specific immune cells can be clinically used as a new anticancer agent capable of specifically targeting a specific tumor.

DISCLOSURE

Technical Problem

It is an object of the present invention to provide novel compounds can selectively and effectively remove transplantation antigen- and autoantigen-specific T cells, and thus can be used as agents for the prevention and treatment of transplantation immune rejection and/or the treatment of autoimmune diseases. In addition, it is an object of the present invention to provide novel compounds have excellent apoptotic effects against lymphoid malignancy cells, and thus can be used as agents for treating lymphoid malignancy.

Therefore, it is an object of the present invention to provide novel N-acylhydrazone derivatives having selective T cell inhibitory activity and/or anti-lymphoid malignancy activity, stereoisomers thereof, pharmaceutically acceptable salts thereof, pharmaceutical compositions containing the same, treatment methods using the compositions, and methods for preparing the novel N-acylhydrazone derivatives.

Technical Solution

The present invention relates to a compound of the following formula 1, a stereoisomer thereof, or a pharmaceutically acceptable salt thereof:

[Formula 1]

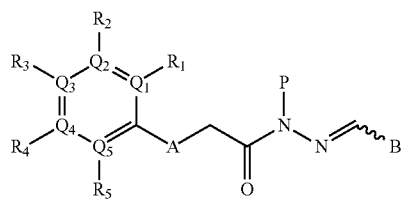

wherein

A is N—H, O, or S;

$Q_1, Q_2, Q_3, Q_4$ and $Q_5$ are each independently C or N;

$R_1, R_2, R_3, R_4$ and $R_5$ are each independently absent, —H, —$CF_3$, —F, —Br, —Cl, cyanide, —$CH_2OH$, —(CO)$NH_2$, —($C_1$-$C_6$)alkyl, —($C_{1-3}$)alkoxy, —$NH_2$, —N($CH_3$)$_2$, or 4, 5 or 6-membered heteroaryl or heterocycloalkyl comprising 1 to 3 members selected from the group consisting of N, O and S (said heteroaryl or heterocycloalkyl has at least one substituent selected from —H, halogen and amine);

P is —H, —($C_1$-$C_3$)OH, —($C_1$-$C_6$)alkyl, —(CO)($C_1$-$C_6$) alkyl;

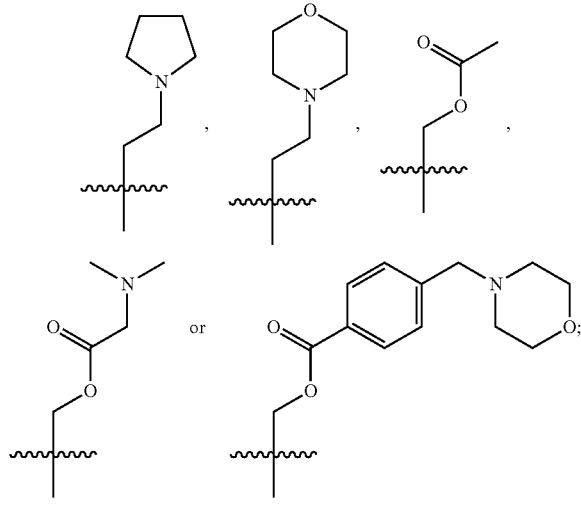

and

B is selected from the group consisting of:

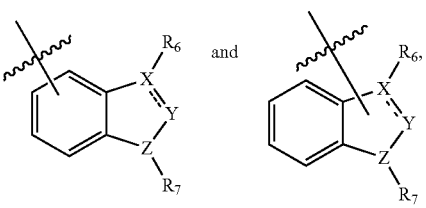

wherein, X, Y and Z are each independently C, N or S, and $R_6$ and $R_7$ are each independently absent, —H, —Br, —($C_1$-$C_6$)alkyl, —($C_1$-$C_3$)OH,

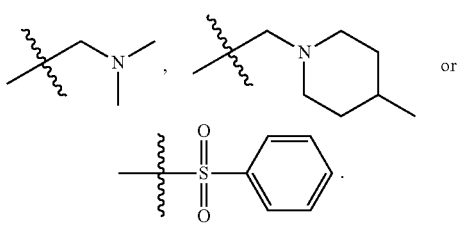

In one aspect of the present invention, the compounds of formula 1 are further defined by the followings:

A is N—H, O or S;

$Q_1, Q_2, Q_3, Q_4$ and $Q_5$ are C;

$R_2$ and $R_4$ are H;

$R_1, R_3$ and $R_5$ are each independently —H, —F, —Br, —Cl, methyl, ethyl, —$CH_2OH$, cyanide, —$NH_2$, or 4, 5 or 6-membered heteroaryl or heterocycloalkyl comprising 1 to 3 members selected from the group consisting of N, O and S;

P is —H, methyl, —$CH_2OH$, —$CH_2CH_2OH$,

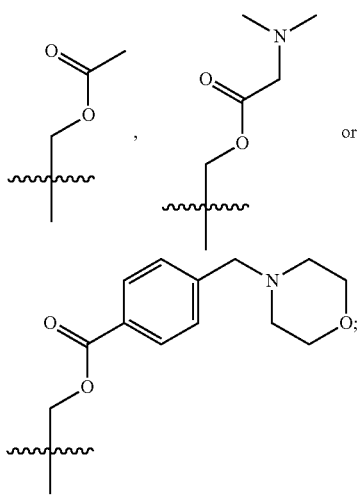

and

B is selected from the group consisting of:

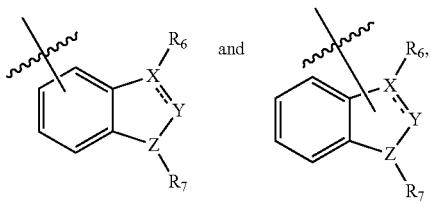

wherein X and Y is C,

Z is N, and

R$_6$ and R$_7$ are each independently —H, methyl or —CH$_2$CH$_2$OH.

The compound of formula 1 according to the present invention may be used generally as a form of pharmaceutically acceptable salt thereof. The pharmaceutically acceptable salts thereof include pharmaceutically acceptable base addition salts or acid addition salts, for example, metal salts, such as alkali and alkaline earth metal salts, ammonium salt, organic amine addition salt, amino acid addition salt and sulfonate salt. Acid addition salts include inorganic acid addition salts, such as hydrogen chloride salt, sulfonic acid salt and phosphoric acid salt; and organic acid addition salts, such as alkyl sulfonate, aryl sulfonate, acetate, malate, fumarate, tartrate, citrate and lactate. Examples of metal salts include alkali metal salt, such as lithium salt, sodium salt and potassium salt; alkaline earth metal salts, such as magnesium salt, calcium salt, aluminium salt and zinc salt. Examples of ammonium salt include ammonium salt and tetramethylammonium salt. Examples of organic amine addition salts include salts with morpholine and piperidine. Examples of amino acid addition salts include salts with glycine, phenylalanine, glutamic acid and lysine. Examples of sulfonate salt include mesylate, tosylate and benzenesulfonic acid salts.

The term of "stereoisomer" means the isomer molecules that have the same molecular formula and bonds, but differ by their three-dimensional orientation.

Specific examples of preferred compounds of formula 1 according to the present invention include:

Compound 065
(E)-N'-((1H-indol-4-yl)methylene)-2-(mesityloxy)acetohydrazide;
Compound 092
(E)-N'-((1H-indol-5-yl)methylene)-2-(4-bromo-2,6-dimethylphenoxy)acetohydrazide;
Compound 108
(E)-N'-((1H-indol-6-yl)methylene)-2-(mesityloxy)acetohydrazide;
Compound 109
(E)-N'-((1H-indol-2-yl)methylene)-2-(mesityloxy)acetohydrazide;
Compound 112
(E)-N'-((1H-indol-4-yl)methylene)-2-(4-bromo-2,6-dimethylphenoxy)acetohydrazide;
Compound 133
(E)-N'-((1H-indol-6-yl)methylene)-2-(4-bromo-2,6-dimethylphenoxy)acetohydrazide;
Compound 135
(E)-N'-((1H-indol-4-yl)methylene)-2-(mesitylamino)acetohydrazide;
Compound 137
(E)-N'-((1H-indol-4-yl)methylene)-2-(2,6-dimethyl-4-(pyridin-3-yl)phenoxy)acetohydrazide;
Compound 139
(E)-N'-((1H-indol-6-yl)methylene)-2-(2,6-dimethyl-4-(pyridin-3-yl)phenoxy)acetohydrazide;
Compound 146
(E)-N'-((1H-indol-4-yl)methylene)-2-(2-(pyridin-3-yl)phenoxy)acetohydrazide;
Compound 147
(E)-N'-((1H-indol-4-yl)methylene)-2-(mesitylthio)acetohydrazide;
Compound 149
(E)-N'-((1H-indol-4-yl)methylene)-2-(2,6-dimethyl-4-(pyrimidin-5-yl)phenoxy)acetohydrazide;
Compound 155
(E)-N'-((1H-indol-4-yl)methylene)-2-(4-chloro-2,6-dimethylphenoxy)acetohydrazide;
Compound 156
(E)-N'-((1H-indol-3-yl)methylene)-2-(4-chloro-2,6-dimethylphenoxy)acetohydrazide;
Compound 157
(E)-N'-((1H-indol-6-yl)methylene)-2-(4-chloro-2,6-dimethylphenoxy)acetohydrazide;
Compound 158
(E)-N'-((1H-indol-3-yl)methylene)-2-(mesitylthio)acetohydrazide;
Compound 159
(E)-N'-((1H-indol-6-yl)methylene)-2-(mesitylthio)acetohydrazide;
Compound 164
(E)-2-(mesityloxy)-N-methyl-N'-((1-methyl-1H-indol-4-yl)methylene)acetohydrazide;
Compound 177
(E)-N'-((1H-indol-4-yl)methylene)-N-(2-hydroxyethyl)-2-(mesityloxy)acetohydrazide;
Compound 180
(E)-N'-((1-(2-hydroxyethyl)-1H-indol-4-yl)methylene)-2-(mesityloxy)acetohydrazide;
Compound 182
(E)-N'-((1H-indol-4-yl)methylene)-2-(2,4-dimethyl-6-(pyridin-3-yl)phenoxy)acetohydrazide;
Compound 183
(E)-N'-((1H-indol-6-yl)methylene)-2-(2,4-dimethyl-6-(pyridin-3-yl)phenoxy)acetohydrazide;

Compound 184
(E)-N'-((1H-indol-5-yl)methylene)-2-(2,4-dimethyl-6-(pyridin-3-yl)phenoxy)acetohydrazide;
Compound 187
(E)-N'-((1H-indol-4-yl)methylene)-2-((2-methylpyridin-3-yl)oxy)acetohydrazide;
Compound 195
(E)-N'-((1H-indol-6-yl)methylene)-N-(2-hydroxyethyl)-2-(mesityloxy)acetohydrazide;
Compound 217
(E)-N'-((1H-indol-6-yl)methylene)-2-(2,4-dimethyl-6-(pyridin-4-yl)phenoxy)acetohydrazide;
Compound 218
(E)-N'-((1H-indol-6-yl)methylene)-2-(2-(furan-3-yl)-4,6-dimethylphenoxy)acetohydrazide;
Compound 227
(E)-N'-((1H-indol-4-yl)methylene)-2-(4-(hydroxymethyl)-2,6-dimethylphenoxy)acetohydrazide;
Compound 228
(E)-N'-((1H-indol-6-yl)methylene)-2-(4-(hydroxymethyl)-2,6-dimethylphenoxy)acetohydrazide;
Compound 229
(E)-N'-((1H-indol-6-yl)methylene)-2-(2,4-dimethyl-6-(tetrahydrofuran-3-yl)phenoxy)acetohydrazide;
Compound 232
(E)-N'-((1H-indol-4-yl)methylene)-2-(4-amino-2,6-dimethylphenoxy)acetohydrazide;
Compound 233
(E)-N'-((1H-indol-6-yl)methylene)-N-(hydroxymethyl)-2-(mesityloxy)acetohydrazide;
Compound 236
(E)-(2-((1H-indol-6-yl)methylene)-1-(2-(mesityloxy)acetyl)hydrazinyl)methyl 2-(dimethylamino)acetate;
Compound 237
(E)-N'-((1H-indol-6-yl)methylene)-2-(4-cyano-2,6-dimethylphenoxy)acetohydrazide;
Compound 238
(E)-(2-((1H-indol-4-yl)methylene)-1-(2-(mesityloxy)acetyl)hydrazinyl)methyl 2-(dimethylamino)acetate;
Compound 243
(E)-N'-((1H-indol-6-yl)methylene)-N-acetyl-2-(mesityloxy)acetohydrazide;
Compound 244
(E)-N'-((1H-indol-4-yl)methylene)-N-(hydroxymethyl)-2-(mesityloxy)acetohydrazide;
Compound 245
(E)-(2-((1H-indol-4-yl)methylene)-1-(2-(mesityloxy)acetyl)hydrazinyl)methyl 4-(morpholinomethyl)benzoate;
Compound 252
(E)-(2-((1H-indol-4-yl)methylene)-1-(2-(mesityloxy)acetyl)hydrazinyl)methyl acetate;
Compound 258
(E)-N'-((1H-indol-6-yl)methylene)-2-(2,6-dimethylphenoxy)acetohydrazide;
Compound 259
(E)-N'-((1H-indol-4-yl)methylene)-2-(2-bromo-4,6-dimethylphenoxy)acetohydrazide;
Compound 260
(E)-N'-((1H-indol-6-yl)methylene)-2-(2-bromo-4,6-dimethylphenoxy)acetohydrazide;
Compound 272
(E)-(2-((1H-indol-6-yl)methylene)-1-(2-(mesityloxy)acetyl)hydrazinyl)methyl 4-(morpholinomethyl)benzoate;
Compound 311
(E)-N'-((1H-indol-6-yl)methylene)-2-(2-methyl-6-(tetrahydrofuran-3-yl)phenoxy)acetohydrazide;
Compound 312
(E)-N'-((1H-indol-4-yl)methylene)-2-(2-methyl-6-(tetrahydrofuran-3-yl)phenoxy)acetohydrazide;
Compound 313
(E)-N'-((1H-indol-6-yl)methylene)-2-(2-(furan-3-yl)-6-methylphenoxy)acetohydrazide;
Compound 314
(E)-N'-((1H-indol-4-yl)methylene)-2-(2-(furan-3-yl)-6-methylphenoxy)acetohydrazide;
Compound 317
(E)-N'-((1H-indol-4-yl)methylene)-2-(2-(furan-2-yl)-4,6-dimethylphenoxy)acetohydrazide;
Compound 319
(E)-N'-((1H-indol-4-yl)methylene)-2-((2-(furan-3-yl)pyridin-3-yl)oxy)acetohydrazide;
Compound 320
(E)-N'-((1H-indol-4-yl)methylene)-2-(2,4-dimethyl-6-(tetrahydrofuran-3-yl)phenoxy)acetohydrazide;
Compound 322
(E)-N'-((1H-indol-6-yl)methylene)-2-(4-(furan-3-yl)-2,6-dimethylphenoxy)acetohydrazide;
Compound 323
(E)-N'-((1H-indol-6-yl)methylene)-2-(2,6-dimethyl-4-(tetrahydrofuran-3-yl)phenoxy)acetohydrazide;
Compound 329
(E)-N'-((1H-indol-4-yl)methylene)-2-((2-ethyl-6-methylpyridin-3-yl)oxy)acetohydrazide;
Compound 331
(E)-N'-((1H-indol-6-yl)methylene)-2-((2-(pyrrolidin-1-yl)pyridin-3-yl)oxy)acetohydrazide;
Compound 332
(E)-N'-((1H-indol-6-yl)methylene)-2-(2,4-dimethyl-6-(tetrahydrofuran-2-yl)phenoxy)acetohydrazide;
Compound 333
(E)-N'-((1H-indol-4-yl)methylene)-2-(2-(furan-3-yl)-4,6-dimethylphenoxy)acetohydrazide;
Compound 336
(E)-N'-((1H-indol-4-yl)methylene)-2-(4-(furan-3-yl)-2,6-dimethylphenoxy)acetohydrazide;
Compound 337
(E)-N'-((1H-indol-4-yl)methylene)-2-(2,6-dimethyl-4-(tetrahydrofuran-3-yl)phenoxy)acetohydrazide;
Compound 343
(E)-N'-((1H-indol-6-yl)methylene)-2-((2-(thiophen-3-yl)pyridin-3-yl)oxy)acetohydrazide;
Compound 344
(E)-N'-((1H-indol-4-yl)methylene)-2-(2,4-dimethyl-6-(thiophen-2-yl)phenoxy)acetohydrazide;
Compound 346
(E)-N'-((1H-indol-4-yl)methylene)-2-(2-(furan-2-yl)-4-methoxyphenoxy)acetohydrazide;
Compound 375
(E)-2-(2,4-dimethyl-6-(tetrahydrofuran-3-yl)phenoxy)-N-methyl-N'-((1-methyl-1H-indol-6-yl)methylene)acetohydrazide;
Compound 378
(E)-N'-((1H-indol-6-yl)methylene)-2-(4-fluoro-2-methyl-6-(tetrahydrofuran-3-yl)phenoxy)acetohydrazide;
Compound 379
(E)-N'-((1H-indol-4-yl)methylene)-2-(4-fluoro-2-methyl-6-(tetrahydrofuran-3-yl)phenoxy)acetohydrazide;
Compound 380
(E)-2-(4-fluoro-2-methyl-6-(tetrahydrofuran-3-yl)phenoxy)-N-methyl-N'-((1-methyl-1H-indol-6-yl)methylene)acetohydrazide; and Compound 457
(E)-N'-((1H-indol-6-yl)methylene)-2-(2,4-dimethyl-6-(tetrahydro-2H-pyran-4-yl)phenoxy)acetohydrazide.

Specific examples of more preferred compounds of formula 1 according to the present invention include:
Compound 065
(E)-N'-((1H-indol-4-yl)methylene)-2-(mesityloxy)acetohydrazide;
Compound 108
(E)-N'-((1H-indol-6-yl)methylene)-2-(mesityloxy)acetohydrazide;
Compound 229
(E)-N'-((1H-indol-6-yl)methylene)-2-(2,4-dimethyl-6-(tetrahydrofuran-3-yl)phenoxy)acetohydrazide; and
Compound 457
(E)-N'-((1H-indol-6-yl)methylene)-2-(2,4-dimethyl-6-(tetrahydro-2H-pyran-4-yl)phenoxy)acetohydrazide.

The present invention also provides pharmaceutical compositions comprising the N-acylhydrazone derivative of the formula 1, stereoisomers thereof or a pharmaceutically acceptable salt thereof; and a pharmaceutically acceptable carrier.

Preferably, the composition is used for the prevention or the treatment of a disease associated with the inhibition against T cell activity. Specific examples of the disease include graft-versus-host disease (GVHD) after haematopoietic stem cell transplantation or organ transplantation, multiple sclerosis and rheumatoid arthritis.

Preferably, the composition is used for the treatment of lymphoid malignancy. Specific examples of the lymphoid malignancy include T lymphoid leukemia, B lymphoid leukemia, NK leukemia, NKT leukemia, multiple myeloma, T lymphoma and B lymphoma.

Advantageous Effects

The present invention provides novel compounds having N-acylhydrazone structure, which can be used as a selective T cell inhibitor and/or an anti-lymphoid malignancy drug.

The compounds effectively inhibit the active T cell. That is, the compounds selectively and effectively remove transplantation antigen- and autoantigen-specific T cells, and thus can be used for the prevention and treatment of immune rejection response after transplantation and the treatment of autoimmune diseases. Such examples are graft-versus-host disease (GVHD) after haematopoietic stem cell transplantation or organ transplantation, multiple sclerosis, rheumatoid arthritis etc.

In addition, these compounds have excellent apoptotic effects against lymphoid malignancy cells, and thus can be used as agents for treating lymphoid malignancy. Such examples are T lymphoid leukemia, B lymphoid leukemia, NK leukemia, NKT leukemia, multiple myeloma, T lymphoma, B lymphoma etc.

BEST MODE FOR CARRYING OUT THE INVENTION

Preparation of Compounds

Figure 1:
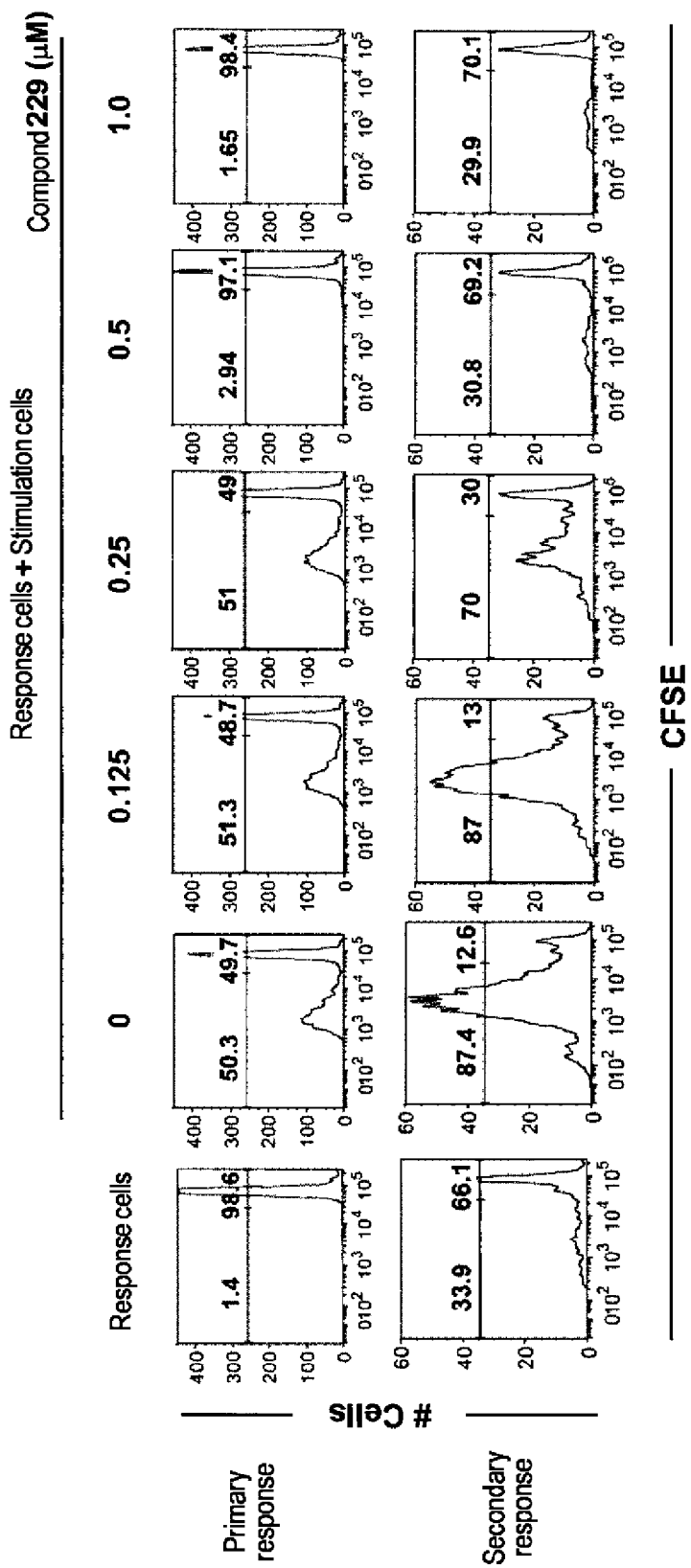
FIGS. 1 and 2 show the results of the inhibition activity test against alloantigen-specific T cells of the compound of the present invention in the condition of cell culture.

The compounds of formula 1 according to the present invention can be prepared by the methods known from various references. The preparation methods of the compounds of formula 1 will be described in further detail with the following reaction schemes and examples.

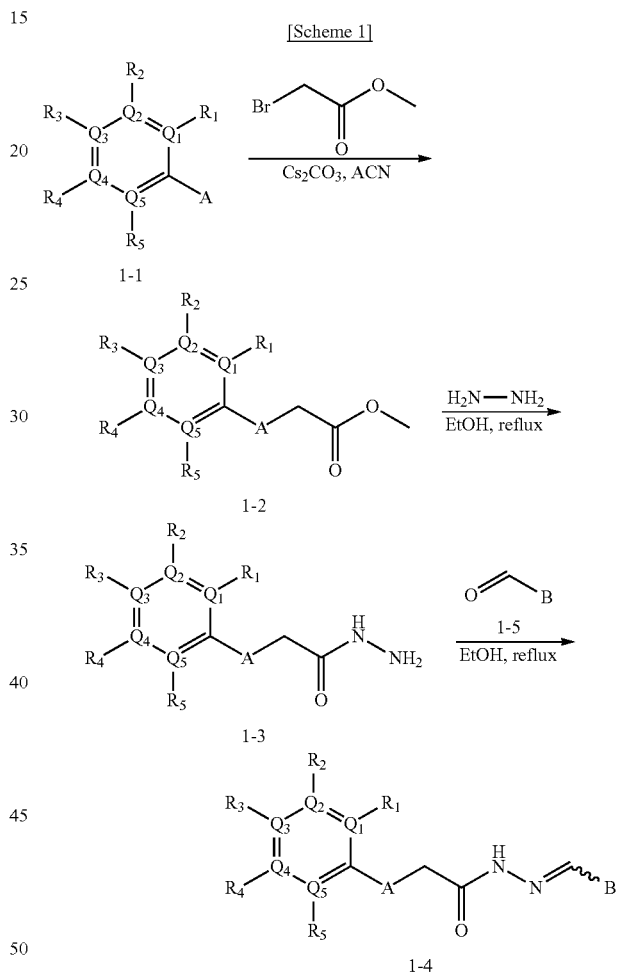

Synthesis of Compound 1-2 (Methyl Bromoacetate Reaction)

Compound 1-1 and methyl bromoacetate are dissolved in acetonitrile, and then added with cesium carbonate, followed by stirring. After the completion of the reaction, the reaction mixture is filtered through Celite to remove cesium carbonate, concentrated under reduced pressure, and purified to obtain compound 1-2.

Synthesis of Compound 1-3 (Hydrazine Reaction)

Compound 1-2 and hydrazine monohydrate are dissolved in ethanol, followed by stirring. After the completion of the reaction, the reaction mixture is concentrated under reduced pressure, and purified to obtain compound 1-3 as white solid.

Synthesis of Compound 1-4 (Aldehyde Reaction)

Compound 1-3 and an aldehyde compound are dissolved in ethanol, followed by stirring. After the completion of the reaction, the reaction mixture is concentrated under reduced pressure to remove ethanol, and then purified to obtain compound 1-4.

By the same method, compounds 013, 014, 034, 065, 083, 092, 100, 108, 109, 112, 118, 121, 127, 133, 135, 136, 137, 138, 139, 146, 147, 149, 152, 155, 156, 157, 158, 159, 180, 182, 183, 184, 187, 190, 191, 192, 193, 194, 196, 205, 206, 211, 217, 218, 227, 228, 229, 237, 256, 258, 259, 260, 279, 280, 286, 288, 291, 293, 301, 302, 303, 304, 310, 311, 312, 313, 314, 317, 318, 319, 320, 322, 323, 326, 327, 329, 330, 331, 332, 333, 336, 337, 343, 344, 345, 346, 347, 356, 358, 359, 378, 379 and 457 can be synthesized.

EXAMPLE 1

Synthesis of Compound 013

Step 1. Synthesis of methyl 2-(o-tosyloxy)acetate: o-Cresol (5 g, 46.24 mmol) was dissolved in dimethylformamide. Methyl bromoacetate (7.1 g, 46.24 mmol) and potassium carbonate (19 g, 138.42 mmol) were added thereto, followed by stirring at room temperature for 1 hour. After the completion of the reaction, the reaction mixture was added with water, and extracted with ethyl acetate. The obtained organic layer was washed with a saturated ammonium chloride aqueous solution, dried over magnesium sulfate, and concentrated under reduced pressure to obtain methyl 2-(0-tosyloxy)acetate, which was used in the next step without any further purification.

Step 2. Synthesis of 2-(o-tosyloxy)acetohydrazide: To methyl 2-(o-tosyloxy)acetate (8.3 g, 46.24 mmol), an excess amount of hydrazine monohydrate was added, followed by stirring at 90° C. for 10 minutes. After the completion of the reaction, water was added thereto, thereby forming a solid, which was filtered and washed with diethyl ether to obtain 2-(o-tosyloxy)acetohydrazide as a white solid.

Step 3. Synthesis of (E)-N'-((1H-indol-4-yl)methylene)-2-(o-tosyloxy)acetohydrazide: 2-(o-tosyloxy)acetohydrazide (0.1 g, 0.55 mmol) and 1H-indol-4-carbaldehyde (0.08 g, 0.55 mmol) were dissolved in ethanol, followed by stirring at 90° C. for 3 hours. After the completion of the reaction, the reaction mixture was cooled to room temperature. Hexane was added thereto. The resulting solid was filtered, and washed with diethyl ether to obtain Compound 013 as a white solid.

$^1$H NMR (400 MHz, DMSO-$d_6$): δ 11.51-11.37 (m, 2H), 8.51-8.25 (m, 0.7H), 7.50-7.46 (m, 2H), 7.23-6.97 (m, 5H), 6.91-6.79 (m, 2H), 5.22-4.68 (m, 1H), 2.26-2.22 (m, 3H).

EXAMPLE 2

Synthesis of Compound 014

2-(o-tosyloxy)acetohydrazide (0.1 g, 0.55 mmol) and 1H-indol-5-carbaldehyde (0.08 g, 0.55 mmol) were dissolved in ethanol, followed by stirring at 90° C. for 3 hours. After the completion of the reaction, the reaction mixture was cooled to room temperature, followed by removing the solvent. Hexane and ethyl acetate were added thereto. The formed solid was filtered, and washed with diethyl ether to obtain Compound 014 as a white solid.

$^1$H NMR (400 MHz, DMSO-$d_6$): δ 11.38-11.28 (m, 2H), 8.33-8.07 (m, 1H), 7.80-7.79 (m, 1H), 7.54-7.52 (m, 1H), 7.44-7.38 (m, 2H), 7.17-7.11 (m, 2H), 6.88-6.83 (m, 2H), 6.49 (m, 1H), 5.15-4.63 (m, 2H), 2.24-2.21 (m, 3H).

EXAMPLE 3

Synthesis of Compound 034

2-(o-tosyloxy)acetohydrazide (0.1 g, 0.55 mmol) and 1H-indol-6-carbaldehyde (0.101 g, 0.67 mmol) were dissolved in EtOH, followed by stirring at 90° C. for 18 hours. After the completion of the reaction, the reaction mixture was cooled to room temperature, and concentrated under reduced pressure. The resulting solid was filtered, and washed with diethyl ether to obtain Compound 034.

$^1$H NMR (400 MHz, DMSO-$d_6$): δ 11.41-11.20 (m, 1.6H), 8.33 (s, 0.3H), 8.06 (m, 0.4H), 7.69-7.41 (m, 4H), 7.18-7.06 (m, 2H), 6.90-6.80 (m, 2H), 6.45 (m, 1H), 5.14-4.63 (m, 2H), 2.23-2.16 (m, 3H).

EXAMPLE 4

Synthesis of Compound 065

Step 1. Synthesis of methyl 2-(mesityloxy)acetate: 2,4,6-trimethylphenol (1 g, 7.3 mmol) was dissolved in dimethylformamide. Methyl bromoacetate (1.1 g, 7.3 mmol) and potassium carbonate (3 g, 22 mmol) were added thereto, followed by stirring at room temperature for 16 hours. After the completion of the reaction, the reaction mixture was added with water, and extracted with ethyl acetate. The obtained organic layer was washed with water 3 times, dried over magnesium sulfate, and concentrated under reduced pressure to obtain 2-(mesityloxy)acetate (1.5 g 100%).

Step 2. Synthesis of 2-(mesityloxy)acetohydrazide: Methyl 2-(mesityloxy)acetate (1.5 g, 7.3 mmol) was dissolved in tetrahydrofuran. Hydrazine monohydrate (5.16 g, 103 mmol) was added thereto, followed by stirring at room temperature for 1 hour. After the completion of the reaction, the reaction mixture was concentrated under reduced pressure. The concentrate was added with water, and filtered. The filtrate was washed with water and diethyl ether to obtain 2-(mesityloxy)acetohydrazide (1.36 g, 89%) as a white solid.

Step 3. Synthesis of (E)-N'-((1H-indol-4-yl)methylene)-2-(mesityloxy)acetohydrazide: 2-(mesityloxy)acetohydrazide (0.1 g, 0.48 mmol) and 1H-indol-4-carbaldehyde (0.08 g, 0.53 mmol) were dissolved in ethanol, followed by stirring at 90° C. for 3 hours. After the completion of the reaction, the reaction mixture was cooled to room temperature. Hexane was added thereto. The resulting solid was filtered, and washed with ethanol to obtain Compound 065 (58 mg, 36%) as a white solid.

$^1$H NMR (400 MHz, DMSO-$d_6$): δ 11.48-11.35 (m, 2H), 8.70 (s, 0.5H), 8.23 (s, 0.5H), 7.50-7.43 (m, 2H), 7.25-7.10 (m, 2.5H), 6.85-6.76 (m, 2.5H), 4.84 (s, 1H), 4.36 (s, 1H), 2.23 (s, 6H), 2.19 (s, 3H).

EXAMPLE 5

Synthesis of Compound 083

Step 1. Synthesis of methyl 2-(o-toluidino)acetate: o-toluidine (1 g, 9.3 mmol) was dissolved in dimethylformamide. Methyl bromoacetate (1.3 g, 9.3 mmol) and potassium carbonate (3.9 g, 28 mmol) were added thereto, followed by stirring at room temperature for 16 hours. After the completion of the reaction, the reaction mixture was added with water, and extracted with ethyl acetate. The obtained organic layer was washed with water 3 times, dried over magnesium sulfate, and concentrated under reduced pressure to obtain methyl 2-(o-toluidino)acetate, which was used in the next step.

Step 2. Synthesis of 2-(o-toluidino)acetohydrazide: Methyl 2-(o-toluidino)acetate (1.7 g, 9.3 mmol) was dissolved in tetrahydrofuran. Hydrazine monohydrate (5.16 g, 103 mmol) was added thereto, followed by stirring at room temperature for 16 hours. After the completion of the reaction, the reaction mixture was concentrated under reduced pressure. The obtained concentrate was purified by column chromatography to obtain 2-(o-toluidino)acetohydrazide (0.3 g, 18%) as a yellow liquid.

Step 3. Synthesis of (E)-N'-((1H-indol-4-yl)methylene)-2-(o-toluidino)acetohydrazide: 2-(o-toluidino)acetohydrazide (0.12 g, 0.67 mmol) and 1H-indol-4-carbaldehyde (0.12 g, 0.803 mmol) were dissolved in ethanol, followed by stirring at 90° C. for 3 hours. After the completion of the reaction, the reaction mixture was cooled to room temperature, and concentrated under reduced pressure. The resulting solid was filtered, and washed with diethyl ether to obtain Compound 083 (58 mg, 5%) of brown color.

$^1$H NMR (400 MHz, DMSO-$d_6$): δ 11.40-11.20 (m, 2.4H), 8.27-8.07 (m, 1H), 7.79-7.37 (m, 5H), 7.00-6.97 (m, 2H), 6.52-6.47 (m, 3H), 4.26 (d, J=5.44 Hz, 1.4H), 3.82-3.80 (d, J=5.88 Hz, 1H), 2.13-2.11 (m, 3H).

EXAMPLE 6

Synthesis of Compound 100

2-(o-tosyloxy)acetohydrazide (0.1 g, 0.56 mmol) and 1H-indol-6-carbaldehyde (0.97 g, 0.67 mmol) were dissolved in ethanol, followed by stirring at 90° C. for 3 hours. After the completion of the reaction, the reaction mixture was cooled to room temperature, and concentrated under reduced pressure. The resulting solid concentrate was purified by column chromatography to obtain Compound 100 (0.04 g, 47%).

$^1$H NMR (400 MHz, DMSO-$d_6$): δ 11.37 (bs, 0.4H), 8.37 (bs, 0.4H), 8.26-8.25 (m, 1H), 8.09 (bs, 0.6H), 7.85 (s, 1H), 7.60 (s, 1H), 7.16-7.08 (m, 2H), 6.88-6.81 (m, 2H), 5.15-4.64 (m, 2H), 2.23-2.20 (m, 3H).

EXAMPLE 7

Synthesis of Compound 108

2-(mesityloxy)acetohydrazide (0.12 g, 0.57 mmol) and 1H-indol-6-carbaldehyde (0.1 g, 0.69 mmol) were dissolved in ethanol, followed by stirring at 90° C. overnight. After the completion of the reaction, the reaction mixture was cooled to room temperature, and concentrated under reduced pressure. The resulting solid concentrate was purified by column chromatography (ethyl acetate:hexane=1:1) and recrystallization (ethyl acetate:hexane=1:1) to obtain Compound 108 (0.03 g, 16%).

$^1$H NMR (400 MHz, DMSO-$d_6$): δ 11.39-11.20 (m, 2H), 8.48 (s, 0.5H), 8.01 (s, 0.3H), 7.68 (s, 0.5H), 7.57-7.24 (m, 3H), 6.83 (s, 2H), 6.45-6.41 (m, 1H), 4.73-4.30 (m, 2H), 2.21-2.14 (m, 9H).

EXAMPLE 8

Synthesis of Compound 109

2-(mesityloxy)acetohydrazide (0.12 g, 0.57 mmol) and 1H-indol-2-carbaldehyde (0.1 g, 0.69 mmol) were dissolved in ethanol, followed by stirring at 90° C. for 16 hours. After the completion of the reaction, the reaction mixture was cooled to room temperature, and concentrated under reduced pressure. The resulting solid concentrate was purified by column chromatography and by recrystallization to obtain Compound 109 (0.07 g, 36%).

$^1$H NMR (400 MHz, DMSO-$d_6$): δ 11.35-11.30 (m, 2H), 8.47 (s, 0.6H), 8.01 (s, 0.4H), 7.78-7.70 (m, 1H), 7.53-7.34 (m, 3H), 6.83 (m, 2H), 6.49-6.49 (m, 1H), 4.72-4.29 (m, 2H), 2.21-2.17 (m, 9H).

EXAMPLE 9

Synthesis of Compound 112

Step 1. Synthesis of methyl 2-(4-bromo-2,6-dimethylphenoxy)acetate: 4-bromo-2,6-dimethylphenol (3.0 g, 14.9 mmol) and methyl bromoacetate (1.55 mL, 16.4 mmol) were dissolved in acetonitrile. Cesium carbonate (14.6 g, 44.8 mmol) was added thereto, followed by stirring at room temperature for 1 day. After the completion of the reaction, the reaction mixture was added with a saturated sodium hydrogen carbonate aqueous solution, and extracted with ethyl acetate. The obtained organic layer was washed with brine, dried over sodium sulfate anhydrous, filtered, and concentrated under reduced pressure to obtain methyl 2-(4-bromo-2,6-dimethylphenoxy)acetate (4.1 g, 100%) without purification.

Step 2. Synthesis of 2-(4-bromo-2,6-dimethylphenoxy) acetohydrazide: Methyl 2-(4-bromo-2,6-dimethylphenoxy) acetate (4.1 g, 14.9 mmol) and hydrazine monohydrate (0.87 mL, 17.9 mmol) were dissolved in ethanol, followed by stirring for 1 day under reflux. After the completion of the reaction, the reaction mixture was concentrated under reduced pressure. The concentrated residue was dried and purified to obtain 2-(4-bromo-2,6-dimethylphenoxy)acetohydrazide (2.5 g, 51%) as a white solid.

Step 3. Synthesis of (E)-N'-((1H-indol-4-yl)methylene)-2-(4-bromo-2,6-dimethylphenoxy)acetohydrazide: 2-(4-bromo-2,6-dimethylphenoxy)acetohydrazide (0.18 g, 0.66 mmol) and indol-4-carboxaldehyde (0.11 g, 0.73 mmol) were dissolved in ethanol, followed by stirring overnight under reflux. After the completion of the reaction, the reaction mixture was concentrated under reduced pressure. The concentrated residue was dried and purified to obtain Compound 112 (52 mg, 20%) as a white solid.

$^1$H NMR (400 MHz, DMSO-$d_6$): δ 11.52, 11.48 (s, 1H), 11.37 (bs, 1H), 8.67, 8.23 (s, 1H), 7.51-7.44 (m, 2H), 7.29-7.24 (m, 2.65H), 7.18-7.12 (m, 2H), 6.77 (s, 0.47H), 4.90, 4.42 (s, 2H), 2.29, 2.28 (m, 6H).

EXAMPLE 10

Synthesis of Compound 118

Step 1. Synthesis of methyl 2-(2,6-dimethylphenoxy) acetate: 2,6-dimethylphenol (3.0 g, 24.6 mmol) and methyl bromoacetate (2.57 mL, 27.0 mmol) were dissolved in acetonitrile. Cesium carbonate (24.0 g, 73.7 mmol) was added thereto, followed by stirring at room temperature for 1 day. After the completion of the reaction, the reaction mixture was added with a saturated sodium hydrogen carbonate aqueous solution, and extracted with ethyl acetate. The obtained organic layer was washed with brine, dried over sodium sulfate anhydrous, filtered, and concentrated under reduced pressure to obtain methyl 2-(2,6-dimethylphenoxy)acetate (4.77 g, 100%) without purification.

Step 2. Synthesis of 2-(2,6-dimethylphenoxy)acetohydrazide: Methyl 2-(2,6-dimethylphenoxy)acetate (4.77 g, 24.6 mmol) and hydrazine monohydrate (1.43 mL, 29.4 mmol) were dissolved in ethanol, followed by stirring for 1 day under reflux. After the completion of the reaction, the reaction mixture was concentrated under reduced pressure. The concentrated residue was dried and purified to obtained 2-(2,6-dimethylphenoxy)acetohydrazide (2.2 g, 46%) as a white solid.

Step 3. Synthesis of (E)-N'-((1H-indol-4-yl)methylene)-2-(2,6-dimethylphenoxy)acetohydrazide: 2-(2,6-dimethylphenoxy)acetohydrazide (100 mg, 0.52 mmol) and indol-4-carboxaldehyde (82.2 mg, 0.57 mmol) were dissolved in ethanol, followed by stirring overnight under reflux. After the completion of the reaction, the reaction mixture was concentrated under reduced pressure. The concentrated residue was dried and purified to obtain Compound 118 (71.6 mg, 43%) as a white solid.

$^1$H NMR (400 MHz, DMSO-$d_6$): δ 11.51, 11.46 (s, 1H), 11.37 (bs, 1H), 8.70, 8.24 (s, 1H), 7.51-7.43 (m, 2H), 7.26-6.78 (m, 6H), 4.89, 4.41 (s, 2H), 2.29, 2.28 (m, 6H).

EXAMPLE 11

Synthesis of Compound 121

Step 1. Synthesis of methyl 2-(2,6-diisopropylphenoxy)acetate: 2,6-diisopropylphenol (10 g, 56.1 mmol) was dissolved in acetonitrile. Methyl bromoacetate (8.5 g, 56.1 mmol) and cesium carbonate (37 g, 112.4 mmol) were added thereto, followed by stirring for 16 hours under reflux. After the completion of the reaction, the reaction mixture was added with water, and extracted with ethyl acetate. The obtained organic layer was washed with water 3 times, dried over magnesium sulfate, and concentrated under reduced pressure to obtain methyl 2-(2,6-diisopropylphenoxy)acetate (14 g, 100%), which was used in the next step.

Step 2. Synthesis of 2-(2,6-diisopropylphenoxy)acetohydrazide: 2-(2,6-diisopropylphenoxy)acetate (14 g, 56.1 mmol) was dissolved in EtOH. Hydrazine monohydrate (2.5 g, 56.1 mmol) was added thereto, followed by stirring at room temperature for 16 hours. After the completion of the reaction, the reaction mixture was concentrated under reduced pressure. The obtained concentrate was purified by column chromatography to obtain 2-(2,6-diisopropylphenoxy)acetohydrazide (8.8 g, 62%).

Step 3. Synthesis of (E)-N'-((1H-indol-4-yl)methylene)-2-(2,6-diisopropylphenoxy)acetohydrazide: 2-(2,6-diisopropylphenoxy)acetohydrazide (0.1 g, 0.399 mmol) and 1H-indol-4-carbaldehyde (0.07 g, 0.479 mmol) were dissolved in ethanol, followed by stirring at 100° C. for 16 hours. After the completion of the reaction, the reaction mixture was concentrated under reduced pressure. The obtained concentrate was purified by column chromatography to obtain Compound 121 (0.03 g, 20%).

$^1$H NMR (400 MHz, DMSO-$d_6$): δ 11.57-11.22 (m, 2H), 8.62-8.20 (m, 1H), 7.36-6.72 (m, 8H), 4.83-4.33 (m, 2H), 1.19-1.16 (m, 16H).

EXAMPLE 12

Synthesis of Compound 127

Step 1. Synthesis of methyl 2-(2,6-di-tert-butyl-4-methylphenoxy)acetate: 2,6-di-tert-butyl-4-methylphenol (10 g, 45.4 mmol) was dissolved in acetonitrile. Methyl bromoacetate (7 g, 45.4 mmol) and cesium carbonate (30 g, 91 mmol) were added thereto, followed by stirring for 16 hours under reflux. After the completion of the reaction, the reaction mixture was added with water, and extracted with ethyl acetate. The obtained organic layer was washed with water 3 times, dried over magnesium sulfate, and concentrated under reduced pressure to obtain methyl 2-(2,6-di-tert-butyl-4-methylphenoxy)acetate (13.3 g, 100%), which was used in the next step.

Step 2. Synthesis of 2-(2,6-di-tert-butyl-4-methylphenoxy)acetohydrazide: methyl 2-(2,6-di-tert-butyl-4-methylphenoxy)acetate (13.3 g, 45.4 mmol) was dissolved in EtOH. Hydrazine monohydrate (2.3 g, 45.4 mmol) was added thereto, followed by stirring at room temperature for 16 hours. After the completion of the reaction, the reaction mixture was concentrated under reduced pressure. The obtained concentrate was purified by column chromatography to obtain 2-(2,6-di-tert-butyl-4-methylphenoxy)acetohydrazide (6 g, 45%).

Step 3. Synthesis of (E)-N'-((1H-indol-4-yl)methylene)-2-(2,6-di-tert-butyl-4-methylphenoxy)acetohydrazide: 2-(2,6-di-tert-butyl-4-methylphenoxy)acetohydrazide (0.1 g, 0.342 mmol) and 1H-indol-4-carbaldehyde (0.07 g, 0.41 mmol) were dissolved in ethanol, followed by stirring at 100° C. for 16 hours. After the completion of the reaction, the formed solid was filtered, and washed with acetonitrile to obtain Compound 127 (0.025 g, 18%).

$^1$H NMR (400 MHz, DMSO-$d_6$): δ 8.52-8.22 (s, 1H), 7.78 (m, 1.6H), 7.41 (m, 0.8H), 7.14 (m, 3.2H), 6.92 (m, 0.7H), 4.77 (s, 1.3H), 4.23 (s, 0.5H), 2.33 (d, J=4.56 Hz, 3H), 1.38 (s, 18H).

EXAMPLE 13

Synthesis of Compound 133

2-(4-bromo-2,6-dimethylphenoxy)acetohydrazide (0.1 g, 0.37 mmol) and 1H-indol-6-carbaldehyde (0.11 g, 0.74 mmol) were dissolved in ethanol, followed by stirring for 12 hours under reflux. After the completion of the reaction, the reaction mixture was concentrated under reduced pressure, thereby forming a crystalline solid, which was filtered, washed with ethanol, and purified by column chromatography to obtain Compound 133.

$^1$H NMR (400 MHz, DMSO-$d_6$): δ 11.42 (d, J=9.72 Hz, 1H), 11.33-11.22 (s, 1H), 8.47 (s, 0.5H), 8.03 (s, 0.5H), 7.70 (s, 0.5H), 7.59-7.37 (m, 3H), 7.29 (m, 2.5H), 6.45 (m, 1H), 4.80 (s, 1H), 4.37 (s, 1H), 2.32 (d, J=5.36 Hz, 6H).

EXAMPLE 14

Synthesis of Compound 135

Step 1. Synthesis of methyl 2-(mesitylamino)acetate: 2,4,6-trimethylbenzenamide (10 g, 74 mmol) was dissolved in acetonitrile. Methyl bromoacetate (11.3 g, 74 mmol) and cesium carbonate (48 g, 148 mmol) were added thereto, followed by stirring for 16 hours under reflux. After the completion of the reaction, the reaction mixture was added with water, and extracted with ethyl acetate. The obtained organic layer was washed with water 3 times, dried over magnesium sulfate, and concentrated under reduced pressure to obtain methyl 2-(mesitylamino)acetate (15.3 g, 100%), which was used in the next step.

Step 2. Synthesis of 2-(mesitylamino)acetohydrazide: Methyl 2-(mesitylamino)acetate (15.3 g, 74 mmol) was dissolved in EtOH. Hydrazine monohydrate (3.7 g, 74 mmol) was added thereto, followed by stirring at 100° C. for 16 hours under reflux. After the completion of the reaction, the reaction mixture was concentrated under reduced pressure. The obtained solid compound was filtered to yield 2-(mesitylamino)acetohydrazide (3.9 g, 25%).

Step 3. Synthesis of (E)-N'-((1H-indol-4-yl)methylene)-2-(mesitylamino)acetohydrazide: 2-(mesitylamino)acetohydrazide (0.1 g, 0.48 mmol) and 1H-indol-4-carbaldehyde (0.084 g, 0.58 mmol) were dissolved in ethanol, followed by stirring at 100° C. for 16 hours. After the completion of the reaction, the reaction mixture was concentrated under reduced pressure. The obtained concentrate was purified by column chromatography, and then concentrated under reduced pressure. The formed crystalline solid was filtered to obtain Compound 135 (0.089 g, 55%).

$^1$H NMR (400 MHz, DMSO-$d_6$): δ 11.47-11.34 (m, 2H), 8.41-8.20 (m, 1H), 7.47 (m, 2H), 7.48-7.10 (m, 2H), 6.91 (s, 0.6H), 6.74 (m, 2H), 4.36-3.60 (m, 3H), 2.25-2.12 (m, 9H).

EXAMPLE 15

Synthesis of Compound 136

2-(mesitylamino)acetohydrazide (0.1 g, 0.48 mmol) and 1H-indol-3-carbaldehyde (0.084 g, 0.58 mmol) were dissolved in ethanol, followed by stirring at 100° C. for 16 hours. After the completion of the reaction, the reaction mixture was concentrated under reduced pressure. The obtained concentrate was purified by column chromatography, and then concentrated under reduced pressure. The formed crystalline solid was filtered to obtain Compound 136 (0.06 g, 37%).

$^1$H NMR (400 MHz, DMSO-$d_6$): δ 11.53 (bs, 1H), 11.25-11.06 (m, 1H), 8.33-8.03 (m, 2H), 7.70 (m, 1H), 7.40 (m, 1H), 7.21-7.05 (m, 2H), 6.74-6.71 (m, 2H), 4.36-4.01 (m, 3H), 2.25-2.12 (m, 9H).

EXAMPLE 16

Synthesis of Compound 137

Step 1. Synthesis of 2-(2,6-dimethyl-4-(pyridin-2-yl)phenoxy)acetohydrazide: 2-(4-bromo-2,6-dimethylphenoxy)acetohydrazide (0.5 g, 1.8 mmol) was dissolved in dimethoxyethane/water (2:1) and dimethylformamide. Pyridin-2-ylboronic acid (0.27 g, 2.2 mmol) and Pd(dppf)Cl$_2$ (0.074 g, 0.055 mmol), sodium carbonate (0.58 g, 5.5 mmol) were added thereto, followed by reacting in microwave reactor at 120° C. for 15 minutes. After the completion of the reaction, the reaction mixture was added with water, and extracted with dichloromethane. The obtained organic layer was dried over magnesium sulfate, and concentrated under reduced pressure. The concentrate was purified by column chromatography to obtain 2-(2,6-dimethyl-4-(pyridin-2-yl)phenoxy)acetohydrazide (0.34 g, 69%).

Step 2. Synthesis of (E)-N'-((1H-indol-4-yl)methylene)-2-(2,6-dimethyl-4-(pyridin-2-yl)phenoxy)acetohydrazide: 2-(2,6-dimethyl-4-(pyridin-2-yl)phenoxy)acetohydrazide (0.1 g, 0.37 mmol) and 1H-indol-4-carbaldehyde (0.11 g, 0.74 mmol) were dissolved in ethanol, followed by stirring at 100° C. for 12 hours. After the completion of the reaction, the formed solid compound was filtered to obtain Compound 137 (0.09 g, 61%).

$^1$H NMR (400 MHz, DMSO-$d_6$): δ 11.54-11.35 (m, 2H), 8.84 (s, 1H), 8.68 (s, 0.5H), 8.5 (m, 1H), 8.23 (s, 0.5H), 8.02 (m, 1H), 7.49-6.78 (m, 7H), 4.93 (s, 1H), 4.38 (s, 1H), 2.35 (d, J=3.08 Hz, 6H).

EXAMPLE 17

Synthesis of Compound 138

2-(2,6-dimethyl-4-(pyridin-2-yl)phenoxy)acetohydrazide (0.1 g, 0.37 mmol) and 1H-indol-3-carbaldehyde (0.11 g, 0.74 mmol) were dissolved in ethanol, followed by stirring at 100° C. for 12 hours. After the completion of the reaction, the formed solid compound was filtered to obtain Compound 138 (0.08 g, 46%).

$^1$H NMR (400 MHz, DMSO-$d_6$): δ 11.57-11.22 (m, 2H), 8.84-7.00 (m, 12H), 4.91 (s, 1H), 4.40 (s, 1H), 2.36 (m, 6H).

EXAMPLE 18

Synthesis of Compound 139

2-(2,6-dimethyl-4-(pyridin-2-yl)phenoxy)acetohydrazide (0.1 g, 0.37 mmol) and 1H-indol-6-carbaldehyde (0.11 g, 0.74 mmol) were dissolved in ethanol, followed by stirring at 100° C. for 12 hours. After the completion of the reaction, the reaction mixture was concentrated under reduced pressure. The obtained concentrate was purified by column chromatography to obtain Compound 139 (0.1 g, 52%).

$^1$H NMR (400 MHz, DMSO-$d_6$): δ 11.45-11.22 (m, 2H), 8.84-7.23 (m, 11H), 6.45 (m, 1H), 4.88 (s, 0.8H), 4.11 (s, 1H), 2.31 (d, J=5.76 Hz, 6H).

EXAMPLE 19

Synthesis of Compound 146

Step 1. Synthesis of methyl 2-(2-(pyridin-3-yl)phenoxy)acetate: 2-(pyridin-3-yl)phenol (Compound 6-6) (0.25 g, 1.4 mmol) was dissolved in acetonitrile. Methyl bromoacetate (0.15 g, 1.4 mL) and potassium carbonate (0.6 g, 0.4 mmol) were added thereto, followed by stirring at 16 hours. After the completion of the reaction, the reaction mixture was filtered through Celite, and concentrated under reduced pressure to obtained methyl 2-(2-(pyridin-3-yl)phenoxy)acetate (0.35 g, 100%), which was used in the next step.

Step 2. Synthesis of 2-(2-(pyridin-3-yl)phenoxy)acetohydrazide: methyl 2-(2-(pyridin-3-yl)phenoxy)acetate (0.32 g, 1.3 mmol) was dissolved in EtOH. Hydrazine monohydrate (0.078 g, 1.56 mmol) was added thereto, followed by stirring for 16 hours under reflux. After the completion of the reaction, the reaction mixture was concentrated under reduced pressure. The obtained concentrate was purified by column chromatography to obtain 2-(2-(pyridin-3-yl)phenoxy)acetohydrazide (0.1 g, 31%).

Step 3. Synthesis of (E)-N'-((1H-indol-4-yl)methylene)-2-(2-(pyridin-3-yl)phenoxy)acetohydrazide: 2-(2-(pyridin-3-yl)phenoxy)acetohydrazide (0.1 g, 0.41 mmol) and 1H-indol-4-carbaldehyde (0.072 g, 0.49 mmol) were dissolved in ethanol, followed by stirring at 100° C. for 16 hours. After the completion of the reaction, the reaction mixture was concentrated under reduced pressure. The obtained concentrate was purified by column chromatography, and then concentrated under reduced pressure. The formed crystalline solid was filtered to obtain Compound 146 (0.030 g, 20%).

$^1$H NMR (400 MHz, DMSO-$d_6$): δ 11.54-11.33 (bs, 2H), 8.83 (m, 1H), 8.53-8.49 (m, 1H), 8.42 (s, 0.3H), 8.25 (s, 0.7H), 8.07-8.03 (m, 1H), 7.49-7.32 (m, 6H), 7.23-6.94 (m, 5H), 5.27-4.74 (m, 2H).

EXAMPLE 20

Synthesis of Compound 147

Step 1. Synthesis of methyl 2-(mesitylthio)acetate: 2,4,6-trimethylbenzenethiol (1.5 g, 10 mmol) was dissolved in acetonitrile. Methyl bromoacetate (1.7 g, 11 mmol) and potassium carbonate (3 g, 2.2 mmol) were added thereto, followed by stirring for 16 hours. After the completion of the reaction, the reaction mixture was filtered through Celite. The filtrate was added with a saturated ammonium chloride aqueous solution, and extracted with ethyl acetate. The obtained organic layer was dried over magnesium sulfate, and concentrated under reduced pressure to obtain methyl 2-(mesitylthio)acetate, which was used in the next step.

Step 2. Synthesis of 2-(mesitylthio)acetohydrazide: Methyl 2-(mesitylthio)acetate (2.5 g, 11 mmol) was dissolved in EtOH. Hydrazine monohydrate (0.56 g, 11 mmol) was added thereto, followed by stirring at 100° C. for 16 hours under reflux. After the completion of the reaction, the reaction mixture was concentrated under reduced pressure. The obtained concentrate was added with a saturated ammonium chloride aqueous solution, and extracted with ethyl acetate. The obtained organic layer was dried over magnesium sulfate, concentrated under reduced pressure, and purified by column chromatography to obtain 2-(mesitylthio)acetohydrazide (1 g, 41%).

Step 3. Synthesis of (E)-N'-((1H-indol-4-yl)methylene)-2-(mesitylthio)acetohydrazide: 2-(mesitylthio)acetohydrazide (0.1 g, 0.45 mmol) and 1H-indol-4-carbaldehyde (0.078 g, 0.54 mmol) were dissolved in ethanol, followed by stirring at 100° C. for 16 hours. After the completion of the reaction, the reaction mixture was concentrated under reduced pressure. The obtained concentrate was purified by column chromatography, and then concentrated under reduced pressure. The formed crystalline solid was filtered to obtain Compound 147 (0.028 g, 6.3%).

$^1$H NMR (400 MHz, DMSO-d$_6$): δ 11.32-11.27 (m, 2H), 8.30-8.17 (m, 1H), 7.47 (m, 2H), 7.47-6.88 (m, 5H), 3.72-3.33 (m, 2H), 2.44-1.96 (m, 9H).

EXAMPLE 21

Synthesis of Compound 149

Step 1. Synthesis of methyl 2-(2,6-dimethyl-4-(pyrimidin-5-yl)phenoxy)acetate: 2,6-dimethyl-4-(pyrimidin-5-yl)phenol (Compound 6-3) (0.32 g, 1.6 mmol) was dissolved in acetonitrile. Methyl bromoacetate (0.24 g, 1.6 mmol) and cesium carbonate (1 g, 3.2 mmol) were added thereto, followed by stirring for 12 hours under reflux. After the completion of the reaction, the reaction mixture was filtered through Celite. The filtrate was added with water, and extracted with ethyl acetate. The obtained organic layer was dried over magnesium sulfate, and concentrated under reduced pressure. The concentrate was purified by column chromatography to obtain methyl 2-(2,6-dimethyl-4-(pyrimidin-5-yl)phenoxy)acetate (0.44 g, 100%).

Step 2. Synthesis of 2-(2,6-dimethyl-4-(pyrimidin-5-yl)phenoxy)acetohydrazide: 2-(2,6-dimethyl-4-(pyrimidin-5-yl)phenoxy)acetate (0.44 g, 1.6 mmol) was dissolved in EtOH. Hydrazine monohydrate (0.12 g, 2.4 mmol) was added thereto, followed by stirring at 100° C. for 12 hours under reflux. After the completion of the reaction, the reaction mixture was concentrated under reduced pressure, and purified by column chromatography to obtain 2-(2,6-dimethyl-4-(pyrimidin-5-yl)phenoxy)acetohydrazide (0.085 g, 19%).

Step 3. Synthesis of (E)-N'-((1H-indol-4-yl)methylene)-2-(2,6-dimethyl-4-(pyrimidin-5-yl)phenoxy)acetohydrazide: 2-(2,6-dimethyl-4-(pyrimidin-5-yl)phenoxy) acetohydrazide (0.085 g, 0.31 mmol) and 1H-indol-4-carbaldehyde (0.068 g, 0.47 mmol) were dissolved in ethanol, followed by stirring at 100° C. for 12 hours. After the completion of the reaction, the formed solid compound was filtered to obtain Compound 149 (0.06 g, 70%).

$^1$H NMR (400 MHz, DMSO-d$_6$): δ 11.55 (bs, 1H), 11.35 (bs, 1H), 9.11 (m, 3.2H), 8.7 (s, 0.5H), 8.24 (s, 0.5H), 7.55-6.8 (m, 7H), 4.95 (s, 1H), 4.47 (s, 1H), 2.38 (d, J=3.2 Hz, 6H).

EXAMPLE 22

Synthesis of Compound 152

Step 1. Synthesis of methyl 2-(4-(2-aminopyrimidin-5-yl)-2,6-dimethylphenoxy)acetate: 4-(2-aminopyrimidin-5-yl)-2,6-dimethylphenol (Compound 6-4) (0.27 g, 1.24 mmol) was dissolved in acetonitrile. Methyl bromoacetate (0.12 g, 1.24 mmol) and cesium carbonate (0.81 g, 2.3 mmol) were added thereto, followed by stirring for 12 hours under reflux. After the completion of the reaction, the reaction mixture was filtered through Celite. The filtrate was added with water, and extracted with dichloromethane. The obtained organic layer was dried over magnesium sulfate, concentrated under reduced pressure, and purified by column chromatography to obtain methyl 2-(4-(2-aminopyrimidin-5-yl)-2,6-dimethylphenoxy)acetate (0.28 g, 70%).

Step 2. Synthesis of 2-(4-(2-aminopyrimidin-5-yl)-2,6-dimethylphenoxy)acetohydrazide: methyl 2-(4-(2-aminopyrimidin-5-yl)-2,6-dimethylphenoxy)acetate (0.28 g, 1 mmol) was dissolved in EtOH. Hydrazine monohydrate (0.06 g, 1.2 mmol) was added thereto, followed by stirring at 100° C. for 8 hours under reflux. After the completion of the reaction, the reaction mixture was concentrated under reduced pressure. The formed solid was filtered to obtained 2-(2,6-dimethyl-4-(pyrimidin-5-yl)phenoxy)acetohydrazide (0.31 g, 100%).

Step 3. Synthesis of (E)-N'-((1H-indol-6-yl)methylene)-2-(4-(2-aminopyrimidin-5-yl)-2,6-dimethylphenoxy)acetohydrazide: 2-(2,6-dimethyl-4-(pyrimidin-5-yl)phenoxy)acetohydrazide (0.080 g, 0.28 mmol) and 1H-indol-4-carbaldehyde (0.061 g, 0.41 mmol) were dissolved in ethanol, followed by stirring at 100° C. for 12 hours. After the completion of the reaction, the formed solid was filtered, and purified by column chromatography to obtain Compound 152.

$^1$H NMR (400 MHz, DMSO-d$_6$): δ 9.14-7.01 (m, 10H), 4.93 (s, 1H), 4.42 (s, 1H), 2.37 (d, J=7.96 Hz, 6H).

EXAMPLE 23

Synthesis of Compound 155

Step 1. Synthesis of methyl 2-(4-chloro-2,6-dimethylphenoxy)acetate: 4-chloro-2,6-dimethylphenol (0.5 g, 3.2 mmol) was dissolved in acetonitrile. Methyl bromoacetate (0.49 g, 3.2 mmol) and cesium carbonate (1.8 g, 6.4 mmol) were added thereto, followed by stirring for 16 hours. After the completion of the reaction, the reaction mixture was filtered through Celite. The filtrate was added with water, and extracted with dichloromethane. The obtained organic layer was dried over magnesium sulfate, and concentrated under reduced pressure to obtain methyl 2-(4-chloro-2,6-dimethylphenoxy)acetate (0.4 g, 55%), which was used in the next step.

Step 2. Synthesis of 2-(4-chloro-2,6-dimethylphenoxy) acetohydrazide: methyl 2-(4-chloro-2,6-dimethylphenoxy) acetate (0.5 g, 2.2 mmol) was dissolved in EtOH. Hydrazine monohydrate (0.13 g, 2.6 mmol) was added thereto, followed by stirring for 12 hours under reflux. After the completion of the reaction, the reaction mixture was concentrated under reduced pressure. The concentrate was added with water, and extracted with dichloromethane. The obtained organic layer was dried over magnesium sulfate, and concentrated under reduced pressure to obtain 2-(4-chloro-2,6-dimethylphenoxy)acetohydrazide (0.22 g, 44%).

Step 3. Synthesis of (E)-N'-((1H-indol-4-yl)methylene)-2-(4-chloro-2,6-dimethylphenoxy)acetohydrazide: 2-(4-chloro-2,6-dimethylphenoxy)acetohydrazide (0.08 g, 0.35 mmol) and 1H-indol-4-carbaldehyde (0.076 g, 0.53 mmol) were dissolved in ethanol, followed by stirring for 12 hours under reflux. After the completion of the reaction, the formed solid was filtered to obtain Compound 155 (0.063 g, 51%).

$^1$H NMR (400 MHz, DMSO-$d_6$): δ 11.48-11.33 (m, 1.5H), 8.64 (s, 0.3H), 8.21 (s, 0.4H), 7.44 (m, 2H), 7.24-6.75 (m, 5H), 4.87 (s, 1H), 4.39 (s, 1H), 2.25 (d, J=3.48 Hz, 6H).

EXAMPLE 24

Synthesis of Compound 156

2-(4-chloro-2,6-dimethylphenoxy)acetohydrazide (0.08 g, 0.35 mmol) and 1H-indol-4-carbaldehyde (0.076 g, 0.53 mmol) were dissolved in ethanol, followed by stirring for 12 hours under reflux. After the completion of the reaction, the formed solid was filtered, and purified by column chromatography to obtain Compound 156 (0.03 g, 24%).

$^1$H NMR (400 MHz, DMSO-$d_6$): δ 11.20 (bs, 1H), 11.1 (bs, 1H), 8.54 (s, 0.5H), 8.21 (d, J=7.16 Hz, 5H), 8.14 (s, 0.5H), 7.85 (m, 0.5H), 7.75 (m, 1H), 7.40 (m, 1H), 7.20-7.01 (m, 4H), 4.84 (s, 1H), 4.34 (s, 1H), 2.2 (d, J=3.48 Hz, 6H).

EXAMPLE 25

Synthesis of Compound 157

2-(4-chloro-2,6-dimethylphenoxy)acetohydrazide (0.08 g, 0.35 mmol) and 1H-indol-6-carbaldehyde (0.076 g, 0.53 mmol) were dissolved in ethanol, followed by stirring for 12 hours under reflux. After the completion of the reaction, the formed solid was filtered to obtain Compound 157 (0.043 g, 34%).

$^1$H NMR (400 MHz, DMSO-$d_6$): δ 11.40-11.2 (m, 1.5H), 8.45 (s, 0.5H), 8.02 (s, 0.4H), 7.69-7.26 (m, 4H), 7.11 (d, J=5.72 Hz, 2H), 6.46 (m, 1H), 4.79 (s, 0.8H), 4.36 (s, 1H), 2.25 (d, J=4.92 Hz, 6H).

EXAMPLE 26

Synthesis of Compound 158

2-(mesitylthio)acetohydrazide (0.2 g, 0.89 mmol) and 1H-indol-3-carbaldehyde (0.155 g, 1.1 mmol) were dissolved in ethanol, followed by stirring at 100° C. for 16 hours. After the completion of the reaction, the reaction mixture was concentrated under reduced pressure. The formed crystalline solid was filtered to obtain Compound 158 (0.035 g, 11%).

$^1$H NMR (400 MHz, DMSO-$d_6$): δ 11.52 (bs, 1H), 11.04-11.00 (m, 1H), 8.25-7.96 (m, 2H), 7.75-7.71 (m, 1H), 7.40 (m, 1H), 7.18-6.88 (m, 4H), 3.70 (s, 1.4H), 2.45-2.13 (m, 9H).

EXAMPLE 27

Synthesis of Compound 159

2-(mesitylthio)acetohydrazide (0.2 g, 0.89 mmol) and 1H-indol-6-carbaldehyde (0.16 g, 1.1 mmol) were dissolved in ethanol, followed by stirring at 100° C. for 16 hours. After the completion of the reaction, the reaction mixture was concentrated under reduced pressure. The concentrate was purified by column chromatography, and then concentrated under reduced pressure. The formed crystalline solid was filtered to obtain Compound 159 (0.023 g, 7.3%).

$^1$H NMR (400 MHz, DMSO-$d_6$): δ 11.22 (bs, 2H), 8.13-7.94 (m, 1H), 7.65-7.18 (m, 4H), 6.93-6.86 (m, 2H), 6.43 (m, 1H), 3.68-3.30 (m, 2H), 2.49-2.08 (m, 9H).

EXAMPLE 28

Synthesis of Compound 180

2-(mesitylamino)acetohydrazide (0.03 g, 0.14 mmol) and 1-(2-hydroxyethyl)-1H-indol-4-carbaldehyde (0.03 g, 0.16 mmol) were dissolved in dimethylsulfoxide and acetic acid, followed by stirring at room temperature for 12 hours. After the completion of the reaction, the reaction mixture was added with water, and extracted with diethyl ether. The obtained organic layer was washed with sodium sulfate, and concentrated under reduced pressure. The concentrate was recrystallized to obtain Compound 180 (0.002 g, 3.3%).

$^1$H NMR (400 MHz, DMSO-$d_6$): δ 11.44 (d, J=25 Hz, 1H), 8.67 (s, 0.5H), 8.21 (s, 0.5H), 7.55 (m, 1H), 7.43 (m, 1H), 7.26-7.09 (m, 2H), 6.82-6.73 (m, 3H), 4.86 (m, 1H), 4.81 (s, 1H), 4.33 (s, 1H), 4.23 (m, 2H), 3.69 (m, 2H), 2.2 (d, J=0.6 Hz, 6H), 2.17 (s, 3H).

EXAMPLE 29

Synthesis of Compound 182

Step 1. Synthesis of methyl 2-(2,4-dimethyl-6-(pyridin-3-yl)phenoxy)acetate: 2,4-dimethyl-6-(pyridin-3-yl)phenol (Compound 6-7) (0.7 g, 3.51 mmol) was dissolved in acetonitrile. Methyl bromoacetate (0.54 g, 3.51 mmol) and cesium carbonate (2.3 g, 7.02 mmol) were added thereto, followed by stirring for 16 hours under reflux. After the completion of the reaction, the reaction mixture was filtered through Celite. The filtrate was added with water, and extracted with ethyl acetate. The obtained organic layer was dried over magnesium sulfate, concentrated under reduced pressure, and purified by column chromatography to obtain methyl 2-(2,4-dimethyl-6-(pyridin-3-yl)phenoxy)acetate (0.71 g, 75%).

Step 2. Synthesis of 2-(2,4-dimethyl-6-(pyridin-3-yl)phenoxy)acetohydrazide: 2-(2,4-dimethyl-6-(pyridin-3-yl)phenoxy)acetate (0.71 g, 2.63 mmol) was dissolved in EtOH. Hydrazine monohydrate (0.13 g, 2.63 mmol) was added thereto, followed by stirring at 100° C. for 16 hours under reflux. After the completion of the reaction, the reaction mixture was concentrated under reduced pressure, and purified by column chromatography to obtain 2-(2,4-dimethyl-6-(pyridin-3-yl)phenoxy)acetohydrazide (0.71 g, 100%).

Step 3. Synthesis of (E)-N'-((1H-indol-4-yl)methylene)-2-(2,4-dimethyl-6-(pyridin-3-yl)phenoxy)acetohydrazide: 2-(2,4-dimethyl-6-(pyridin-3-yl)phenoxy)acetohydrazide (0.2 g, 0.74 mmol) and 1H-indol-4-carbaldehyde (0.13 g, 0.88 mmol) were dissolved in ethanol, followed by stirring at 100° C. for 16 hours. After the completion of the reaction, the reaction mixture was concentrated under reduced pressure. The obtained concentrate was purified by column chromatography to obtain Compound 182 (0.1 g, 34%).

$^1$H NMR (400 MHz, DMSO-$d_6$): δ 11.32 (bs, 1H), 11.22 (bs, 1H), 8.78-8.75 (m, 1H), 8.57-8.50 (m, 1.5H), 8.04-7.98 (m, 1.5H), 7.48-7.41 (m, 3H), 7.21-7.01 (m, 4.5H), 6.33 (m, 0.5H), 4.46-4.00 (m, 2H), 2.35-2.27 (m, 6H).

EXAMPLE 30

Synthesis of Compound 183

2-(2,4-dimethyl-6-(pyridin-3-yl)phenoxy)acetohydrazide (0.2 g, 0.74 mmol) and 1H-indol-6-carbaldehyde (0.13 g, 0.88 mmol) were dissolved in ethanol, followed by stirring at 100° C. for 16 hours. After the completion of the reaction, the reaction mixture was concentrated under reduced pressure. The concentrate was purified by column chromatography to obtain Compound 183 (0.14 g, 47%).

$^1$H NMR (400 MHz, DMSO-$d_6$): δ 11.29-11.14 (m, 2H), 8.77-8.74 (m, 1H), 8.52-8.51 (m, 1H), 8.36 (s, 0.5H), 8.02-7.96 (m, 1H), 7.87 (s, 0.5H), 7.67-7.33 (m, 5H), 7.11-7.05 (m, 2.5H), 6.45-6.41 (m, 1H), 4.41-3.97 (m, 2H), 2.37-2.21 (m, 9H).

EXAMPLE 31

Synthesis of Compound 184

2-(2,4-dimethyl-6-(pyridin-3-yl)phenoxy)acetohydrazide (0.2 g, 0.74 mmol) and 1H-indol-5-carbaldehyde (0.13 g, 0.88 mmol) were dissolved in ethanol, followed by stirring at 100° C. for 16 hours. After the completion of the reaction, the reaction mixture was concentrated under reduced pressure. The concentrate was purified by column chromatography to obtain Compound 184 (0.14 g, 48%).

$^1$H NMR (400 MHz, DMSO-$d_6$): δ 11.38-11.32 (m, 1H), 11.11-11.09 (m, 1H), 8.78-8.75 (m, 1H), 8.51 (m, 1H), 8.37 (s, 0.5H), 8.04-7.97 (m, 1H), 7.86-7.77 (m, 1H), 7.58-7.05 (m, 6.5H), 6.51-6.45 (m, 1H), 4.40-3.96 (m, 2H), 2.32-2.27 (m, 6H).

EXAMPLE 32

Synthesis of Compound 187

Step 1. Synthesis of methyl 2-(2-methylpyridin-3-yloxy)acetate: 2-methylpyridin-3-ol (0.6 g, 4.4 mmol) was dissolved in acetonitrile. Methyl bromoacetate (0.41 mL, 4.4 mmol) and cesium carbonate (1.7 g, 5.3 mmol) was added thereto, followed by stirring at 80° C. for 12 hours. After the completion of the reaction, the reaction mixture was added with water, and extracted with ethyl acetate. The obtained organic layer was dried over magnesium sulfate, concentrated under reduced pressure, and purified by column chromatography to obtain methyl 2-(2-methylpyridin-3-yloxy)acetate (0.34 g, 42%), which was used in the next step.

Step 2. Synthesis of 2-(2-methylpyridin-3-yloxy)acetohydrazide: Methyl 2-(2-methylpyridin-3-yloxy)acetate (0.34 g, 1.1 mmol) was dissolved in EtOH. Hydrazine monohydrate (0.14 mL, 1.6 mmol) was added thereto, followed by stirring for 12 hours under reflux. After the completion of the reaction, the reaction mixture was concentrated under reduced pressure. The concentrate was filtered to obtained 2-(2-methylpyridin-3-yloxy)acetohydrazide as a crude state.

Step 3. Synthesis of (E)-N'-((1H-indol-4-yl)methylene)-2-(2-methylpyridin-3-yloxy)acetohydrazide: 2-(4-chloro-2,6-dimethylphenoxy)acetohydrazide (0.1 g, 0.55 mmol) and 1H-indol-4-carbaldehyde (0.088 g, 0.61 mmol) were dissolved in ethanol, followed by stirring for 3 hours under reflux. After the completion of the reaction, the formed solid was filtered to obtain Compound 187 (0.14 g, 82%).

$^1$H NMR (400 MHz, DMSO-$d_6$): δ 11.54 (bs, 1H), 11.42 (m, 1H), 8.49 (s, 0.4H), 8.24 (s, 0.6H), 8.0 (m, 1H), 7.47 (m, 2H), 7.29-7.10 (m, 4H), 6.96 (s, 1H), 5.28 (s, 1.3H), 4.74 (s, 0.7H), 2.39 (d, J=18.2 Hz, 3H).

EXAMPLE 33

Synthesis of Compound 190

Step 1. Synthesis of methyl 2-(2,4-dimethylpyridin-3-yloxy)acetate: 2,4-dimethylpyridin-3-ol (0.5 g, 3.2 mmol) was dissolved in acetonitrile. Methyl bromoacetate (0.35 mL, 3.9 mmol) and cesium carbonate (1.25 g, 3.9 mmol) was added thereto, followed by stirring at 100° C. for 12 hours. After the completion of the reaction, the reaction mixture was added with water, and extracted with ethyl acetate. The obtained organic layer was dried over magnesium sulfate, concentrated under reduced pressure, and purified by column chromatography to obtain methyl 2-(2,4-dimethylpyridin-3-yloxy)acetate (0.18 g, 28%), which was used in the next step.

Step 2. Synthesis of 2-(2,4-dimethylpyridin-3-yloxy)acetohydrazide: methyl 2-(2,4-dimethylpyridin-3-yloxy)acetate (0.18 g, 0.9 mmol) was dissolved in EtOH. Hydrazine monohydrate (0.05 mL, 1.1 mmol) was added thereto, followed by stirring for 3 hours under reflux. After the completion of the reaction, the reaction mixture was concentrated under reduced pressure. The concentrate was recrystallized with ethanol to obtained to obtain 2-(2,4-dimethylpyridin-3-yloxy) acetohydrazide.

Step 3. Synthesis of (E)-N'-((1H-indol-4-yl)methylene)-2-(2,4-dimethylpyridin-3-yloxy)acetohydrazide: 2-(4-chloro-2,6-dimethylphenoxy)acetohydrazide (0.08 g, 0.41 mmol) and 1H-indol-4-carbaldehyde (0.065 g, 0.45 mmol) were dissolved in ethanol, followed by stirring for 3 hours under reflux. After the completion of the reaction, the formed solid was collected by filtration from the reaction mixture, and purified by column chromatography to obtain Compound 190 (0.045 g, 33%).

$^1$H NMR (400 MHz, DMSO-$d_6$): δ 11.52-11.33 (m, 1H), 8.62 (s, 0.5H), 8.2 (s, 0.5H,), 8.08 (m, 1H), 7.49-6.77 (m, 6H), 4.94 (s, 1H), 4.45 (s, 1H), 2.47 (m, 3H), 2.29 (m, 3H).

EXAMPLE 34

Synthesis of Compound 191

2-(4-chloro-2,6-dimethylphenoxy)acetohydrazide (0.065 g, 0.33 mmol) and 1H-indol-6-carbaldehyde (0.053 g, 0.36 mmol) were dissolved in ethanol, followed by stirring for 12 hours under reflux. After the completion of the reaction, the reaction mixture was concentrated under reduced pressure.

The concentrate was purified by column chromatography to obtain Compound 191 (0.088 g, 82%).
$^1$H NMR (400 MHz, DMSO-d$_6$): δ 11.41 (m, 1H), 11.25 (m, 1H), 8.43 (s, 0.5H), 8.06 (m, 1.5H,), 7.7-7.07 (m, 5H), 6.43 (m, 1H), 4.86 (s, 1H), 4.66 (s, 1H), 2.39 (d, J=3.08 Hz, 3H), 2.28 (d, J=3.08 Hz, 3H).

EXAMPLE 35

Synthesis of Compound 192

Step 1. Synthesis of methyl 2-(2-(trifluoromethyl)phenoxy)acetate: 2-(trifluoromethyl)phenol (1 g, 6.2 mmol) was dissolved in acetonitrile. Methyl bromoacetate (0.94 g, 6.2 mmol) and cesium carbonate (4 g, 12 mmol) were added thereto, followed by stirring for 16 hours. After the completion of the reaction, the reaction mixture was filtered through Celite. The filtrate was added with a saturated sodium hydrogen carbonate aqueous solution, and extracted with ethyl acetate. The obtained organic layer was dried over magnesium sulfate, and concentrated under reduced pressure to obtain methyl 2-(2-(trifluoromethyl)phenoxy)acetate (1.4 g, 100%), which was used in the next step.
Step 2. Synthesis of 2-(2-(trifluoromethyl)phenoxy)acetohydrazide: methyl 2-(2-(trifluoromethyl)phenoxy)acetate (1.4 g, 6.2 mmol) was dissolved in EtOH. Hydrazine monohydrate (2 g, 40 mmol) was added thereto, followed by stirring for 16 hours under reflux. After the completion of the reaction, the reaction mixture was concentrated under reduced pressure. The concentrate was added with water, and extracted with dichloromethane. The obtained organic layer was dried over magnesium sulfate, and concentrated under reduced pressure to obtain 2-(2-(trifluoromethyl)phenoxy)acetohydrazide (1.4 g, 96%).
Step 3. Synthesis of (E)-N'-((1H-indol-4-yl)methylene)-2-(2-(trifluoromethyl)phenoxy)acetohydrazide: 2-(2-(trifluoromethyl)phenoxy)acetohydrazide (0.2 g, 0.85 mmol) and 1H-indol-4-carbaldehyde (0.13 g, 0.85 mmol) were dissolved in ethanol, followed by stirring at 100° C. for 16 hours. After the completion of the reaction, the reaction mixture was concentrated under reduced pressure. The concentrate was purified by column chromatography to obtain Compound 192 (0.27 g, 88%).
$^1$H NMR (400 MHz, DMSO-d$_6$): δ 11.57-11.33 (m, 2H), 8.43-8.25 (m, 1H), 7.64-7.44 (m, 4H), 7.25-6.96 (m, 6H), 5.37-4.84 (m, 2H).

EXAMPLE 36

Synthesis of Compound 193

2-(2-(trifluoromethyl)phenoxy)acetohydrazide (0.2 g, 0.85 mmol) and 1H-indol-5-carbaldehyde (0.13 g, 0.85 mmol) were dissolved in ethanol, followed by stirring at 100° C. for 16 hours.
After the completion of the reaction, the reaction mixture was concentrated under reduced pressure. The concentrate was purified by column chromatography to obtain Compound 193 (0.18 g, 43%).
$^1$H NMR (400 MHz, DMSO-d$_6$): δ 11.57-11.33 (m, 2H), 8.25-8.06 (m, 1H), 7.77-7.79 (m, 1H), 7.62-7.51 (m, 4H), 7.41-7.36 (m, 2.5H), 7.16-7.07 (m, 2.5H), 7.47 (m, 1H), 5.30-4.79 (m, 2H).

EXAMPLE 37

Synthesis of Compound 194

2-(2-(trifluoromethyl)phenoxy)acetohydrazide (0.2 g, 0.85 mmol) and 1H-indol-6-carbaldehyde (0.13 g, 0.85 mmol) were dissolved in ethanol, followed by stirring at 100° C. for 16 hours After the completion of the reaction, the reaction mixture was concentrated under reduced pressure. The concentrate was purified by column chromatography to obtain Compound 194 (0.17 g, 55%).
$^1$H NMR (400 MHz, DMSO-d$_6$): δ 11.49-11.26 (m, 2H), 8.27-8.07 (m, 1H), 7.71-7.54 (m, 4H), 7.44-7.42 (m, 2H), 7.20-7.06 (m, 2H), 6.45 (s, 1H), 5.31-4.80 (m, 2H).

EXAMPLE 38

Synthesis of Compound 196

Step 1. Synthesis of methyl 2-(2-chloropyridin-3-yloxy)acetate: 2-chloropyridin-3-ol (0.6 g, 4.6 mmol) was dissolved in acetonitrile. Methyl bromoacetate (0.52 mL, 9.26 mmol) and cesium carbonate (1.8 g, 5.6 mmol) were added thereto, followed by stirring for 3 hours. After the completion of the reaction, the reaction mixture was added with water, and extracted with dichloromethane. The obtained organic layer was dried over magnesium sulfate, concentrated under reduced pressure, and purified by column chromatography to obtain methyl 2-(2-chloropyridin-3-yloxy)acetate (0.86 g, 92%), which was used in the next step.
Step 2. Synthesis of 2-(2-chloropyridin-3-yloxy)acetohydrazide: methyl 2-(2-chloropyridin-3-yloxy)acetate (0.4 g, 1.98 mmol) was dissolved in EtOH. Hydrazine monohydrate (0.1 mL, 2.2 mmol) was added thereto, followed by stirring for 12 hours under reflux. After the completion of the reaction, the reaction mixture was concentrated under reduced pressure to obtain 2-(2-chloropyridin-3-yloxy)acetohydrazide.
Step 3. Synthesis of (E)-N'-((1H-indol-4-yl)methylene)-2-(2-chloropyridin-3-yloxy)acetohydrazide: 2-(2-chloropyridin-3-yloxy)acetohydrazide (0.1 g, 0.49 mmol) and 1H-indol-4-carbaldehyde (0.086 g, 0.59 mmol) were dissolved in ethanol, followed by stirring at 100° C. for 12 hours. After the completion of the reaction, the formed solid compound was filtered to obtain Compound 196 (0.15 g, 92%).
$^1$H NMR (400 MHz, DMSO-d$_6$): δ 11.61 (bs, 1H), 11.36 (m, 1H), 8.46 (s, 0.2H), 8.25 (s, 0.8H), 7.56-7.09 (m, 7H), 6.97 (m, 1H), 5.42 (s, 1.5H), 4.88 (s, 0.5H), 4.9 (m, 1H), 4.88 (s 2H), 4.08 (t, J=6.28 Hz, 2H), 3.58 (m, 2H), 2.18 (d, J=4.28 Hz, 9H).

EXAMPLE 39

Synthesis of Compound 205

2-(mesityloxy)acetohydrazide (0.10 g, 0.48 mmol) and 1H-benzo[d]imidazole-5-carbaldehyde (0.079 g, 0.48 mmol) were dissolved in EtOH, followed by stirring at 100° C. for 16 hours. After the completion of the reaction, the reaction mixture was cooled to room temperature, and concentrated under reduced pressure. The resulting solid was purified by column chromatography to obtain Compound 205 (0.058 g, 36%).
$^1$H NMR (400 MHz, DMSO-d$_6$): δ 12.62-12.48 (m, 1H), 11.47-11.39 (m, 1H), 8.52 (s, 0.5H), 8.29-8.23 (m, 1H), 8.05 (s, 0.5H), 7.88-7.43 (m, 3H), 6.83-6.82 (m, 2H), 4.74-4.31 (m, 2H), 2.23-2.14 (m, 9H).

EXAMPLE 40

Synthesis of Compound 206

2-(mesityloxy)acetohydrazide (0.10 g, 0.39 mmol) and benzo[d][1,2,3]thiadiazole-5-carbaldehyde (0.079 g, 0.48 mmol) were dissolved in EtOH, followed by stirring at 100° C. for 16 hours. After the completion of the reaction, the reaction mixture was cooled to room temperature, and concentrated under reduced pressure. The resulting solid was purified by column chromatography and by recrystallization to obtain Compound 206 (0.11 g, 65%).

$^1$H NMR (400 MHz, DMSO-$d_6$): δ 11.81-11.73 (m, 1H), 8.89-8.85 (m, 1H), 8.69 (s, 0.5H), 8.47-8.36 (m, 1H), 8.23-8.07 (s, 1.5H), 6.84-8.81 (m, 2H), 4.80-4.36 (m, 2H), 2.22-2.16 (m, 9H).

EXAMPLE 41

Synthesis of Compound 211

2-(mesityloxy)acetohydrazide (0.10 g, 0.39 mmol) and 3-((4-methylpiperidin-1-yl)methyl)-1H-indol-4-carbaldehyde (0.089 g, 0.42 mmol) were dissolved in dimethylsulfoxide, followed by stirring at room temperature for 12 hours. After the completion of the reaction, the reaction mixture was cooled to room temperature, added with water, and extracted with ethyl acetate. The obtained organic layer was dried over magnesium sulfate, and concentrated under reduced pressure. The formed solid was filtered to obtain Compound 211 (0.078 g, 45%).

$^1$H NMR (400 MHz, DMSO-$d_6$): δ 11.42-11.17 (m, 1H), 11.1 (m, 1H), 9.08 (s, 0.5H), 8.6 (s, 0.5H), 7.59 (d, J=7.60 Hz, 5H), 7.43-7.27 (m, 1.5H), 7.13 (t, J=7.68 Hz, 0.5H), 7.0.3 (t, J=7.72 Hz, 0.5H), 6.83 (d, J=10.0 Hz, 2H), 4.74 (s, 1H), 4.34 (s, 1H), 3.59 (s, 1H), 3.50 (m, 1H), 2.86 (m, 2H), 2.23 (s, 3H), 2.18 (m, 6H), 1.86 (m, 2H), 1.47 (m, 2H), 1.28 (m, 1H), 1.01 (m, 2H), 0.81 (m, 3H).

EXAMPLE 42

Synthesis of Compound 217

Step 1. Synthesis of methyl 2-(2,4-dimethyl-6-(pyridin-4-yl)phenoxy)acetate: 2,4-dimethyl-6-(pyridin-4-yl)phenol (Compound 6-8) (0.12 g, 0.6 mmol) was dissolved in acetonitrile. Methyl bromoacetate (0.092 g, 0.6 mmol) and cesium carbonate (0.2 g, 0.6 mmol) were added thereto, followed by stirring for 16 hours. After the completion of the reaction, the reaction mixture was concentrated under reduced pressure, and purified by column chromatography to obtain methyl 2-(2,4-dimethyl-6-(pyridin-4-yl)phenoxy)acetate (0.1 g, 61%).

Step 2. Synthesis of 2-(2,4-dimethyl-6-(pyridin-4-yl)phenoxy)acetohydrazide: 2-(2,4-dimethyl-6-(pyridin-4-yl)phenoxy)acetate (0.1 g, 0.37 mmol) was dissolved in EtOH. Hydrazine monohydrate (0.13 g, 2.63 mmol) was added thereto, followed by stirring at 100° C. for 16 hours under reflux. After the completion of the reaction, the reaction mixture was concentrated under reduced pressure, and purified by column chromatography to obtain 2-(2,4-dimethyl-6-(pyridin-3-yl)phenoxy)acetohydrazide (0.1 g, 100%).

Step 3. Synthesis of (E)-N'-((1H-indol-6-yl)methylene)-2-(2,4-dimethyl-6-(pyridin-4-yl)phenoxy)acetohydrazide: 2-(2,4-dimethyl-6-(pyridin-3-yl)phenoxy)acetohydrazide (0.06 g, 0.22 mmol) and 1H-indol-4-carbaldehyde (0.032 g, 0.22 mmol) were dissolved in ethanol, followed by stirring for 16 hours under reflux. After the completion of the reaction, the reaction mixture was concentrated under reduced pressure. The concentrate was purified by column chromatography to obtain Compound 217 (0.04 g, 45%).

$^1$H NMR (400 MHz, DMSO-$d_6$): δ 11.28-11.12 (m, 2H), 8.61-8.58 (m, 2H), 8.38-7.89 (2s, 1H), 7.68 (s, 0.5H), 7.63-7.34 (m, 5.5H), 7.14-7.09 (m, 2.5H), 6.46-6.42 (m, 1H), 4.44 3.99 (2s, 2H), 2.34-2.29 (m, 6H).

EXAMPLE 43

Synthesis of Compound 218

Step 1. Synthesis of methyl 2-(2-(furan-3-yl)-4,6-dimethylphenoxy)acetate: 2-(furan-3-yl)-4,6-dimethylphenol (Compound 6-2) (0.2 g, 1.1 mmol) was dissolved in acetonitrile. Methyl bromoacetate (0.16 g, 1.1 mmol) and cesium carbonate (0.35 g, 1.1 mmol) were added thereto, followed by stirring for 16 hours. After the completion of the reaction, the reaction mixture was filtered through Celite. The filtrate was concentrated under reduced pressure, and purified by column chromatography to obtain methyl 2-(2-(furan-3-yl)-4,6-dimethylphenoxy)acetate (0.18 g, 64%).

Step 2. Synthesis of 2-(2-(furan-3-yl)-4,6-dimethylphenoxy)acetohydrazide: methyl 2-(2-(furan-3-yl)-4,6-dimethylphenoxy)acetate (0.1 g, 0.38 mmol) was dissolved in EtOH. Hydrazine monohydrate (1 g, 20 mmol) was added thereto, followed by stirring for 16 hours under reflux. After the completion of the reaction, the reaction mixture was concentrated under reduced pressure to obtain 2-(2-(furan-3-yl)-4,6-dimethylphenoxy)acetohydrazide (0.03 g, 30%).

Step 3. Synthesis of (E)-N'-((1H-indol-6-yl)methylene)-2-(2-(furan-3-yl)-4,6-dimethylphenoxy)acetohydrazide: 2-(2-(furan-3-yl)-4,6-dimethylphenoxy)acetohydrazide (0.03 g, 0.12 mmol) and 1H-indol-6-carbaldehyde (0.017 g, 0.12 mmol) were dissolved in ethanol, followed by stirring for 16 hours under reflux. After the completion of the reaction, the reaction mixture was concentrated under reduced pressure. The concentrate was purified by column chromatography to obtain Compound 218 (0.02 g, 45%).

$^1$H NMR (400 MHz, DMSO-$d_6$): δ 11.38-11.37 (m, 1H), 11.29-11.16 (m, 1H), 8.46, 8.30 (2s, 1H), 8.26 (s, 0.5H), 8.00 (s, 0.5H), 7.73 (m, 1.5H), 7.60-7.20 (m, 4.5H), 7.02-6.98 (m, 2H), 6.51-6.39 (m, 1H), 4.66 (s, 1H), 4.20 (m, 1H), 2.30-2.27 (m, 6H).

EXAMPLE 44

Synthesis of Compound 227

Step 1. Synthesis of methyl 2-(4-(hydroxymethyl)-2,6-dimethylphenoxy)acetate: 4-(hydroxymethyl)-2,6-dimethylphenol (0.034 g, 0.22 mmol) was dissolved in methanol. Methyl bromoacetate (0.034 g, 0.22 mmol) and potassium carbonate (0.031 g, 0.22 mmol) were added thereto, followed by stirring for 16 hours. After the completion of the reaction, the reaction mixture was added with a saturated ammonium chloride aqueous solution, and extracted with ethyl acetate. The obtained organic layer was dried over magnesium sulfate, and concentrated under reduced pressure to obtain methyl 2-(4-(hydroxymethyl)-2,6-dimethylphenoxy)acetate (0.04 g, 80%), which was used in the next step.

Step 2. Synthesis of 2-(4-(hydroxymethyl)-2,6-dimethylphenoxy)acetohydrazide: Methyl 2-(4-(hydroxymethyl)-2,6-dimethylphenoxy)acetate (0.3 g, 1.3 mmol) was dissolved in EtOH. Hydrazine monohydrate (1 g, 18 mmol) was added thereto, followed by stirring for 60° C. for 16 hours. After the completion of the reaction, the reaction mixture was concentrated under reduced pressure to obtain 2-(4-(hydroxymethyl)-2,6-dimethylphenoxy)acetohydrazide (0.25 g, 83%).

Step 3. Synthesis of (E)-N'-((1H-indol-4-yl)methylene)-2-(4-(hydroxymethyl)-2,6-dimethylphenoxy)acetohydrazide: 2-(2-(trifluoromethyl)phenoxy)acetohydrazide (0.1 g, 0.45 mmol) and 1H-indol-4-carbaldehyde (0.065 g, 0.45 mmol) were dissolved in ethanol, followed by stirring at 100° C. for 16 hours. After the completion of the reaction, the reaction mixture was concentrated under reduced pressure. The concentrate was purified by column chromatography to obtain Compound 227 (0.05 g, 32%).

$^1$H NMR (400 MHz, DMSO-$d_6$): δ 11.53-11.46 (m, 1H), 11.37 (bs, 1H), 8.69 (s, 1H), 8.22 (s, 1H), 7.50-7.43 (m, 2H), 7.25-7.11 (m, 2.5H), 6.98 (m, 2H), 6.76 (s, 0.5H), 5.10-5.08 (m, 1H), 4.86 (s, 1H), 4.39-4.38 (m, 3H), 2.27-2.26 (m, 6H).

EXAMPLE 45

Synthesis of Compound 228

2-(2-(trifluoromethyl)phenoxy)acetohydrazide (0.07 g, 0.31 mmol) and 1H-indol-6-carbaldehyde (0.045 g, 0.31 mmol) were dissolved in ethanol, followed by stirring for 16 hours under reflux. After the completion of the reaction, the reaction mixture was concentrated under reduced pressure. The concentrate was purified by column chromatography to obtain Compound 228 (0.05 g, 46%).

$^1$H NMR (400 MHz, DMSO-$d_6$): δ 11.44-11.40 (m, 1H), 11.33-11.23 (m, 1H), 8.50-8.03 (2s, 1H), 7.77 (s, 0.5H), 7.59-6.76 (m, 3.5H), 6.98 (s, 2H), 6.47-6.42 (m, 1H), 5.11-5.07 (m, 1H), 4.77 (s, 1H), 4.39-4.34 (m, 3H), 2.26-2.24 (m, 6H).

EXAMPLE 46

Synthesis of Compound 229

Step 1. Synthesis of methyl 2-(2,4-dimethyl-6-(tetrahydrofuran-3-yl)phenoxy)acetate: 2,4-dimethyl-6-(tetrahydrofuran-3-yl)phenol (Compound 7-2) (0.4 g, 2.1 mmol) was dissolved in acetonitrile. Methyl bromoacetate (0.32 g, 2.1 mmol) and cesium carbonate (1.4 g, 4.2 mmol) were added thereto, followed by stirring for 16 hours. After the completion of the reaction, the reaction mixture was filtered through Celite. The filtrate was concentrated under reduced pressure, and purified by column chromatography to obtain methyl 2-(2,4-dimethyl-6-(tetrahydrofuran-3-yl)phenoxy)acetate (0.42 g, 76%).

Step 2. Synthesis of 2-(2,4-dimethyl-6-(tetrahydrofuran-3-yl)phenoxy)acetohydrazide: methyl 2-(2,4-dimethyl-6-(tetrahydrofuran-3-yl)phenoxy)acetate (0.18 g, 0.68 mmol) was dissolved in EtOH. Hydrazine monohydrate (1 g, 20 mmol) was added thereto, followed by stirring for 16 hours under reflux. After the completion of the reaction, the reaction mixture was concentrated under reduced pressure to obtain 2-(2,4-dimethyl-6-(tetrahydrofuran-3-yl)phenoxy)acetohydrazide (0.1 g, 56%).

Step 3. Synthesis of (E)-N'-((1H-indol-6-yl)methylene)-2-(2,4-dimethyl-6-(tetrahydrofuran-3-yl)phenoxy)acetohydrazide: 2-(2,4-dimethyl-6-(tetrahydrofuran-3-yl)phenoxy)acetohydrazide (0.1 g, 0.38 mmol) and 1H-indol-6-carbaldehyde (0.067 g, 0.45 mmol) were dissolved in ethanol, followed by stirring for 16 hours under reflux. After the completion of the reaction, the reaction mixture was concentrated under reduced pressure. The concentrate was purified by column chromatography (ethyl acetate:hexane=2:1) to obtain Compound 229 (0.063 g, 43%).

$^1$H NMR (400 MHz, DMSO-$d_6$): δ 11.48-11.44 (m, 1H), 11.35-11.23 (m, 1H), 8.48 (s, 0.5H), 8.05 (s, 0.5H), 7.72 (s, 0.5H), 7.59-7.27 (m, 3.5H), 6.96-6.88 (m, 2H), 6.47-6.43 (m, 1H), 4.77 (s, 1H), 4.34 (s, 1H), 4.02-3.92 (m, 2H), 3.77-3.73 (m, 2H), 3.53-3.43 (m, 1H), 2.26-2.20 (m, 7H), 1.89-2.20 (m, 1H).

EXAMPLE 47

Synthesis of Compound 237

Step 1. Synthesis of methyl 2-(4-cyano-2,6-dimethylphenoxy)acetate: 4-hydroxy-3,5-dimethylbenzonitrile (200 mg, 1.4 mmol), methyl bromoacetate (0.15 mL, 1.4 mmol) and cesium carbonate (500 mg, 1.68 mmol) were dissolved in acetonitrile 4 mL, followed by stirring at 80° C. for 2 hours. After the completion of the reaction, the reaction mixture was extracted with ethyl acetate, dried over magnesium sulfate, and concentrated under reduced pressure to obtain methyl 2-(4-cyano-2,6-dimethylphenoxy)acetate (303 mg, 99%).

Step 2. Synthesis of 2-(4-cyano-2,6-dimethylphenoxy)acetohydrazide: methyl 2-(4-cyano-2,6-dimethylphenoxy)acetate (200 mg, 0.91 mmol) and hydrazine (0.05 mL, 1.0 mmol) were dissolved in EtOH 2 mL, followed by stirring at 80° C. for 12 hours. After the completion of the reaction, the reaction mixture was concentrated under reduced pressure to obtain 2-(4-cyano-2,6-dimethylphenoxy)acetohydrazide (180 mg, 90%).

Step 3. Synthesis of (E)-N'-((1H-indol-6-yl)methylene)-2-(4-cyano-2,6-dimethylphenoxy)acetohydrazide: 2-(4-cyano-2,6-dimethylphenoxy)acetohydrazide (92 mg, 0.42 mmol) and 1H-indol-6-carbaldehyde (67 mg, 0.46 mmol) were dissolved in EtOH 1 mL, followed by stirring at 80° C. for 12 hours. After the completion of the reaction, the reaction mixture was purified by column chromatography (ethyl acetate:hexane=1:1), recrystallized with hexane/ethyl acetate, and filtered to obtain Compound 237 (31 mg, 21%).

$^1$H NMR (400 MHz, DMSO-$d_6$): δ 11.45 (m, 1H), 11.32-11.24 (m, 1H), 8.45-8.04 (2s, 1H), 7.71 (s, 0.5H), 7.59-7.57 (m, 3H), 7.53-7.38 (m, 2H), 7.27 (m, 0.5H), 6.45 (m, 1H), 4.92 (s, 1H), 4.47 (s, 1H), 2.30 (d, J=4.24 Hz, 6H).

EXAMPLE 48

Synthesis of Compound 256

Compound 108 (100 mg, 0.35 mmol) and NBS (57 mg, 0.35 mmol) were dissolved in $CH_2Cl_2$ 2 mL, followed by stirring at room temperature for 2 hours. After the completion of the reaction, the reaction mixture was filtered. The filtrate was purified by column chromatography (ethyl acetate:hexane=2:1) to obtain Compound 256 (40 mg, 32%).

$^1$H NMR (400 MHz, DMSO-$d_6$): δ 11.45 (bs, 1H), 8.52 (s, 1H), 8.06 (s, 1H), 7.73 (s, 0.5H), 7.61 (m, 1H), 7.54-7.39 (m, 2H), 6.83 (m, 2H), 2.21 (m, 9H).

EXAMPLE 49

Synthesis of Compound 258

2-(2,6-dimethylphenoxy)acetohydrazide (100 mg, 0.51 mmol) and 1H-indol-6-carbaldehyde (74 mg, 0.51 mmol) were dissolved in EtOH 2 mL, followed by stirring at 100° C. for 12 hours. After removing the solvent, the residue was recrystallized with tetrahydrofuran and hexane to obtain Compound 258 (42 mg, 26%).

$^1$H NMR (400 MHz, DMSO-$d_6$): δ 11.38 (m, 1H), 11.29 (m, 1H), 8.49, 8.04 (2s, 1H), 7.71 (s, 0.5H), 7.58 (m, 1H), 7.52-7.27 (m, 2.5H), 7.05 (m, 2H), 6.96 (m, 1H), 6.45 (m, 1H), 4.79 (s, 2H), 4.37 (s, 2H), 2.27 (m, 6H).

EXAMPLE 50

Synthesis of Compound 259

Step 1. Synthesis of methyl 2-(2-bromo-4,6-dimethylphenoxy)acetate: 2-bromo-4,6-dimethylphenol (200 mg, 1.4 mmol), methyl bromoacetate (0.15 mL, 1.4 mmol) and cesium carbonate (500 mg, 1.68 mmol) were dissolved in acetonitrile 4 mL, followed by stirring at 100° C. for 3 hours. After the completion of the reaction, the reaction mixture was extracted with ethyl acetate, dried over magnesium sulfate, and purified by column chromatography (ethyl acetate:hexane=1:3) to obtain methyl 2-(2-bromo-4,6-dimethylphenoxy)acetate (516 mg, 100%).

Step 2. Synthesis of 2-(2-bromo-4,6-dimethylphenoxy)acetohydrazide: methyl 2-(2-bromo-4,6-dimethylphenoxy)acetate (423 mg, 1.55 mmol) and hydrazine (0.08 mL, 1.57 mmol) were dissolved in EtOH 2 mL, followed by stirring at 100° C. for 12 hours. After the completion of the reaction, the reaction mixture was concentrated under reduced pressure to obtain 2-(2-bromo-4,6-dimethylphenoxy)acetohydrazide (393 mg, 93%).

Step 3. Synthesis of (E)-N'-((1H-indol-4-yl)methylene)-2-(2-bromo-4,6-dimethylphenoxy)acetohydrazide: 2-(2-bromo-4,6-dimethylphenoxy)acetohydrazide (85 mg, 0.31 mmol) and 1H-indol-4-carbaldehyde (45 mg, 0.31 mmol) were dissolved in EtOH 2 mL, followed by stirring at 100° C. for 12 hours. After the completion of the reaction, the reaction mixture was concentrated under reduced pressure. The concentrate was recrystallized with ethanol, and filtered to obtain Compound 259 (50 mg, 40%).

$^1$H NMR (400 MHz, DMSO-$d_6$): δ 11.47-11.44 (m, 1H), 11.34 (bs, 1H), 8.68 (s, 1H), 8.23 (s, 1H), 7.47 (m, 2H), 7.25 (m, 2H), 7.17-7.13 (m, 4H), 7.12 (s, 1H), 6.78 (s, 1H), 4.98 (s, 1H), 4.48 (s, 2H), 2.32-2.24 (m, 9H).

EXAMPLE 51

Synthesis of Compound 260

2-(2-bromo-4,6-dimethylphenoxy)acetohydrazide (85 mg, 0.31 mmol) and 1H-indol-6-carbaldehyde (45 mg, 0.31 mmol) were dissolved in EtOH 2 mL, followed by stirring at 100° C. for 12 hours. After the completion of the reaction, the reaction mixture was purified by column chromatography (ethyl acetate:hexane=1:1) to obtain Compound 260 (60 mg, 48%).

$^1$H NMR (400 MHz, DMSO-$d_6$): δ 11.38 (s, 1H), 11.29-11.20 (m, 1H), 8.48-8.02 (2s, 1H), 7.71 (s, 0.5H), 7.58-7.25 (m, 3H), 7.28-7.25 (m, 0.5H), 7.05 (m, 1H), 6.45 (m, 1H), 4.88, (2s, 2H), 2.28 (m, 6H).

EXAMPLE 52

Synthesis of Compound 279

2-(o-tosyloxy)acetohydrazide (100 mg, 0.56 mmol) and 1H-indol-6-carbaldehyde (81 mg, 0.56 mmol) were dissolved in EtOH 2 mL, followed by stirring at 90° C. for 6 hours. After the completion of the reaction, the formed solid was filtered to obtain Compound 279 (50 mg, 29%).

$^1$H NMR (400 MHz, DMSO-$d_6$): δ 11.30 (m, 1H), 11.28 (m, 1H), 8.34 (s, 0.5H), 8.08 (s, 0.5H), 7.67 (d, J=2.8 Hz, 1H), 7.46-7.37 (m, 2H), 7.18-7.10 (m, 2H), 6.89-6.81 (m, 2H), 6.47 (m, 1H), 5.15 (s, 1H), 4.65 (s, 1H), 2.23 (d, J=13.2 Hz, 3H).

EXAMPLE 53

Synthesis of Compound 280

Step 1. Synthesis of 1-(phenylsulfonyl)-1H-indol-6-carbaldehyde: 1H-indol-4-carbaldehyde (1000 mg, 6.89 mmol), sodium hydride (360 mg, 8.26 mmol) and benzylsulfonyl chloride (1 mL, 6.89 mmol) were dissolved in tetrahydrofuran 10 mL, followed by stirring at room temperature for 12 hours. After the completion of the reaction, the reaction mixture was extracted with ethyl acetate, dried over magnesium sulfate, and purified by column chromatography (ethyl acetate:hexane=1:3) to obtain 1-(phenylsulfonyl)-1H-indol-6-carbaldehyde (500 mg, 25%).

Step 2. Synthesis of (E)-2-(mesityloxy)-N'-((1-(phenylsulfonyl)-1H-indol-4-yl)methylene)acetohydrazide: 2-(mesityloxy)acetohydrazide (30 mg, 0.14 mmol) and 1H-indol-4-carbaldehyde (44 mg, 0.16 mmol) were dissolved in EtOH 2 mL, followed by stirring at 100° C. for 12 hours. After the completion of the reaction, the formed solid was filtered to obtain Compound 280 (30 mg, 39%).

$^1$H NMR (400 MHz, DMSO-$d_6$): δ 11.64 (m, 1H), 8.65-8.18 (2s, 1H), 8.02-7.97 (m, 4H), 7.7-7.2 (m, 6H), 4.78 (s, 1H), 4.36 (s, 1H), 2.20 (m, 9H).

EXAMPLE 54

Synthesis of Compound 286

Step 1. Synthesis of methyl 2-(2,6-dimethylpyridin-4-yloxy)acetate: 2,6-dimethylpyridin-4-ol (300 mg, 2.44 mmol), methyl 2-bromoacetate (0.27 mL, 2.93 mmol) and cesium carbonate (2.4 g, 7.32 mmol) were dissolved in acetonitrile 6 mL, followed by stirring at 80° C. for 1 hour. After the completion of the reaction, the reaction mixture was filtered under reduced pressure. The filtrate was concentrated under reduced pressure, and purified by column chromatography (hexane:ethyl acetate=3:1) to obtain methyl 2-(4-fluoro-2-methylphenoxy)acetate (200 mg, 42%).

Step 2. Synthesis of 2-(2,6-dimethylpyridin-4-yloxy)acetohydrazide: methyl 2-(2,6-dimethylpyridin-4-yloxy)acetate (200 mg, 1.03 mmol) and hydrazine (0.05 mL, 1.13 mmol) were dissolved in EtOH 3 mL, followed by stirring at 100° C. for 12 hours. After the completion of the reaction, the formed solid was filtered to obtain 2-(4-fluoro-2-methylphenoxy)acetohydrazide (190 mg, 79%).

Step 2. Synthesis of (E)-N'-((1H-indol-4-yl)methylene)-2-(2,6-dimethylpyridin-4-yloxy)acetohydrazide: 2-(2,6-dimethylpyridin-4-yloxy)acetohydrazide (30 mg, 0.15 mmol) and 1H-indol-4-carbaldehyde (22 mg, 0.15 mmol) were dissolved in EtOH 2 mL, followed by stirring at 90° C. for 12 hours. After the completion of the reaction, the formed solid was filtered to obtain Compound 286 (20 mg, 41%).

$^1$H NMR (400 MHz, DMSO-$d_6$): δ 11.53 (m, 1H), 11.38 (m, 1H), 8.53-8.26 (s, 1H), 7.49 (m, 2H), 7.19 (m, 2.5H), 7.11 (s, 0.5H), 6.70-6.64 (m, 2H), 5.26 (s, 1H), 4.74 (s, 1H), 2.34 (m, 6H).

EXAMPLE 55

Synthesis of Compound 288

2-(2,6-dimethylpyridin-4-yloxy)acetohydrazide (100 mg, 0.51 mmol) and 1H-indol-6-carbaldehyde (74 mg, 0.51 mmol) were dissolved in EtOH 2 mL, followed by stirring at 110° C. for 12 hours. The reaction mixture was added with water, and extracted with ethyl acetate. The obtained organic layer was dried over magnesium sulfate, and purified by column chromatography (hexane:ethyl acetate=2:1) to obtain Compound 288 (30 mg, 18%).

$^1$H NMR (400 MHz, DMSO-d$_6$): δ 11.43 (m, 1H), 11.28 (m, 1H), 8.35-8.07 (2s, 1H), 7.68 (d, J=18.0 Hz, 1H), 7.57 (d, J=8.4 Hz, 1H), 6.66 (d, J=22.0 Hz, 2H), 6.47 (s, 1H), 5.20 (s, H), 4.69 (s, 1H), 2.34 (m, 6H).

EXAMPLE 56

Synthesis of Compound 291

Step 1. Synthesis of methyl 2-(4-fluoro-2-methylphenoxy)acetate: 4-fluoro-2-methylphenol (500 mg, 3.96 mmol), methyl 2-bromoacetate (0.36 mL, 3.96 mmol) and cesium carbonate (1.9 mg, 5.94 mmol) were dissolved in acetonitrile 8 mL, followed by stirring at 90° C. for 5 hours. The reaction mixture was added with water, and extracted with ethyl acetate. The obtained organic layer was dried over magnesium sulfate, and purified by column chromatography (hexane:ethyl acetate=3:1) to obtain methyl 2-(4-fluoro-2-methylphenoxy)acetate (450 mg, 57%).

Step 2. Synthesis of 2-(4-fluoro-2-methylphenoxy)acetohydrazide: methyl 2-(4-fluoro-2-methylphenoxy)acetate (400 mg, 2.02 mmol) and hydrazine (0.12 mL, 2.42 mmol) were dissolved in EtOH 4 mL, followed by stirring at 90° C. for 3 hours. After the completion of the reaction, the formed solid was filtered to obtain 2-(4-fluoro-2-methylphenoxy) acetohydrazide (280 mg, 70%).

Step 3. Synthesis of (E)-N'-((1H-indol-6-yl)methylene)-2-(4-fluoro-2-methylphenoxy)acetohydrazide: 2-(4-fluoro-2-methylphenoxy)acetohydrazide (100 mg, 0.50 mmol) and 1H-indol-6-carbaldehyde (73 mg, 0.50 mmol) were dissolved in EtOH 2 mL, followed by stirring at 90° C. for 4 hours. The reaction mixture was added with water, and extracted with ethyl acetate. The obtained organic layer was dried over magnesium sulfate, and purified by column chromatography (hexane:ethyl acetate=2:1) to obtain Compound 291 (37 mg, 23%).

$^1$H NMR (400 MHz, DMSO-d$_6$): δ 11.43-11.41 (m, 1H), 11.34-11.30 (m, 1H), 8.34-8.07 (2s, 1H), 7.72 (d, J=27.7 Hz, 1H), 7.64 (m, 1H), 7.44 (m, 2H), 6.95 (m, 3H), 5.15 (s, H), 4.63 (s, H), 2.22 (s, 3H)

EXAMPLE 57

Synthesis of Compound 293

Step 1. Synthesis of methyl 2-(2-ethyl-6-methylpyridin-3-yloxy)acetate: 2-ethyl-6-methylpyridin-3-ol (500 mg, 3.62 mmol), methyl 2-bromoacetate (0.33 mL, 3.62 mmol) and cesium carbonate (1.78 g, 5.43 mmol) were dissolved in acetonitrile 5 mL, followed by stirring at 100° C. for 5 hours. After the completion of the reaction, the reaction mixture was added with water, and extracted with ethyl acetate. The obtained organic layer was dried over magnesium sulfate, and purified by column chromatography (hexane:ethyl acetate=3:1) to obtain methyl 2-(2-ethyl-6-methylpyridin-3-yloxy)acetate (565 mg, 70%).

Step 2. Synthesis of 2-(2-ethyl-6-methylpyridin-3-yloxy) acetohydrazide: methyl 2-(2-ethyl-6-methylpyridin-3-yloxy)acetate (400 mg, 1.79 mmol) and hydrazine (0.1 mL, 2.15 mmol) were dissolved in EtOH 4 mL, followed by stirring at 90° C. for 5 hours. After the completion of the reaction, the reaction mixture was filtered under reduced pressure to obtain 2-(2-ethyl-6-methylpyridin-3-yloxy)acetohydrazide (242 mg, 65%).

Step 3. Synthesis of (E)-N'-((1H-indol-6-yl)methylene)-2-(2-ethyl-6-methylpyridin-3-yloxy)acetohydrazide: 2-(2-ethyl-6-methylpyridin-3-yloxy)acetohydrazide (100 mg, 0.50 mmol) and 1H-indol-6-carbaldehyde (73 mg, 0.50 mmol) were dissolved in EtOH 3 mL, followed by stirring at 90° C. for 4 hours. After the completion of the reaction, the formed solid was filtered to obtain Compound 293 (46 mg, 29%).

$^1$H NMR (400 MHz, DMSO-d$_6$): δ 11.43 (bs, 1H), 11.30-11.27 (s, 1H), 8.32-8.06 (2s, 1H), 7.64 (m, 1H), 7.42 (m, 2H), 7.36 (m, 1H), 7.02 (m, 1H), 6.45 (s, 1H), 5.17 (s, 1H), 4.66 (s, 1H), 2.75 (m, 2H), 2.45 (s, 3H), 1.21 (m, 3H).

EXAMPLE 58

Synthesis of Compound 301

Step 1. Synthesis of methyl 2-(2,6-dimethylpyrimidin-4-yloxy)acetate: 2,6-dimethylpyrimidin-4-ol (300 mg, 2.42 mmol), methyl bromoacetate (0.22 mL, 2.90 mmol) and cesium carbonate (945 mg, 2.90 mmol) were dissolved in acetonitrile 4 mL, followed by stirring at 80° C. for 2 hours. After the completion of the reaction, the reaction mixture was filtered under reduced pressure. The filtrate was concentrated under reduced pressure, and purified by column chromatography (ethyl acetate:hexane=1:3) to obtain methyl 2-(2,6-dimethylpyrimidin-4-yloxy)acetate (170 mg, 36%).

Step 2. Synthesis of 2-(2,6-dimethylpyrimidin-4-yloxy) acetohydrazide: methyl 2-(2,6-dimethylpyrimidin-4-yloxy) acetate (170 mg, 0.87 mmol) and hydrazine (0.05 mL, 0.95 mmol) were dissolved in EtOH 2 mL, followed by stirring at 100° C. for 12 hours. After the completion of the reaction, the reaction mixture was concentrated under reduced pressure to obtain 2-(2,6-dimethylpyrimidin-4-yloxy)acetohydrazide (149 mg, 88%).

Step 3. Synthesis of (E)-N'-((1H-indol-4-yl)methylene)-2-(2,6-dimethylpyrimidin-4-yloxy)acetohydrazide: 2-(2,6-dimethylpyrimidin-4-yloxy)acetohydrazide (57 mg, 0.29 mmol) and 1H-indol-4-carbaldehyde (42 mg, 0.30 mmol) were dissolved in EtOH 1 mL, followed by stirring at 100° C. for 12 hours. After the completion of the reaction, the formed solid was filtered to obtain Compound 301 (20 mg, 21%).

$^1$H NMR (400 MHz, DMSO-d$_6$): δ 11.51-11.33 (m, 2H), 8.47-8.24 (m, 1H), 7.49 (m, 2H), 7.19 (m, 2H), 7.10 (m, 1H), 6.71 (m, 1H), 5.47 (s, 1H), 4.94 (s, 1H).

EXAMPLE 59

Synthesis of Compound 302

Step 1. Synthesis of methyl 2-(2-tert-butyl-4-methoxyphenoxy)acetate: 2-tert-butyl-4-methoxyphenol (300 mg, 1.67 mmol), methyl bromoacetate (0.18 mL, 2.00 mmol) and cesium carbonate (653 mg, 2.00 mmol) were dissolved in acetonitrile 4 mL, followed by stirring at 80° C. for 1 hour. After the completion of the reaction, the reaction mixture was filtered under reduced pressure. The filtrate was concentrated under reduced pressure, and purified by column chromatography (ethyl acetate:hexane=1:3) to obtain methyl 2-(2-tert-butyl-4-methoxyphenoxy)acetate (259 mg, 62%).

Step 2. Synthesis of 2-(2-tert-butyl-4-methoxyphenoxy) acetohydrazide: methyl 2-(2-tert-butyl-4-methoxyphenoxy) acetate (259 mg, 1.03 mmol) and hydrazine (0.06 mL, 1.13 mmol) were dissolved in EtOH 2 mL, followed by stirring at 80° C. for 12 hours. After the completion of the reaction, the reaction mixture was concentrated under reduced pressure to obtain 2-(2-tert-butyl-4-methoxyphenoxy)acetohydrazide (231 mg, 89%).

Step 3. Synthesis of (E)-N'-((1H-indol-4-yl)methylene)-2-(2-tert-butyl-4-methoxyphenoxy)acetohydrazide: 2-(2-tert-butyl-4-methoxyphenoxy)acetohydrazide (90 mg, 0.36 mmol) and 1H-indol-4-carbaldehyde (57 mg, 0.39 mmol) were dissolved in EtOH 2 mL, followed by stirring at 90° C. for 12 hours. After the completion of the reaction, the formed solid was filtered to obtain Compound 302 (60 mg, 44%).

$^1$H NMR (400 MHz, DMSO-d$_6$): δ 11.50 (m, 1H), 11.37 (m, 1H), 8.47-8.27 (2s, 1H), 7.49 (m, 2H), 7.16 (m, 2H), 6.95 (m, 1H), 6.80 (m, 1H), 6.74 (m, 2H), 5.13 (s, 1H), 4.12 (s, 1H), 3.69 (s, 3H), 1.38 (s, 9H).

EXAMPLE 60

Synthesis of Compound 303

2-(2-tert-butyl-4-methoxyphenoxy)acetohydrazide (90 mg, 0.36 mmol) and 1H-indol-6-carbaldehyde (57 mg, 0.39 mmol) were dissolved in EtOH 2 mL, followed by stirring at 90° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:2) to obtain Compound 303 (66 mg, 48%).

$^1$H NMR (400 MHz, DMSO-d$_6$): δ 11.41 (m, 1H), 11.26 (m, 1H), 8.31-8.08 (2s, 1H), 7.71 (m, 1H), 7.56 (m, 1H), 7.38 (m, 2H), 6.85 (m, 1H), 6.74 (m, 2H), 6.46 (m, 2H), 5.06 (s, 1H), 4.58 (s, 1H), 3.69 (s, 3H), 1.36 (s, 9H).

EXAMPLE 61

Synthesis of Compound 304

Step 1. Synthesis of methyl 2-((2-methylpyridin-3-yl)oxy)acetate: 3-hydroxy-2-methylpyridine (500 mg, 4.58 mmol) and methyl bromoacetate (0.48 mL, 5.04 mmol) were dissolved in acetonitrile. Cesium carbonate (2.24 g, 6.82 mmol) was added thereto, followed by stirring at room temperature for 1 day. After the completion of the reaction, the reaction mixture was added with a saturated sodium hydrogen carbonate aqueous solution, and extracted with ethyl acetate. The obtained organic layer was washed with brine, dried over sodium sulfate anhydrous, filtered, and concentrated under reduced pressure. The concentrated residue was purified by column chromatography (silica gel; hexane/ethyl acetate, 6/4) to obtain methyl 2-((2-methylpyridin-3-yl)oxy)acetate (356 mg, 43%).

Step 2. Synthesis of 2-((2-methylpyridin-3-yl)oxy)acetohydrazide: Compound 1-2 (methyl 2-((2-methylpyridin-3-yl)oxy)acetate, 356 mg, 1.94 mmol) and hydrazine monohydrate (0.19 mL, 3.93 mmol) were dissolved in ethanol, followed by stirring for 1 day under reflux. After the completion of the reaction, the reaction mixture was concentrated under reduced pressure. The concentrated residue was dried and purified to obtain 2-((2-methylpyridin-3-yl)oxy)acetohydrazide (240 mg, 67%) as a white solid.

Step 3. Synthesis of (E)-N'-((1H-indol-6-yl)methylene)-2-((2-methylpyridin-3-yl)oxy)acetohydrazide: 2-((2-methylpyridin-3-yl)oxy)acetohydrazide (240 mg, 1.32 mmol) and indol-6-carboxaldehyde (211.6 mg, 1.46 mmol) were dissolved in ethanol, followed by stirring overnight under reflux. After the completion of the reaction, the reaction mixture was concentrated under reduced pressure. The concentrated residue was purified by column chromatography (silica gel; methylene chloride/methanol, 10/1) to obtain Compound 304 (46 mg, 11%) as a brown solid.

$^1$H NMR (400 MHz, DMSO-d$_6$): δ 11.47 (m, 1H), 11.29 (m, 1H), 8.34-8.00 (m, 2H), 7.69 (d, 1H, J=23.4 Hz), 7.58 (d, 1H, J=8.2 Hz), 7.47-7.32 (m, 2H), 7.29-7.23 (m, 1H), 7.21-7.13 (m, 1H), 6.47 (s, 1H), 5.24-4.73 (m, 2H), 2.43 (s, 3H).

EXAMPLE 62

Synthesis of Compound 310

Step 1. Synthesis of methyl 2-(2-(furan-3-yl)pyridin-3-yloxy)acetate: 2-(furan-3-yl)pyridin-3-ol (Compound 6-10) (100 mg, 0.62 mmol), methyl bromoacetate (0.07 mL, 0.75 mmol) and cesium carbonate (244 mg, 0.75 mmol) were dissolved in acetonitrile 4 mL, followed by stirring at 80° C. for 12 hours. After the completion of the reaction, the reaction mixture was filtered under reduced pressure, and concentrated under reduced pressure. The concentrate was purified by column chromatography (ethyl acetate:hexane=1:3) to obtain methyl 2-(2-(furan-3-yl)pyridin-3-yloxy)acetate (128 mg, 89%).

Step 2. Synthesis of 2-(2-(furan-3-yl)pyridin-3-yloxy)acetohydrazide: methyl 2-(2-(furan-3-yl)pyridin-3-yloxy)acetate (128 mg, 0.54 mmol) and hydrazine (0.03 mL, 0.6 mmol) were dissolved in EtOH 2 mL, followed by stirring at 90° C. for 6 hours. After the completion of the reaction, the reaction mixture was concentrated under reduced pressure to obtain 2-(2-(furan-3-yl)pyridin-3-yloxy)aceto-hydrazide (108 mg, 84%).

Step 3. Synthesis of (E)-N'-((1H-indol-6-yl)methylene)-2-(2-(furan-3-yl)pyridin-3-yloxy)acetohydrazide: 2-(2-(furan-3-yl)pyridin-3-yloxy)acetohydrazide (100 mg, 0.43 mmol) and 1H-indol-6-carbaldehyde (70 mg, 0.44 mmol) were dissolved in EtOH 2 mL, followed by stirring at 100° C. for 12 hours. After the completion of the reaction, the reaction mixture was added with water, and extracted with ethyl acetate. The obtained organic layer was dried over magnesium sulfate, and purified by column chromatography (ethyl acetate:hexane=3:7) to obtain Compound 310 (60 mg, 39%).

$^1$H NMR (400 MHz, DMSO-d$_6$): δ 11.57 (bs, 1H), 11.30 (bs, 1H), 8.78-8.57 (2s, 1H), 8.30 (s, 0.2H), 8.21 (m, 1H), 8.11 (s, 1H), 7.75 (m, 1H), 7.72 (s, 0.9H), 7.59-7.40 (m, 5H), 7.26 (m, 1H), 7.16 (m, 1H), 6.47 (m, 1H), 5.36 (s, 1H), 4.87 (s, 1H).

EXAMPLE 63

Synthesis of Compound 311

Step 1. Synthesis of methyl 2-(2-methyl-6-(tetrahydrofuran-3-yl)phenoxy)acetate: 2-methyl-6-(tetrahydrofuran-3-yl)phenol (Compound 7-3) (117 mg, 0.66 mmol), methyl bromoacetate (0.07 mL, 0.79 mmol) and cesium carbonate (258 mg, 0.79 mmol) were dissolved in acetonitrile 2 mL, followed by stirring at 100° C. for 2 hours. After the completion of the reaction, the reaction mixture was filtered under reduced pressure, and concentrated under reduced pressure. The concentrate was purified by column chromatography (ethyl acetate:hexane=1:3) to obtain methyl 2-(2-methyl-6-(tetrahydrofuran-3-yl)phenoxy)acetate (141 mg, 86%).

Step 2. Synthesis of 2-(2-methyl-6-(tetrahydrofuran-3-yl)phenoxy)acetohydrazide: methyl 2-(2-methyl-6-(tetrahydrofuran-3-yl)phenoxy)acetate (141 mg, 0.56 mmol) and hydrazine (0.03 mL, 0.6 mmol) were dissolved in EtOH 2 mL, followed by stirring at 100° C. for 12 hours. After the completion of the reaction, the reaction mixture was concentrated under reduced pressure to obtain 2-(2-(furan-3-yl)-6-methylphenoxy)acetohydrazide (127 mg, 90%).

Step 3. Synthesis of (E)-N'-((1H-indol-6-yl)methylene)-2-(2-methyl-6-(tetrahydrofuran-3-yl)phenoxy)acetohydrazide: 2-(2-(furan-3-yl)-6-methylphenoxy)acetohydrazide (70 mg, 0.28 mmol) and 1H-indol-6-carbaldehyde (45 mg, 0.31 mmol) were dissolved in EtOH 2 mL, followed by stirring at 100° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:1) to obtain Compound 311 (70 mg, 67%).

$^1$H NMR (400 MHz, DMSO-$d_6$): δ 11.31 (m, 1H), 11.20 (m, 1H), 8.47-8.04 (2s, 1H), 7.71 (s, 0.5H), 7.58 (m, 1H), 7.58-7.38 (m, 3H), 7.27 (m, 0.5H), 7.17 (m, 1H), 7.06 (m, 2H), 6.45 (m, 1H), 4.81 (s, 1H), 4.04 (m, 1H), 3.97 (m, 2H), 3.78 (m, 2H), 3.52 (m, 1H), 2.29 (m, 3H), 2.29 (m, 1H), 1.19 (m, 1H).

EXAMPLE 64

Synthesis of Compound 312

2-(2-(furan-3-yl)-6-methylphenoxy)acetohydrazide (70 mg, 0.28 mmol) and 1H-indol-4-carbaldehyde (45 mg, 0.31 mmol) were dissolved in EtOH 2 mL, followed by stirring at 100° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:1) to obtain Compound 312 (70 mg, 67%).

$^1$H NMR (400 MHz, DMSO-$d_6$): δ 11.35 (m, 1H), 11.3 (m, 1H), 8.66-8.23 (2s, 1H), 7.46 (m, 2H), 7.25 (m, 0.5H), 7.16 (m, 5H), 6.77 (m, 0.5H), 4.90 (s, 1H), 4.40 (s, 1H), 4.03 (m, 1H), 3.77 (m, 2H), 3.54 (m, 1H), 3.34 (m, 1H), 2.29 (s, 3H), 2.29 (m, 1H), 1.89 (m, 1H).

EXAMPLE 65

Synthesis of Compound 313

Step 1. Synthesis of methyl 2-(2-(furan-3-yl)-6-methylphenoxy)acetate: 2-(furan-3-yl)-6-methylphenol (Compound 6-9)(100 mg, 0.57 mmol), methyl bromoacetate (0.04 mL, 0.68 mmol) and cesium carbonate (160 mg, 0.68 mmol) were dissolved in acetonitrile 4 mL, followed by stirring at room temperature for 12 hours. After the completion of the reaction, the reaction mixture was filtered under reduced pressure. The filtrate was concentrated under reduced pressure, and purified by column chromatography (ethyl acetate:hexane=1:3) to obtain methyl 2-(2-(furan-3-yl)-6-methylphenoxy)acetate (146 mg, 100%).

Step 2. Synthesis of 2-(2-(furan-3-yl)-6-methylphenoxy)acetohydrazide: methyl 2-(2-(furan-3-yl)-6-methylphenoxy)acetate (146 mg, 0.57 mmol) and hydrazine (0.03 mL, 0.6 mmol) were dissolved in EtOH 2 mL, followed by stirring at 100° C. for 6 hours. After the completion of the reaction, the reaction mixture was concentrated under reduced pressure to obtain 2-(2-(furan-3-yl)-6-methylphenoxy)aceto-hydrazide (121 mg, 83%).

Step 3. Synthesis of (E)-N'-((1H-indol-6-yl)methylene)-2-(2-(furan-3-yl)-6-methylphenoxy)acetohydrazide: 2-(2-(furan-3-yl)-6-methylphenoxy)acetohydrazide (70 mg, 0.28 mmol) and 1H-indol-6-carbaldehyde (45 mg, 0.31 mmol) were dissolved in EtOH 2 mL, followed by stirring at 100° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:1) to obtain Compound 313 (20 mg, 19%).

$^1$H NMR (400 MHz, DMSO-$d_6$): δ 11.41 (m, 2H), 8.45-8.01 (2s, 1H), 8.30 (m, 1H), 7.72 (m, 1H), 7.46 (m, 4H), 7.10 (m, 4H), 6.44 (m, 1H), 4.70 (s, 1H), 4.25 (s, 1H), 2.30 (m, 3H).

EXAMPLE 66

Synthesis of Compound 314

2-(2-(furan-3-yl)-6-methylphenoxy)acetohydrazide (70 mg, 0.28 mmol) and 1H-indol-4-carbaldehyde (45 mg, 0.31 mmol) were dissolved in EtOH 2 mL, followed by stirring at 100° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:1) to obtain Compound 314 (28 mg, 26%).

$^1$H NMR (400 MHz, DMSO-$d_6$): δ 11.44 (m, 1H), 11.34 (m, 1H), 8.64 (s, 1H), 8.18 (s, 1H), 8.32 (m, 1H), 7.75 (m, 1H), 7.47 (m, 3H), 7.27-7.00 (m, 5.5H), 6.57 (s, 0.5H), 4.78 (s, 1H), 4.29 (s, 1H), 2.37 (m, 3H).

EXAMPLE 67

Synthesis of Compound 317

Step 1. Synthesis of methyl 2-(2-(furan-2-yl)-4,6-dimethylphenoxy)acetate: 2-(furan-2-yl)-4,6-dimethylphenol (Compound 6-18) (133 mg, 0.71 mmol), methyl 2-bromoacetate (0.08 mL, 0.85 mmol) and cesium carbonate (276 mg, 0.85 mmol) were dissolved in acetonitrile 1 mL, followed by stirring at 100° C. for 1 hour. After the completion of the reaction, the reaction mixture was added with water, and extracted with ethyl acetate. The obtained organic layer was dried over magnesium sulfate, and purified by column chromatography (ethyl acetate:hexane=1:4) to obtain methyl 2-(2-(furan-2-yl)-4,6-dimethylphenoxy)acetate (168 mg, 100%).

Step 2. Synthesis of 2-(2-(furan-2-yl)-4,6-dimethylphenoxy)acetohydrazide: Methyl 2-(2-(furan-2-yl)-4,6-dimethylphenoxy)acetate (168 mg, 0.65 mmol) and hydrazine (0.03 mL, 0.72 mmol) were dissolved in EtOH 2 mL, followed by stirring at 100° C. for 12 hours. After the completion of the reaction, the reaction mixture was concentrated under reduced pressure to obtain 2-(2-(furan-2-yl)-4,6-dimethylphenoxy)acetohydrazide (169 mg, 100%).

Step 3. Synthesis of (E)-N'-((1H-indol-4-yl)methylene)-2-(2-(furan-2-yl)-4,6-dimethylphenoxy)acetohydrazide: 2-(2-(furan-2-yl)-4,6-dimethylphenoxy)acetohydrazide (85 mg, 0.33 mmol) and 1H-indol-4-carbaldehyde (52 mg, 0.36 mmol) were dissolved in EtOH 2 mL, followed by stirring at 100° C. for 24 hours. After the completion of the reaction, the formed solid was filtered to obtain Compound 317 (140 mg, 31%).

$^1$H NMR (400 MHz, DMSO-$d_6$): δ 11.57 (m, 1H), 11.46 (m, 1H), 8.64-8.24 (2s, 1H), 7.75 (m, 1H), 7.47 (m, 3H), 7.11 (m, 4.5H), 6.62 (m, 1.5H), 4.80 (s, 1H), 4.30 (s, 1H), 2.32 (m, 6H).

EXAMPLE 68

Synthesis of Compound 318

2-(2-(furan-2-yl)-4,6-dimethylphenoxy)acetohydrazide (85 mg, 0.33 mmol) and 1H-indol-6-carbaldehyde (52 mg, 0.36 mmol) were dissolved in EtOH 2 mL, followed by stirring at 90° C. for 24 hours. After the completion of the reaction, the reaction mixture was added with water, and extracted with ethyl acetate. The obtained organic layer was dried over magnesium sulfate, and purified by column chromatography (ethyl acetate:hexane=45:55) to obtain Compound 318 (30 mg, 23%).

$^1$H NMR (400 MHz, DMSO-$d_6$): δ 11.44 (m, 1H), 11.20 (m, 1H), 8.47-8.02 (2s, 1H), 7.73 (m, 1H), 7.44 (m, 4H), 7.23 (m, 0.5H), 7.14 (m, 1H), 7.02 (m, 1H), 6.60 (m, 1H), 6.43 (m, 1H), 4.72 (s, 1H), 4.44 (s, 1H), 2.32 (m, 6H).

EXAMPLE 69

Synthesis of Compound 319

2-(2-(furan-3-yl)pyridin-3-yloxy)acetohydrazide (70 mg, 0.30 mmol) and 1H-indol-4-carbaldehyde (48 mg, 0.33 mmol) were dissolved in EtOH 2 mL, followed by stirring at 80° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:1). The resultant was recrystallized with tetrahydrofuran/hexane, and filtered to obtain Compound 319 (50 mg, 46%).

$^1$H NMR (400 MHz, DMSO-$d_6$): δ 11.62 (m, 1H), 11.39 (m, 1H), 8.74-8.46 (m, 1H), 8.30 (s, 1H), 8.21 (m, 1H), 7.74 (m, 1H), 7.52 (m, 3H), 7.20 (m, 4H), 7.01 (m, 1H), 5.43 (s, 1H), 4.90 (s, 1H).

EXAMPLE 70

Synthesis of Compound 320

2-(2,4-dimethyl-6-(tetrahydrofuran-3-yl)phenoxy)acetohydrazide (40 mg, 0.15 mmol) and 1H-indol-4-carbaldehyde (22 mg, 0.15 mmol) were dissolved in EtOH 2 mL, followed by stirring at 90° C. for 4 hours. After the completion of the reaction, the reaction mixture was concentrated under reduced pressure, and purified by column chromatography (ethyl acetate:hexane=1:1) to obtain Compound 320 (17 mg, 29%).

$^1$H NMR (400 MHz, DMSO-$d_6$): δ 11.45 (bs, 1H), 11.35 (bs, 1H), 8.45 (s, 1H), 8.25-8.16 (2s, 1H), 7.45 (m, 2H), 7.25 (m, 3H), 7.17 (m, 1H), 7.11 (m, 1H), 6.96 (m, 1H), 5.49-4.94 (s, 2H), 4.01 (m, 2H), 3.77 (m, 2H), 3.51 (m, 1H), 2.28 (s, 3H), 2.22 (s, 3H).

EXAMPLE 71

Synthesis of Compound 322

Step 1. Synthesis of methyl 2-(4-(furan-3-yl)-2,6-dimethylphenoxy)acetate: 4-(furan-3-yl)-2,6-dimethylphenol (Compound 6-5) (120 mg, 0.46 mmol), methyl 2-bromoacetate (0.05 mL, 0.55 mmol) and cesium carbonate (448 mg, 1.39 mmol) were dissolved in acetonitrile 2 mL, followed by stirring at 90° C. for 3 hours. After the completion of the reaction, the reaction mixture was added with water, and extracted with ethyl acetate. The obtained organic layer was dried over magnesium sulfate, and purified by column chromatography (hexane:ethyl acetate=9:1) to obtain 2-(4-(furan-3-yl)-2,6-dimethylphenoxy)acetate (130 mg, 79%).

Step 2. Synthesis of 2-(4-(furan-3-yl)-2,6-dimethylphenoxy)acetohydrazide: 2-(4-(furan-3-yl)-2,6-dimethylphenoxy)acetate (125 mg, 0.48 mmol) and hydrazine (0.024 mL, 0.48 mmol) were dissolved in EtOH 2 mL, followed by stirring at 90° C. for 2 hours. After the completion of the reaction, the reaction mixture was filtered under reduced pressure, and added with diethyl ether 10 mL, followed by stirring for 10 minutes. The formed solid was filtered to obtain 2-(4-(furan-3-yl)-2,6-dimethylphenoxy)aceto-hydrazide (102 mg, 82%).

Step 3. Synthesis of (E)-N'-((1H-indol-6-yl)methylene)-2-(4-(furan-3-yl)-2,6-dimethylphenoxy)acetohydrazide: 2-(4-(furan-3-yl)-2,6-dimethylphenoxy)acetohydrazide (40 mg, 0.15 mmol) and 1H-indol-6-carbaldehyde (22 mg, 0.15 mmol) were dissolved in EtOH 2 mL, followed by stirring at 90° C. for 3 hours. After the completion of the reaction, the reaction mixture was concentrated under reduced pressure, and purified by column chromatography (hexane:ethyl acetate=1:1) to obtain Compound 322 (19 mg, 32%).

$^1$H NMR (400 MHz, DMSO-$d_6$): δ 11.41-11.38 (m, 1H), 11.30-11.20 (m, 1H), 8.50-8.04 (2s, 1H), 8.08 (m, 1H), 7.88 (m, 1H), 7.61 (m, 1H), 7.48-7.37 (m, 2H), 7.38 (m, 1H), 7.27 (m, 3H), 6.89 (m, 1H), 6.47 (m, 1H), 4.81 (s, 1H), 4.34 (s, 1H), 2.07 (m, 6H).

EXAMPLE 72

Synthesis of Compound 323

Step 1. Synthesis of methyl 2-(2,6-dimethyl-4-(tetrahydrofuran-3-yl)phenoxy)acetate: 2,6-dimethyl-4-(tetrahydrofuran-3-yl)phenol (Compound 7-6) (68 mg, 0.35 mmol), methyl 2-bromoacetate (0.04 mL, 0.45 mmol) and cesium carbonate (341 mg, 1.05 mmol) were dissolved in acetonitrile 2 mL, followed by stirring at 100° C. for 4 hours. After the completion of the reaction, the reaction mixture was filtered under reduced pressure. The filtrate was concentrated under reduced pressure, and purified by column chromatography (hexane:ethyl acetate=9:1) to obtain methyl 2-(2,6-dimethyl-4-(tetrahydro-furan-3-yl)phenoxy)acetate (74 mg, 79%).

Step 2. Synthesis of 2-(2,6-dimethyl-4-(tetrahydrofuran-3-yl)phenoxy)acetohydrazide: methyl 2-(2,6-dimethyl-4-(tetrahydrofuran-3-yl)phenoxy)acetate (67 mg, 0.25 mmol) and hydrazine (0.012 mL, 0.25 mmol) were dissolved in EtOH 2 mL, followed by stirring at 90° C. for 2 hours. After the completion of the reaction, the reaction mixture was concentrated under reduced pressure, added with diethyl ether 10 mL, and stirred for 10 minutes. The formed solid was filtered to obtain 2-(2,6-dimethyl-4-(tetrahydrofuran-3-yl)phenoxy)acetohydrazide (45 mg, 66%).

Step 3. Synthesis of (E)-N'-((1H-indol-6-yl)methylene)-2-(2,6-dimethyl-4-(tetrahydrofuran-3-yl)phenoxy)acetohydrazide: 2-(2,6-dimethyl-4-(tetrahydrofuran-3-yl)phenoxy) acetohydrazide (30 mg, 0.11 mmol) and 1H-indol-6-carbaldehyde (17 mg, 0.11 mmol) were dissolved in EtOH 1 mL, followed by stirring at 90° C. for 3 hours. After the completion of the reaction, the reaction mixture was concentrated under reduced pressure, and purified by column chromatography (hexane:ethyl acetate=1:1) to obtain Compound 323 (15 mg, 34%).

$^1$H NMR (400 MHz, DMSO-d$_6$): δ 11.42-11.39 (m, 1H), 11.37-11.32 (m, 1H), 8.47-8.03 (s, 1H), 7.57-7.48 (m, 2H), 7.40-7.37 (m, 2H), 6.95 (m, 2H), 6.47 (m, 1H), 4.74 (s, 1H), 4.31 (s, 1H), 3.96 (m, 3H), 3.75 (m, 2H), 2.32 (s, 3H), 2.21 (s, 3H).

EXAMPLE 73

Synthesis of Compound 326

Step 1. Synthesis of methyl 2-(2,3-dimethylphenoxy) acetate: 2,3-dimethylphenol (500 mg, 4.09 mmol), methyl 2-bromoacetate (0.45 mL, 4.90 mmol) and cesium carbonate (4.0 g, 12.3 mmol) were dissolved in acetonitrile 8 mL, followed by stirring at 100° C. for 3 hours. After the completion of the reaction, the reaction mixture was filtered under reduced pressure. The filtrate was concentrated under reduced pressure, and purified by column chromatography (hexane:ethyl acetate=9:1) to obtain methyl 2-(2,3-dimethylphenoxy)acetate (628 mg, 83%).

Step 2. Synthesis of 2-(2,3-dimethylphenoxy)acetohydrazide: methyl 2-(2,3-dimethylphenoxy)acetate (600 mg, 3.09 mmol) and hydrazine (0.15 mL, 3.09 mmol) were dissolved in EtOH 8 mL, followed by stirring at 90° C. for 2 hours. After the completion of the reaction, the reaction mixture was concentrated under reduced pressure, added with diethyl ether 10 mL, and stirred for 10 minutes. The formed solid was filtered to obtain 2-(2,3-dimethylphenoxy) acetohydrazide (572 mg, 95%).

Step 3. Synthesis of (E)-N'-((1H-indol-4-yl)methylene)-2-(2,3-dimethylphenoxy)acetohydrazide: 2-(2,3-dimethylphenoxy)acetohydrazide (100 mg, 0.55 mmol) and 1H-indol-4-carbaldehyde (75 mg, 0.52 mmol) were dissolved in EtOH 3 mL, followed by stirring at 90° C. for 2 hours. After the completion of the reaction, the reaction mixture was concentrated under reduced pressure, and purified by column chromatography (hexane:ethyl acetate=1:1) to obtain Compound 326 (93 mg, 56%).

$^1$H NMR (400 MHz, DMSO-d$_6$): δ 11.50-11.44 (m, 1H), 11.37-11.32 (m, 1H), 8.52-8.25 (2s, 1H), 7.50 (m, 2H), 7.23 (m, 2H), 7.06 (m, 2H), 6.81 (m, 1H), 6.75 (m, 1H), 5.18 (s, 1H), 4.65 (s, 1H), 2.23 (s, 3H), 2.21 (s, 3H).

EXAMPLE 74

Synthesis of Compound 327

2-(2,3-dimethylphenoxy)acetohydrazide (100 mg, 0.55 mmol) and 1H-indol-4-carbaldehyde (75 mg, 0.52 mmol) were dissolved in EtOH 3 mL, followed by stirring at 90° C. for 2 hours. After the completion of the reaction, the reaction mixture was concentrated under reduced pressure, and purified by column chromatography (hexane:ethyl acetate=1:1) to obtain Compound 327 (104 mg, 62%).

$^1$H NMR (400 MHz, DMSO-d$_6$): δ 11.41 (bs, 1H), 11.27 (bs, 1H), 8.34-8.07, (2s, 1H), 7.69 (d, J=22.9 Hz, 1H), 7.56 (m, 1H), 7.41 (m, 2H), 6.98 (m, 1H), 6.70 (m, 2H), 6.46 (m, 1H), 4.82 (d, 2H), 2.49 (s, 3H), 2.23 (s, 3H).

EXAMPLE 75

Synthesis of Compound 329

2-(2-ethyl-6-methylpyridin-3-yloxy)acetohydrazide (30 mg, 0.14 mmol) and 1H-indol-4-carbaldehyde (21 mg, 0.37 mmol) were dissolved in EtOH 1 mL, followed by stirring at 90° C. for 4 hours. After the completion of the reaction, the formed solid was filtered to obtain Compound 329 (19 mg, 40%).

$^1$H NMR (400 MHz, DMSO-d$_6$): δ 11.52 (bs, 1H), 11.37 (bs, 1H), 8.49-8.25 (2s, 1H), 7.48 (m, 2H), 7.17 (m, 3H), 6.98 (m, 2H), 5.23 (s, 1H), 4.70 (s, 1H), 2.78 (m, 2H), 2.35 (s, 3H), 1.18 (m, 3H).

EXAMPLE 76

Synthesis of Compound 330

Step 1. Synthesis of methyl 2-(4-bromo-2-cyanophenoxy) acetate: 5-bromo-2-hydroxybenzonitrile (400 mg, 2.01 mmol), methyl 2-bromoacetate (0.2 mL, 2.2 mmol) and cesium carbonate (716 mg, 2.2 mmol) were dissolved in acetonitrile 4 mL, followed by stirring at 80° C. for 2 hours. After the completion of the reaction, the reaction mixture was filtered under reduced pressure. The filtrate was concentrated under reduced pressure, and purified by column chromatography (ethyl acetate:hexane=1:3) to obtain methyl 2-(4-bromo-2-cyanophenoxy)acetate (451 mg, 83%).

Step 2. Synthesis of 2-(4-bromo-2-cyanophenoxy)acetohydrazide: methyl 2-(4-bromo-2-cyanophenoxy)acetate (451 mg, 1.67 mmol) and hydrazine (0.09 mL, 1.84 mmol) were dissolved in EtOH 2 mL, followed by stirring at 100° C. for 12 hours. After the completion of the reaction, the formed solid was filtered to obtain 2-(4-bromo-2-cyanophenoxy)acetohydrazide (398 mg, 88%).

Step 3. Synthesis of (E)-N'-((1H-indol-4-yl)methylene)-2-(4-bromo-2-cyanophenoxy)acetohydrazide: 2-(4-bromo-2-cyanophenoxy)acetohydrazide (100 mg, 0.37 mmol) and 1H-indol-4-carbaldehyde (53 mg, 0.39 mmol) were dissolved in EtOH 2 mL, followed by stirring at 90° C. for 12 hours. After the completion of the reaction, the reaction mixture was added with water, and extracted with ethyl acetate. The obtained organic layer was dried over magnesium sulfate, and purified by column chromatography (ethyl acetate:hexane=2:1) to obtain Compound 330 (21 mg, 0.05 mmol, 14%).

$^1$H NMR (400 MHz, DMSO-d$_6$): δ 11.6 (bs, 1H), 11.37 (m, 1H), 8.45-8.26 (2s, 1H), 8.03 (m, 1H), 7.78 (m, 1H), 7.47 (m, 2H), 7.16 (m, 3H), 6.98 (m, 1H), 5.47 (s, 1H), 4.93 (s, 1H).

EXAMPLE 77

Synthesis of Compound 331

Step 1. Synthesis of methyl 2-(2-(pyrrolidin-1-yl)pyridin-3-yloxy)acetate: 2-(pyrrolidin-1-yl)pyridin-3-ol (Compound 7-9) (78 mg, 0.41 mmol), methyl bromoacetate (0.05 mL, 0.49 mmol) and cesium carbonate (159 mg, 0.49 mmol) were dissolved in acetonitrile 2 mL, followed by stirring at 80° C. for 3 hours. After the completion of the reaction, the reaction mixture was filtered under reduced pressure. The filtrate was concentrated under reduced pressure, and purified by column chromatography (ethyl acetate:hexane=1:5) to obtain methyl 2-(2-(pyrrolidin-1-yl)pyridin-3-yloxy)acetate (86 mg, 88%).

Step 2. Synthesis of 2-(2-(pyrrolidin-1-yl)pyridin-3-yloxy)acetohydrazide: methyl 2-(2-(pyrrolidin-1-yl)pyridin-3-yloxy)acetate (86 mg, 0.36 mmol) and hydrazine (0.02 mL, 0.39 mmol) were dissolved in EtOH 2 mL, followed by stirring at 100° C. for 12 hours. After the completion of the reaction, the reaction mixture was concentrated under reduced pressure to obtain 2-(2-(pyrrolidin-1-yl)pyridin-3-yloxy)aceto-hydrazide (85 mg, 99%).

Step 3. Synthesis of (E)-N'-((1H-indol-6-yl)methylene)-2-(2-(pyrrolidin-1-yl)pyridin-3-yloxy)acetohydrazide: 2-(2-(pyrrolidin-1-yl)pyridin-3-yloxy)acetohydrazide (85 mg, 0.36 mmol) and 1H-indol-6-carbaldehyde (57 mg, 0.39 mmol) were dissolved in EtOH 2 mL, followed by stirring at 100° C. for 12 hours. After the completion of the reaction, the reaction mixture was extracted with ethyl acetate, dried over magnesium sulfate, and purified by column chromatography (ethyl acetate:hexane=1:1) to obtain Compound 331 (64 mg, 48%).

$^1$H NMR (400 MHz, DMSO-$d_6$): δ 11.44 (m, 1H), 11.27 (m, 1H), 8.32-8.07 (2s, 1H), 7.69 (m, 2H), 7.56 (m, 1H), 7.43 (m, 2H), 7.06 (m, 1H), 6.55 (m, 1H), 6.46 (m, 1H), 5.09 (s, 1H), 4.59 (s, 1H), 3.59 (m, 4H), 1.82 (m, 4H).

EXAMPLE 78

Synthesis of Compound 332

Step 1. Synthesis of methyl 2-(2,4-dimethyl-6-(tetrahydrofuran-2-yl)phenoxy)acetate: 2,4-dimethyl-6-(tetrahydrofuran-2-yl)phenol (Compound 7-5) (200 mg, 1.04 mmol), methyl 2-bromoacetate (0.095 mL, 1.14 mmol) and cesium carbonate (327 mg, 1.14 mmol) were dissolved in acetonitrile 2 mL, followed by stirring at 100° C. for 3 hours. After the completion of the reaction, the reaction mixture was filtered under reduced pressure. The filtrate was concentrated under reduced pressure, and purified by column chromatography (ethyl acetate:hexane=1:3) to obtain methyl 2-(2,4-dimethyl-6-(tetrahydrofuran-2-yl)phenoxy)acetate (145 mg, 0.73 mmol, 30%).

Step 2. Synthesis of 2-(2,4-dimethyl-6-(tetrahydrofuran-2-yl)phenoxy)acetohydrazide: methyl 2-(2,4-dimethyl-6-(tetrahydrofuran-2-yl)phenoxy)acetate (80 mg, 0.30 mmol) and hydrazine (0.02 mL, 0.33 mmol) were dissolved in EtOH 2 mL, followed by stirring at 100° C. for 6 hours. After the completion of the reaction, the reaction mixture was concentrated under reduced pressure to obtain 2-(2,4-dimethyl-6-(tetrahydro-furan-2-yl)phenoxy)acetohydrazide (80 mg, 100%).

Step 3. Synthesis of (E)-N'-((1H-indol-6-yl)methylene)-2-(2,4-dimethyl-6-(tetrahydrofuran-2-yl)phenoxy)acetohydrazide: 2-(2,4-dimethyl-6-(tetrahydrofuran-2-yl)phenoxy)acetohydrazide (80 mg, 0.30 mmol) and 1H-indol-6-carbaldehyde (43 mg, 0.32 mmol) were dissolved in EtOH 2 mL, followed by stirring at 100° C. for 12 hours. After the completion of the reaction, the reaction mixture was added with water, and extracted with ethyl acetate. The obtained organic layer was dried over magnesium sulfate, and purified by column chromatography (ethyl acetate:hexane=1:1) to obtain Compound 332 (60 mg, 51%).

$^1$H NMR (400 MHz, DMSO-$d_6$): δ 11.36 (m, 1H), 11.2 (m, 1H), 8.48-8.03 (2s, 1H), 7.70 (s, 0.5H), 7.50 (m, 4H), 7.39 (m, 0.5H), 6.85 (m, 2H), 6.47 (m, 1H), 4.74-4.31 (2s, 1H), 4.31 (m, 1H), 3.38 (m, 2H), 2.22 (m, 6H), 1.58 (m, 2H), 1.45 (m, 2H).

EXAMPLE 79

Synthesis of Compound 333

2-(2-(furan-3-yl)-4,6-dimethylphenoxy)acetohydrazide (30 mg, 0.12 mmol) and 1H-indol-4-carbaldehyde (17 mg, 0.12 mmol) were dissolved in EtOH 2 mL, followed by stirring at 90° C. for 6 hours. After the completion of the reaction, the formed solid was filtered to obtain Compound 333 (14 mg, 31%).

$^1$H NMR (400 MHz, DMSO-$d_6$): δ 11.48-11.43 (m, 1H), 11.34 (s, 1H), 8.43 (d, J=10.6 Hz, 1H), 8.64-8.27 (2s, 1H), 7.72 (m, 1H), 7.48 (m, 2H), 7.39 (m, 1H), 7.24 (m, 2H), 7.01 (m, 1H), 6.98 (m, 1H), 4.74 (s, 1H), 4.23 (s, 1H), 2.27 (s, 3H), 2.24 (s, 3H).

EXAMPLE 80

Synthesis of Compound 336

2-(4-(furan-3-yl)-2,6-dimethylphenoxy)acetohydrazide (30 mg, 0.11 mmol) and 1H-indol-4-carbaldehyde (17 mg, 0.15 mmol) were dissolved in EtOH 1 mL, followed by stirring at 90° C. for 10 hours. After the completion of the reaction, the reaction mixture was concentrated under reduced pressure, and purified by column chromatography (hexane:ethyl acetate=1:1) to obtain Compound 336 (18 mg, 41%).

$^1$H NMR (400 MHz, DMSO-$d_6$): δ 11.51 (bs, 1H), 11.35 (s, 1H), 8.35-8.27 (2s, 1H), 8.08 (m, 1H), 7.50 (m, 1H), 7.46 (m, 1H), 7.32 (m, 1H), 7.24 (m, 2H), 7.05 (m, 1H), 6.90 (m, 1H), 5.04 (s, 1H), 4.77 (s, 1H), 2.31 (d, J=16.0 Hz, 3H), 2.16 (s, 3H).

EXAMPLE 81

Synthesis of Compound 337

2-(2,6-dimethyl-4-(tetrahydrofuran-3-yl)phenoxy)acetohydrazide (50 mg, 0.19 mmol) and 1H-indol-4-carbaldehyde (100 mg, 0.55 mmol) were dissolved in EtOH 1 mL, followed by stirring at 90° C. for 3 hours. After the completion of the reaction, the reaction mixture was added with water, and extracted with ethyl acetate. The obtained organic layer was dried over magnesium sulfate, and purified by column chromatography (hexane:ethyl acetate=1:1) to obtain Compound 337 (31 mg, 50%).

$^1$H NMR (400 MHz, DMSO-$d_6$): δ 11.42 (bs, 1H), 11.29 (m, 1H), 8.55-8.16 (2s, 1H), 7.58 (m, 2H), 7.40 (m, 2H), 6.95 (m, 2H), 6.47 (m, 1H), 5.26 (s, 1H), 4.73 (s, 1H), 3.96 (m, 3H), 3.75 (m, 2H), 2.32 (s, 3H), 2.21 (s, 3H).

EXAMPLE 82

Synthesis of Compound 343

Step 1. Synthesis of methyl 2-(2-(thiophene-3-yl)pyridin-3-yloxy)acetate: 2-(thiophene-3-yl)pyridin-3-ol (Compound 6-12) (50 mg, 0.28 mmol), methyl 2-bromoacetate (0.03 mL, 0.31 mmol) and cesium carbonate (101 mg, 0.31 mmol) were dissolved in acetonitrile 1mL, followed by stirring at 80° C. for 3 hours. After the completion of the reaction, the reaction mixture was added with water, and extracted with ethyl acetate. The obtained organic layer was dried over magnesium sulfate, and purified by column chromatography (ethyl acetate:hexane=1:1) to obtain methyl 2-(2-(thiophene-3-yl)pyridin-3-yloxy)acetate (48 mg, 67%).

Step 2. Synthesis of 2-(2-(thiophene-3-yl)pyridin-3-yloxy)acetohydrazide: methyl 2-(2-(thiophene-3-yl)pyridin-3-yloxy)acetate (48 mg, 0.19 mmol) and hydrazine (0.01 mL, 0.21 mmol) were dissolved in EtOH 2 mL, followed by stirring at 90° C. for 12 hours. After the completion of the reaction, the reaction mixture was concentrated under reduced pressure to obtain 2-(2-(thiophene-3-yl)pyridin-3-yloxy)-acetohydrazide (48 mg, 100%).

Step 3. Synthesis of (E)-N'-((1H-indol-6-yl)methylene)-2-(2-(thiophene-3-yl)pyridin-3-yloxy)acetohydrazide: 2-(2-(thiophene-3-yl)pyridin-3-yloxy)acetohydrazide (48 mg, 0.19 mmol) and 1H-indol-6-carbaldehyde (30 mg, 0.21 mmol) were dissolved in EtOH 2 mL, followed by stirring at 85° C. for 12 hours. After the completion of the reaction, the reaction mixture was concentrated under reduced pressure, and purified by column chromatography (ethyl acetate:hexane=1:1) to obtain Compound 343 (31 mg, 42%).

$^1$H NMR (400 MHz, DMSO-$d_6$): δ 11.50 (m, 1H), 11.30 (m, 1H), 8.62-8.50 (m, 1H), 8.29-8.21 (m, 1H), 8.11 (s, 1H), 7.98 (m, 1H), 7.67 (m, 1H), 7.57 (m, 3H), 7.45 (m, 2H), 7.29 (m, 1H), 6.47 (m, 1H), 5.37 (s, 1H), 4.86 (s, 1H).

EXAMPLE 83

Synthesis of Compound 344

Step 1. Synthesis of methyl 2-(2,4-dimethyl-6-(thiophene-2-yl)phenoxy)acetate: 2,4-dimethyl-6-(thiophene-2-yl)phenol (Compound 6-13) (100 mg, 0.49 mmol), methyl 2-bromoacetate (0.05 mL, 0.53 mmol) and cesium carbonate (190 mg, 0.53 mmol) were dissolved in acetonitrile 1 mL, followed by stirring at 100° C. for 1 hour. After the completion of the reaction, the reaction mixture was filtered under reduced pressure. The filtrate was concentrated under reduced pressure, and purified by column chromatography (ethyl acetate:hexane=1:4) to obtain methyl 2-(2,4-dimethyl-6-(thiophene-2-yl)phenoxy)acetate (141 mg, 100%).

Step 2. Synthesis of 2-(2,4-dimethyl-6-(thiophene-2-yl)phenoxy)acetohydrazide: Methyl 2-(2,4-dimethyl-6-(thiophene-2-yl)phenoxy)acetate (141 mg, 0.51 mmol) and hydrazine (0.03 mL, 0.56 mmol) were dissolved in EtOH 2 mL, followed by stirring at 85° C. for 12 hours. After the completion of the reaction, the reaction mixture was concentrated under reduced pressure to obtain 2-(2,4-dimethyl-6-(thiophene-2-yl)-phenoxy)acetohydrazide (128 mg, 91%).

Step 3. Synthesis of (E)-N'-((1H-indol-4-yl)methylene)-2-(2,4-dimethyl-6-(thiophene-2-yl)phenoxy)acetohydrazide: 2-(2,4-dimethyl-6-(thiophene-2-yl)phenoxy)acetohydrazide (70 mg, 0.25 mmol) and 1H-indol-4-carbaldehyde (40 mg, 0.26 mmol) were dissolved in EtOH 2 mL, followed by stirring at 100° C. for 12 hours. After the completion of the reaction, the reaction mixture was concentrated under reduced pressure, and purified by column chromatography (ethyl acetate:hexane=1:1) to obtain Compound 344 (31 mg, 31%).

$^1$H NMR (400 MHz, DMSO-$d_6$): δ 11.42 (bs, 0.5H), 11.35 (m, 1.5H), 8.68 (s, 1H), 8.15 (s, 0.5H), 7.61-7.59 (m, 2H), 7.35-7.05 (m, 7H), 6.49 (m, 0.5H), 4.72 (s, 1H), 4.25 (s, 1H), 2.28 (m, 6H).

EXAMPLE 84

Synthesis of Compound 345

2-(2,4-dimethyl-6-(thiophene-2-yl)phenoxy)acetohydrazide (70 mg, 0.25 mmol) and 1H-indol-6-carbaldehyde (40 mg, 0.26 mmol) were dissolved in EtOH 2 mL, followed by stirring at 100° C. for 12 hours. After the completion of the reaction, the reaction mixture was concentrated under reduced pressure, and purified by column chromatography (ethyl acetate:hexane=1:1) to obtain Compound 345 (20 mg, 20%).

$^1$H NMR (400 MHz, DMSO-$d_6$): δ 11.35 (m, 1H), 11.20 (m, 1H), 8.49-7.97 (2s, 1H), 7.71 (s, 1H), 7.61-7.34 (m, 6.5H), 7.16-7.09 (m, 1H), 7.02 (m, 1H), 6.44 (m, 1H), 4.65-4.20 (2s, 1H), 2.19 (m, 6H).

EXAMPLE 85

Synthesis of Compound 346

Step 1. Synthesis of methyl 2-(2-(furan-2-yl)-4-methoxyphenoxy)acetate: 2-(furan-2-yl)-4-methoxyphenol (Compound 6-14) (205 mg, 1.09 mmol), methyl 2-bromoacetate (0.1 mL, 1.08 mmol) and cesium carbonate (1.05 g, 3.24 mmol) were dissolved in acetonitrile 4 mL, followed by stirring at 90° C. for 9 hours. After the completion of the reaction, the reaction mixture was filtered under reduced pressure. The filtrate was concentrated under reduced pressure, and purified by column chromatography (hexane:ethyl acetate=9:1) to obtain methyl 2-(2-(furan-2-yl)-4-methoxyphenoxy)acetate (194 mg, 68%).

Step 2. Synthesis of 2-(2-(furan-2-yl)-4-methoxyphenoxy)acetohydrazide: methyl 2-(2-(furan-2-yl)-4-methoxyphenoxy)acetate (189 mg, 0.72 mmol) and hydrazine (0.035 mL, 0.72 mmol) were dissolved in EtOH 2 mL, followed by stirring at 90° C. for 3 hours. After the completion of the reaction, the reaction mixture was concentrated under reduced pressure, added with diethyl ether 10 mL, and stirred for 10 minutes. The formed solid was filtered to obtain 2-(2-(furan-2-yl)-4-methoxyphenoxy)aceto-hydrazide (146 mg, 80%).

Step 3. Synthesis of (E)-N'-((1H-indol-4-yl)methylene)-2-(2-(furan-2-yl)-4-methoxyphenoxy)acetohydrazide: 2-(2-(furan-2-yl)-4-methoxyphenoxy)acetohydrazide (50 mg, 0.19 mmol) and 1H-indol-4-carbaldehyde (28 mg, 0.19 mmol) were dissolved in EtOH 1 mL, followed by stirring at 90° C. for 4 hours. After the completion of the reaction, the reaction mixture was concentrated under reduced pressure, and purified by column chromatography (hexane:ethyl acetate=1:1) to obtain Compound 346 (21 mg, 28%).

$^1$H NMR (400 MHz, DMSO-$d_6$): δ 11.57-11.54 (m, 1H), 11.34-11.28 (m, 1H), 8.27-7.75 (2s, 1H), 7.74 (m, 1H), 7.30 (m, 3H), 7.17 (m, 5H), 6.98 (m, 1H), 6.61 (m, 1H), 5.26 (s, 1H), 4.73 (s, 1H), 3.76 (s, 3H).

EXAMPLE 86

Synthesis of Compound 347

2-(2-(furan-2-yl)-4-methoxyphenoxy)acetohydrazide (50 mg, 0.19 mmol) and 1H-indol-6-carbaldehyde (28 mg, 0.19 mmol) were dissolved in EtOH 1 mL, followed by stirring at 90° C. for 4 hours. After the completion of the reaction, the reaction mixture was concentrated under reduced pressure, and purified by column chromatography (hexane:ethyl acetate=1:1) to obtain Compound 347 (39 mg, 53%).

$^1$H NMR (400 MHz, DMSO-$d_6$): δ 11.50-11.47 (m, 1H), 11.32-11.28 (m, 1H), 8.30-8.09 (2s, 1H), 7.75 (m, 2H), 7.65 (m, 1H), 7.31 (m, 4H), 7.06 (m, 1H), 6.87 (m, 1H), 6.60 (s, 1H), 6.46 (s, 1H), 5.20 (s, 1H), 4.70 (s, 1H), 3.76 (s, 3H).

EXAMPLE 87

Synthesis of Compound 356

Step 1. Synthesis of methyl 2-(3-(furan-2-yl)phenoxy)acetate: 3-(furan-2-yl)phenol (Compound 6-15) (183 mg, 1.14 mmol), methyl 2-bromoacetate (0.11 mL, 1.14 mmol) and cesium carbonate (556 mg, 1.71 mmol) were dissolved in acetonitrile 2 mL, followed by stirring at 90° C. for 4 hours. After the completion of the reaction, the reaction mixture was filtered under reduced pressure. The filtrate was concentrated under reduced pressure, and purified by column chromatography (hexane:ethyl acetate=9:1) to obtain methyl 2-(3-(furan-2-yl)phenoxy)acetate (228 mg, 86%).

Step 2. Synthesis of 2-(3-(furan-2-yl)phenoxy)acetohydrazide: methyl 2-(3-(furan-2-yl)phenoxy)acetate (220 mg, 0.95 mmol) and hydrazine (0.05 mL, 0.95 mmol) were dissolved in EtOH 2 mL, followed by stirring at 90° C. for 2 hours. After the completion of the reaction, the reaction mixture was concentrated under reduced pressure, added with diethyl ether 10 mL, and stirred for 10 minutes. The formed solid was filtered to obtain 2-(3-(furan-2-yl)phenoxy)acetohydrazide (185 mg, 84%).

Step 3. Synthesis of (E)-N'-((1H-indol-4-yl)methylene)-2-(3-(furan-2-yl)phenoxy)acetohydrazide: 2-(3-(furan-2-yl)phenoxy)acetohydrazide (50 mg, 0.21 mmol) and 1H-indol-4-carbaldehyde (32 mg, 0.21 mmol) were dissolved in EtOH 1 mL, followed by stirring at 90° C. for 17 hours. After the completion of the reaction, the reaction mixture was concentrated under reduced pressure, and purified by column chromatography (hexane:ethyl acetate=1:1) to obtain Compound 356 (47 mg, 61%).

$^1$H NMR (400 MHz, DMSO-$d_6$): δ 11.54-11.49 (m, 1H), 11.41-11.38 (m, 1H), 8.58-8.27 (2s, 1H), 7.75 (m, 1H), 7.49 (m, 2H), 7.46 (m, 3H), 7.30 (m, 3H), 7.23 (m, 1H), 6.98 (m, 1H), 6.94 (m, 1H), 6.57 (m, 1H), 5.26 (s, 1H), 4.74 (s, 1H).

EXAMPLE 88

Synthesis of Compound 358

Step 1. Synthesis of methyl 2-(3-(pyridin-3-yl)phenoxy)acetate: 3-(pyridin-3-yl)phenol (Compound 6-16) (379 mg, 2.22 mmol), methyl 2-bromoacetate (0.2 mL, 2.22 mmol) and cesium carbonate (1086 mg, 3.33 mmol) were dissolved in acetonitrile 5 mL, followed by stirring at 100° C. for 4 hours. After the completion of the reaction, the reaction mixture was filtered under reduced pressure. The filtrate was concentrated under reduced pressure, and purified by column chromatography (hexane:ethyl acetate=7:3) to obtain methyl 2-(3-(pyridin-3-yl)phenoxy)acetate (420 mg, 78%).

Step 2. Synthesis of 2-(3-(pyridin-3-yl)phenoxy)acetohydrazide: methyl 2-(3-(pyridin-3-yl)phenoxy)acetate (410 mg, 1.69 mmol) and hydrazine (0.08 mL, 1.69 mmol) were dissolved in EtOH 4 mL, followed by stirring at 90° C. for 2 hours. After the completion of the reaction, the reaction mixture was concentrated under reduced pressure, added with diethyl ether 10 mL, and stirred for 10 minutes. The formed solid was filtered to obtain 2-(3-(pyridin-3-yl)phenoxy)acetohydrazide (365 mg, 89%).

Step 3. Synthesis of (E)-N'-((1H-indol-4-yl)methylene)-2-(3-(pyridin-3-yl)phenoxy)acetohydrazide: 2-(3-(pyridin-3-yl)phenoxy)acetohydrazide (50 mg, 0.20 mmol) and 1H-indol-4-carbaldehyde (30 mg, 0.20 mmol) were dissolved in EtOH 1 mL, followed by stirring at 90° C. for 17 hours. After the completion of the reaction, the formed solid was filtered to obtain Compound 358 (39 mg, 53%).

$^1$H NMR (400 MHz, DMSO-$d_6$): δ 11.53 (bs, 1H), 11.39-11.34 (m, 1H), 8.90 (m, 1H), 8.58 (m, 1H), 8.57-8.26 (2s, 1H), 8.05 (m, 1H), 7.39 (m, 6H), 7.13 (m, 3H), 6.99 (m, 1H), 5.32 (s, 1H), 4.80 (s, 1H).

EXAMPLE 89

Synthesis of Compound 359

2-(3-(pyridin-3-yl)phenoxy)acetohydrazide (50 mg, 0.21 mmol) and 1H-indol-6-carbaldehyde (32 mg, 0.21 mmol) were dissolved in EtOH 1 mL, followed by stirring at 90° C. for 17 hours. After the completion of the reaction, the reaction mixture was concentrated under reduced pressure, and purified by column chromatography (hexane:ethyl acetate=1:1) to obtain Compound 359 (28 mg, 38%).

$^1$H NMR (400 MHz, DMSO-$d_6$): δ 11.45-11.42 (m, 1H), 11.33-11.28 (m, 1H), 8.91 (m, 1H), 8.88 (m, 1H), 8.56-8.23 (s, 1H), 8.09 (m, 1H), 7.66 (m, 1H), 7.56 (m, 1H), 7.39 (m, 6H), 7.05 (m, 1H), 6.46 (m, 1H), 5.26 (s, 1H), 4.76 (s, 1H).

EXAMPLE 90

Synthesis of Compound 378

Step 1. Synthesis of methyl 2-(4-fluoro-2-methyl-6-(tetrahydrofuran-3-yl)phenoxy)acetate: 4-fluoro-2-methyl-6-(tetrahydrofuran-3-yl)phenol (Compound 7-4) (368 mg, 1.87 mmol) and methyl bromoacetate (0.21 mL, 2.25 mmol) were dissolved in acetonitrile. Cesium carbonate (915 mg, 2.81 mmol) was added thereto, followed by stirring at room temperature for 1 day. After the completion of the reaction, the reaction mixture was added with a saturated sodium hydrogen carbonate aqueous solution, and extracted with ethyl acetate. The obtained organic layer was washed with brine, dried over sodium sulfate anhydrous, filtered, and concentrated under reduced pressure. The residue was purified by column chromatography (silica gel; hexane/ethyl acetate, 9/1) to obtain methyl 2-(4-fluoro-2-methyl-6-(tetrahydrofuran-3-yl)phenoxy)acetate (415 mg, 83%).

Step 2. Synthesis of 2-(4-fluoro-2-methyl-6-(tetrahydrofuran-3-yl)phenoxy)acetohydrazide: methyl 2-(4-fluoro-2-methyl-6-(tetrahydrofuran-3-yl)phenoxy)acetate (415 mg, 1.55 mmol) and hydrazine monohydrate (91.0 μL, 3.93 mmol) were dissolved in ethanol, followed by stirring for 1 day under reflux. After the completion of the reaction, the reaction mixture was concentrated under reduced pressure. The concentrated residue was purified by column chromatography (silica gel; dichloromethane/methanol, 9/1) to obtain 2-(4-fluoro-2-methyl-6-(tetrahydrofuran-3-yl)phenoxy)acetohydrazide (316 mg, 76%) as a colorless oil.

Step 3. Synthesis of (E)-N'-((1H-indol-6-yl)methylene)-2-(4-fluoro-2-methyl-6-(tetrahydrofuran-3-yl)phenoxy)acetohydrazide: 2-(4-fluoro-2-methyl-6-(tetrahydrofuran-3-yl)phenoxy)acetohydrazide (230 mg, 0.86 mmol) and indol-6-carboxaldehyde (137 mg, 0.94 mmol) were dissolved in ethanol, followed by stirring overnight under reflux. After the completion of the reaction, the reaction mixture was concentrated under reduced pressure, and purified by column chromatography (silica gel; ethyl acetate:hexane, 3/7) to obtain Compound 378 (145 mg, 45%) as a white solid.

$^1$H NMR (400 MHz, DMSO-$d_6$): δ 11.48-11.44 (m, 1H), 11.35-11.23 (m, 1H), 8.48, 8.05 (2s, 1H), 7.72 (s, 0.5H), 7.59-7.27 (m, 3.5H), 6.96-6.88 (m, 2H), 6.47-6.43 (m, 1H), 4.77 (s, 1H), 4.34 (s, 3H), 4.02-3.92 (m, 2H), 3.77-3.73 (m, 2H), 3.53-3.43 (m, 2H), 2.26-2.20 (m, 7H), 1.89-2.20 (m, 1H).

EXAMPLE 91

Synthesis of Compound 379

2-(4-fluoro-2-methyl-6-(tetrahydrofuran-3-yl)phenoxy)acetohydrazide (80.5 mg, 0.30 mmol) and indol-4-carboxaldehyde (52.3 mg, 0.36 mmol) were dissolved in ethanol, followed by stirring for 1 day under reflux. After the completion of the reaction, the reaction mixture was concentrated under reduced pressure, and purified by column chromatography (silica gel; ethyl acetate:hexane, 3/7) to obtain Compound 379 (42 mg, 36%) as a white solid.

$^1$H NMR (400 MHz, DMSO-$d_6$): δ 11.48-11.44 (m, 1H), 11.35-11.23 (m, 1H), 8.48, 8.05 (2s, 1H), 7.72 (s, 0.5H), 7.59-7.27 (m, 3.5H), 6.96-6.88 (m, 2H), 6.47-6.41 (m, 1H), 4.75 (s, 1H), 4.31 (s, 3H), 4.02-3.92 (m, 2H), 3.75-3.71 (m, 2H), 3.53-3.43 (m, 2H), 2.26-2.21 (m, 7H), 1.88-2.22 (m, 1H).

EXAMPLE 92

Synthesis of Compound 457

Step 1. Synthesis of methyl 2-(2,4-dimethyl-6-(tetrahydro-2H-pyran-4-yl)phenoxy)acetate: 2,4-dimethyl-6-(tetrahydro-2H-pyran-4-yl)phenol (Compound 7-7) (156 mg, 0.76 mmol) and methyl bromoacetate (0.089 mL, 0.91 mmol) were dissolved in acetonitrile. Cesium carbonate (370 mg, 1.14 mmol) was added thereto, followed by stirring at room temperature for 1 day. After the completion of the reaction, the reaction mixture was added with a saturated sodium hydrogen carbonate aqueous solution, and extracted with ethyl acetate. The obtained organic layer was washed with brine, dried over sodium sulfate anhydrous, filtered, and concentrated under reduced pressure. The residue was purified by column chromatography (silica gel; hexane/ethyl acetate, 9/1) to obtain methyl 2-(2,4-dimethyl-6-(tetrahydro-2H-pyran-4-yl)phenoxy)acetate (168 mg, 80%).

Step 2. Synthesis of 2-(2,4-dimethyl-6-(tetrahydro-2H-pyran-4-yl)phenoxy)acetohydrazide: Methyl 2-(2,4-dimethyl-6-(tetrahydro-2H-pyran-4-yl)phenoxy)acetate (168 mg, 0.60 mmol) and hydrazine monohydrate (36.0 jL, 0.72 mmol) were dissolved in methanol, followed by stirring for 1 day under reflux. After the completion of the reaction, the reaction mixture was concentrated under reduced pressure. Hexane was added to the concentrate. The resulting white precipitate was filtered, and dried to obtain 2-(2,4-dimethyl-6-(tetrahydro-2H-pyran-4-yl)phenoxy)acetohydrazide (114 mg, 68%) as a white solid.

Step 3. Synthesis of (E)-N'-((1H-indol-6-yl)methylene)-2-(2,4-dimethyl-6-(tetrahydro-2H-pyran-4-yl)phenoxy)acetohydrazide: 2-(2,4-dimethyl-6-(tetrahydro-2H-pyran-4-yl)phenoxy)acetohydrazide (114 mg, 0.41 mmol) and indol-6-carboxaldehyde (65.3 mg, 0.45 mmol) were dissolved in ethanol, followed by stirring overnight under reflux. After the completion of the reaction, the reaction mixture was concentrated under reduced pressure, and purified by column chromatography (silica gel; ethyl acetate:hexane=7:3) to obtain Compound 457 (78 mg, 47%) as a brown solid.

$^1$H NMR (400 MHz, DMSO-$d_6$): δ 11.44-11.40 (m, 1H), 11.32-11.23 (m, 1H), 8.49 (s, 0.5H), 8.04 (2s, 0.45H), 7.72 (s, 0.53H), 7.60-7.26 (m, 3.5H), 6.93-6.88 (m, 2H), 6.48-6.43 (m, 1H), 4.77 (s, 0.9H), 4.33 (s, 1.1H), 3.91 (bs, 2H), 3.22-3.18 (m, 2H), 2.25-2.23 (m, 6H), 1.67-1.61 (m, 4H).

The following scheme 2 shows the preparation methods of compounds 233, 272, 236, 252, 244, 245, 238 and 289 using compounds 108, 065 and 187 synthesized according to scheme 1.

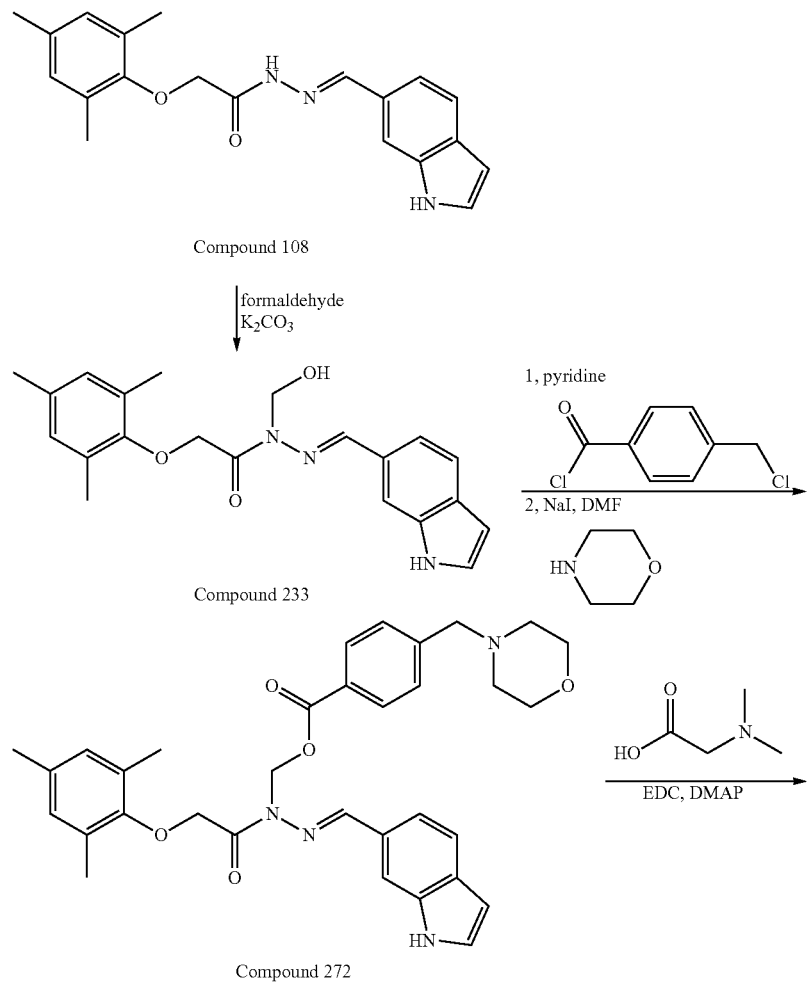

[Scheme 2]

-continued
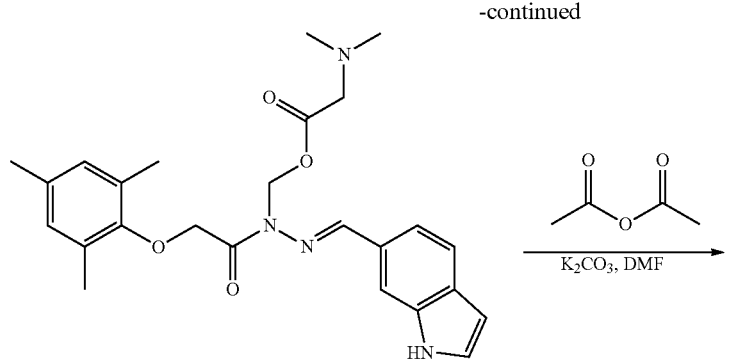
Compound 236
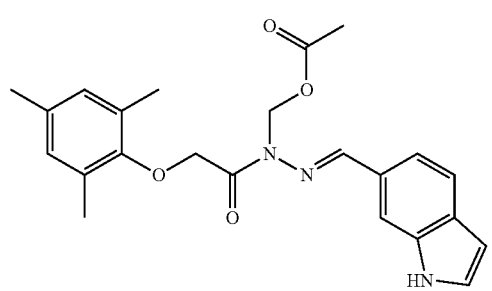
Compound 252
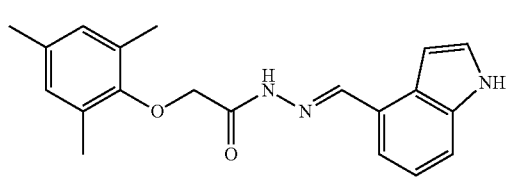
Compound 065
| formaldehyde
K$_2$CO$_3$
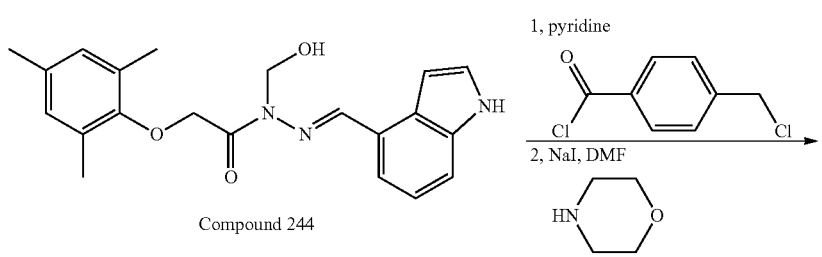
Compound 244
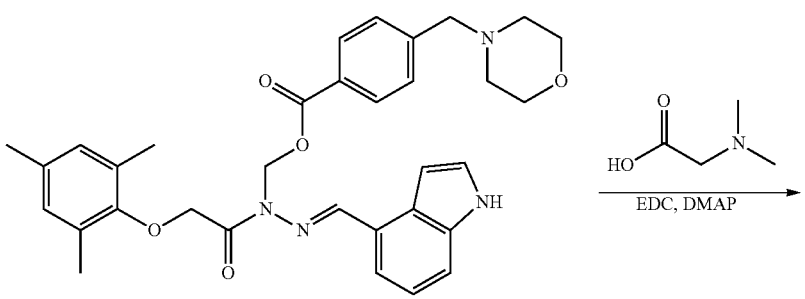
Compound 245

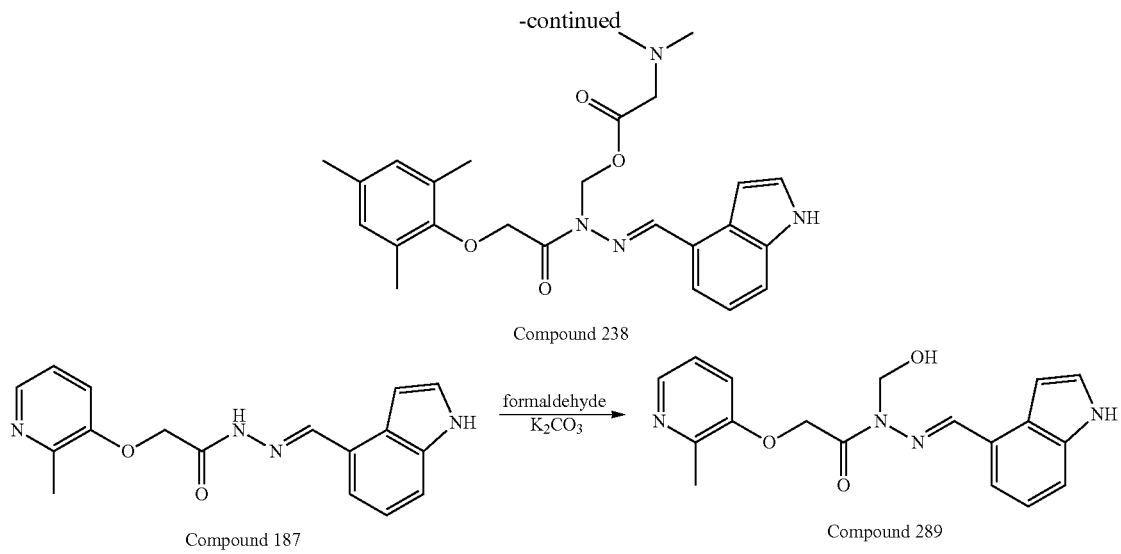

Compound 238

Compound 187

Compound 289

EXAMPLE 93

Synthesis of Compound 233

Compound 108 (510 mg, 1.52 mmol), formaldehyde 35% (0.6 mL, 15.2 mmol), potassium carbonate (210 mg, 1.52 mmol) were dissolved in dimethylformamide 1 mL, followed by stirring at 40° C. for 48 hours. After the completion of the reaction, water was added thereto, and then the form white solid was filtered out. The filtrate was concentrated under reduced pressure, and purified by column chromatography to obtain Compound 233 (110 mg, 20%).

$^1$H NMR (400 MHz, DMSO-d$_6$): δ 11.43-11.40 (m, 1H), 8.52 (s, 1H), 8.07-7.37 (m, 5H), 6.83 (d, J=4.44 Hz, 2H), 6.45 (m, 1H), 6.45 (m, 2H), 5.52 (d, J=15.5 Hz, 2H), 4.89 (s, 1H), 4.03 (s, 1H), 2.22 (m, 9H).

EXAMPLE 94

Synthesis of Compound 244

Compound 065 (510 mg, 1.52 mmol), formaldehyde 35% (0.6 mL, 15.2 mmol) and potassium carbonate (210 mg, 1.52 mmol) were dissolved in dimethylformamide 1 mL, followed by increasing the temperature to 40° C. and stirring for 2 days. After the completion of the reaction, water was added thereto, and then the form white solid was filtered out. The filtrate was concentrated under reduced pressure, and purified by column chromatography (ethyl acetate: hexane=1:1) to yield Compound 244 (110 mg, 20%).

$^1$H NMR (400 MHz, DMSO-d$_6$): δ 11.4 (m, 1H), 8.69-8.24 (2s, 1H), 7.67 (m, 1H), 7.50 (m, 1H), 7.22 (m, 3H), 6.83 (m, 2H), 6.45 (m, 1H), 5.54 (m, 2H), 4.83 (s, 1H), 4.36 (s, 1H), 2.31 (m, 9H).

EXAMPLE 95

Synthesis of Compound 289

Compound 187 (110 mg, 0.36 mmol) was dissolved in dimethylformamide 1.5 mL. Formaldehyde (0.09 mL, 1.08 mmol) and potassium carbonate (41 mg, 0.36 mmol) were added thereto, followed by stirring at 45° C. for 16 hours. After the completion of the reaction, the formed solid was filtered to obtain Compound 289 (50 mg, 41%).

$^1$H NMR (400 MHz, DMSO-d$_6$): δ 11.56 (m, 1H), 8.51-8.27 (m, 1H), 8.02 (m, 1H), 7.66 (d, J=8.0 Hz, 1H), 7.51 (m, 1H), 7.31-6.97 (m, 4H), 5.75 (m, 2H), 5.42-4.76 (m, 2H), 2.43 (m, 3H).

EXAMPLE 96

Synthesis of Compound 272

Compound 233 (200 mg, 0.55 mmol) and 3-(chloromethyl)benzyl chloride (113 mg, 0.60 mmol) were dissolved in pyridine 2 mL, followed by stirring for 3 hours at room temperature. After the completion of the reaction, the reaction mixture was added with water, and extracted with ethyl acetate. The obtained organic layer was dried over magnesium sulfate, and concentrated under reduced pressure. The concentrate was dissolved in dimethylformamide, and then morpholine (0.04 mL, 0.44 mmol) and sodium iodide (cat.) were added thereto, followed by stirring for 4 hours at room temperature. After the completion of the reaction, water was added thereto, thereby forming a white solid, which was filtered to obtain Compound 272 (20 mg, 0.03 mmol, 32%).

$^1$H NMR (400 MHz, DMSO-d$_6$): δ 11.49 (m, 1H), 8.55 (s, 0.5H), 7.88 (s, 0.5H), 7.81 (m, 3H), 7.69-7.63 (m, 1.5H), 7.57-7.51 (m, 1.5H), 7.41 (m, 3H), 6.83 (d, J=12.0 Hz, 2H), 6.59 (m, 1H), 6.50 (d, J=1.80 Hz, 2H), 4.77 (s, 1H), 4.34 (s, 1H), 3.52 (m, 6H), 2.30 (m, 4H), 2.20 (m, 9H)

EXAMPLE 97

Synthesis of Compound 245

Compound 244 (33 mg, 0.09 mmol) and 3-(chloromethyl)benzyl chloride (17 mg, 0.12 mmol) were dissolved in pyridine 0.2 mL, followed by stirring for 3 hours at room temperature. After the completion of the reaction, the reaction mixture was added with water, and extracted with ethyl acetate. The obtained organic layer was dried over magnesium sulfate, and concentrated under reduced pressure. The concentrate was dissolved in dimethylformamide, and then morpholine (0.02 mL, 0.24 mmol) and sodium iodide (cat.) were added thereto, followed by stirring for 4 hours at room temperature. The reaction mixture was added with water, and extracted with ethyl acetate. The obtained organic layer was dried over magnesium sulfate, and purified by column chromatography (ethyl acetate:hexane=1:1~2:1) to obtain Compound 245 (18 mg, 58%).

$^1$H NMR (400 MHz, DMSO-d$_6$): δ 11.52-46 (m, 1H), 8.71-8.24 (2s, 1H), 7.89-7.76 (m, 3H), 7.70-7.65 (m, 1H), 7.44-7.23 (m, 5H), 6.84 (m, 2H), 6.50 (d, J=14.7 Hz, 2H), 4.83 (s, 1H), 4.36 (s, 1H), 3.53-3.49 (m, 6H), 2.31 (m, 4H), 2.22 (m, 9H).

EXAMPLE 98

Synthesis of Compound 238

Compound 244 (20 mg, 0.05 mmol), N,N-dimethylglycine (6 mg, 0.05 mmol), EDC (24 mg, 0.13 mmol) and 4-dimethylaminopyridine (3 mg, 0.03 mmol) were dissolved in methylene chloride:dimethylformamide=1 mL:1 mL, followed by stirring for 2 hours at room temperature. The reaction mixture was added with water, and extracted with methylene chloride. The obtained organic layer was dried over magnesium sulfate, and recrystallized with hexane to obtain Compound 238 (10 mg, 44%).

$^1$H NMR (400 MHz, DMSO-d$_6$): δ 11.4 (m, 1H), 8.70 (s, 0.5H), 8.23 (s, 0.5H), 7.74-7.56 (m, 2H), 7.34-7.21 (m, 3H), 6.84 (d, J=5.92 Hz, 2H), 6.27 (d, J=15.2 Hz, 2H), 4.83 (s, 1H), 4.36 (s, 1H), 2.19 (m, 15H).

EXAMPLE 99

Synthesis of Compound 236

Compound 233 (20 mg, 0.06 mmol), N,N-dimethylglycine (16 mg, 0.15 mmol), EDC (28 mg, 0.15 mmol) and 4-dimethylaminopyridine (4 mg, 0.03 mmol) were dissolved in dimethylacetamide 1 mL, followed by stirring for 1.5 hours at 40° C. The reaction mixture was cooled to 0° C., and then stirred for 30 minutes with slowly adding of 1.5 mL of water. After further stirring for 1 hour, the reaction mixture was added with water, and extracted with methylene chloride. The obtained organic layer was concentrated under reduced pressure. The concentrate was purified by column chromatography (ethyl acetate:methylene chloride=1:4) to obtain Compound 236 (10 mg, 37%).

$^1$H NMR (400 MHz, DMSO-d$_6$): δ 11.52 (m, 1H), 8.54, 8.06 (s, 1H), 7.89 (s, 0.5H), 7.59-7.56 (m, 3H), 6.85 (d, J=7.48 Hz, 2H), 6.5 (m, 1H), 6.45 (d, J=18.0 Hz, 1H), 4.76 (s, 1H), 4.34 (s, 1H), 3.15 (d, J=18.9 Hz, 2H), 2.19 (m, 15H).

EXAMPLE 100

Synthesis of Compound 252

Compound 233 (30 mg, 0.08 mmol), acetic acid anhydrous (8 mg, 0.08 mmol) and triethylamine (8 mg, 0.08 mmol) were dissolved in dimethylformamide 1 mL, followed by stirring at room temperature for 12 hours. Water was added to the reaction mixture, thereby forming a white solid, which was filtered and then recrystallized with hexane to obtain Compound 252 (20 mg, 0.04 mmol, 60%).

$^1$H NMR (400 MHz, DMSO-d$_6$): δ 11.47 (m, 1H), 8.69-8.24 (2s, 1H), 7.67-7.62 (m, 1H), 7.50 (m, 1H), 7.31-7.09 (m, 2.5H), 6.84 (d, J=7.4 Hz, 2H), 6.77 (d, J=3.2 Hz, 0.5H), 6.45 (m, 1H), 5.54 (m, 2H), 4.84 (s, 1H), 4.36 (s, 1H), 2.24 (m, 9H).

The following scheme 3 shows the preparation methods of compounds 164, 177, 243, 195, 198, 201, 375 and 380 using compounds 065, 108, 229 and 378 synthesized according to scheme 1.

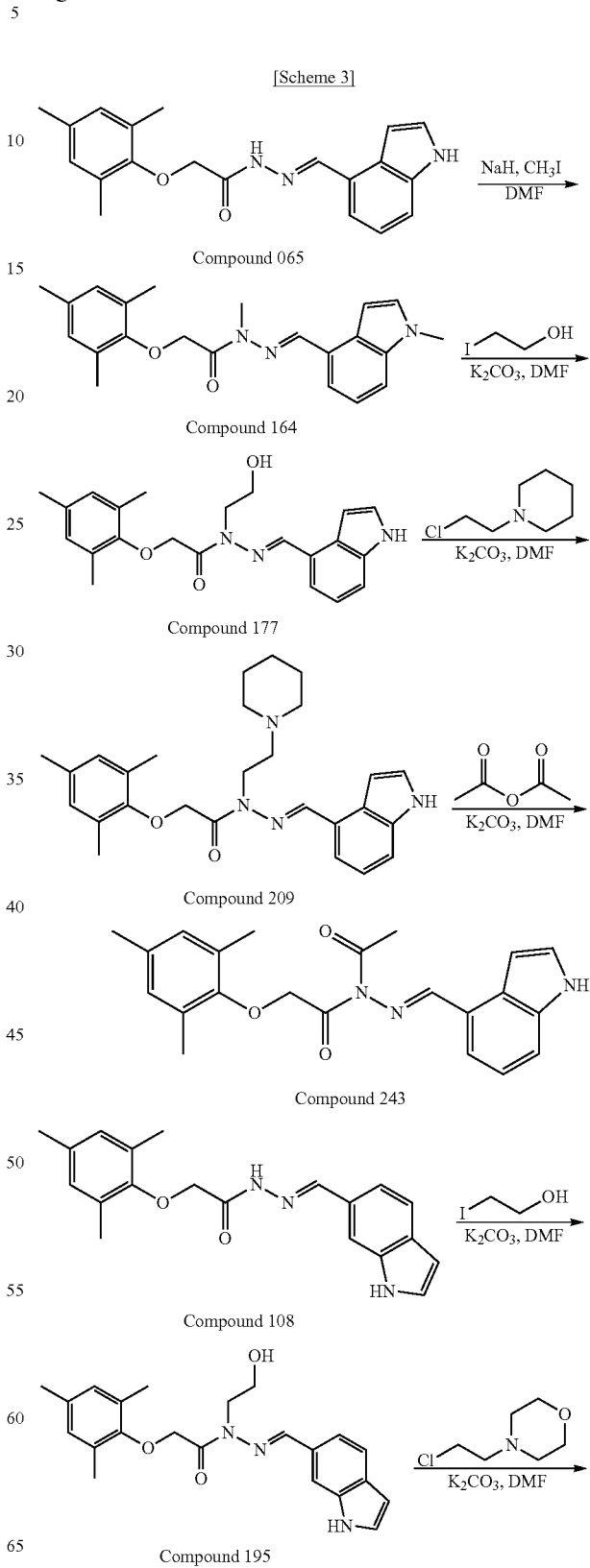

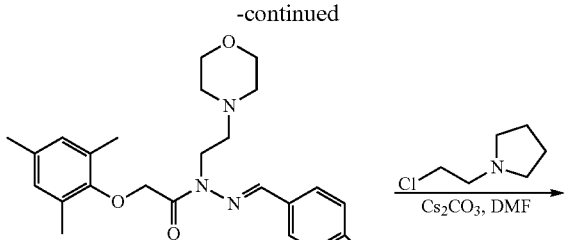

Compound 198

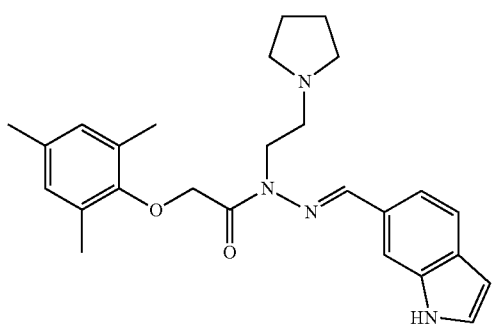

Compound 201

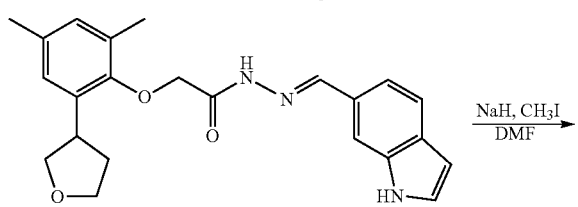

Compound 229

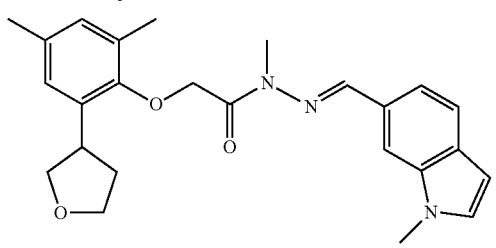

Compound 375

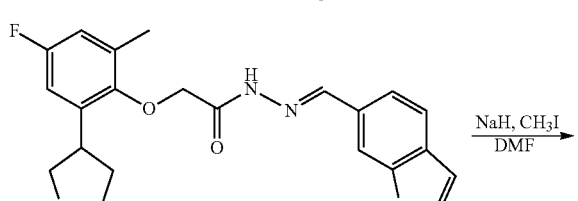

Compound 378

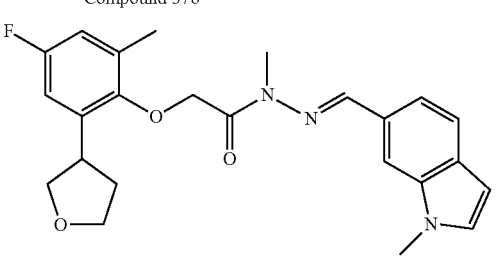

Compound 380

EXAMPLE 101

Synthesis of Compound 164

Compound 065 (265 mg, 0.79 mmol), 2-iodomethane (336 mg, 2.37 mmol), sodium hydride (38 mg, 1.58 mmol) was dissolved in dimethylformamide (2 mL), followed by stirring at 90° C. for 12 hours. The reaction mixture was added with water, and extracted with ethyl acetate. The obtained organic layer was dried over magnesium sulfate, and concentrated under reduced pressure. The concentrate was purified by column chromatography to obtain Compound 164 (152 mg, 0.42 mmol, 53%).

$^1$H NMR (400 MHz, DMSO-$d_6$): δ 8.18 (s, 0.5H), 7.48 (s, 0.5H), 7.36 (d, J=3.0 Hz, 1H), 7.32 (m, 1H), 7.18 (m, 0.5H), 6.81 (s, 2H), 6.77 (d, J=3.0 Hz, 1H), 4.96 (s, 2H), 3.77 (s, 3H), 3.38 (s, 3H), 2.18 (s, 9H).

EXAMPLE 102

Synthesis of Compound 375

Compound 229 (50 mg, 0.13 mmol) was dissolved in dimethylformamide. Sodium hydride (16.7 mg, 0.38 mmol) and methyl iodide (54.5 mg, 0.38 mmol) were added thereto. After reacting at room temperature for 2 hours, the reaction mixture was concentrated under reduced pressure. The residue was purified by column chromatography (silica gel; methylene chloride/methanol, 10/1) to obtain Compound 375 (8.5 mg, 16%) as a brown solid.

$^1$H NMR (400 MHz, DMSO-$d_6$): δ 11.48-11.44 (m, 1H), 11.35-11.23 (m, 1H), 8.48, 8.05 (2s, 1H), 7.72 (s, 0.5H), 7.59-7.27 (m, 3.5H), 6.96-6.88 (m, 2H), 6.47-6.43 (m, 1H), 4.77 (s, 1H), 4.34 (s, 3H), 4.02-3.92 (m, 2H), 3.77-3.73 (m, 2H), 3.56 (s, 3H), 3.53-3.43 (m, 2H), 2.26-2.20 (m, 7H), 1.89-2.20 (m, 1H).

Example 103

Synthesis of Compound 380

Compound 378 (115 mg, 0.28 mmol) was dissolved in dimethylformamide. Sodium hydride (36.9 mg, 0.85 mmol) and methyl iodide (0.53 mL, 0.85 mmol) were added thereto. After reacting at room temperature for 1 day, the reaction mixture was added with water, and extracted with ethyl acetate. The obtained organic layer was concentrated under reduced pressure. The concentrate was purified by column chromatography (silica gel; hexane/ethyl acetate, 3/7) to obtain Compound 380 (26 mg, 22%) as a white solid.

$^1$H NMR (400 MHz, CDCl$_3$): δ 7.88 (s, 1H), 7.59 (d, 1 H, J=8.3 Hz), 7.47 (s, 1H), 7.43 (dd, 1 H, J=8.3, 1.3 Hz), 7.13 (d, 1 H, J=3.0 Hz), 6.88 (dd, 1 H, J=9.5, 3.1 Hz), 6.79 (dd, 1 H, J=8.7, 3.0 Hz), 6.49 (d, 1 H, J=3.0 Hz), 5.03, 5.01 (ABq, 2 H, J=10.3, 15.8 Hz), 4.14-4.04 (m, 2H), 3.94-3.84 (m, 2H), 3.81 (s, 3H), 3.74-3.71 (m, 1H), 3.49 (s, 3H), 2.44-2.38 (m, 1H), 2.36 (s, 3H), 1.98-1.89 (m, 1H).

EXAMPLE 104

Synthesis of Compound 177

Compound 065 (265 mg, 0.79 mmol), 2-iodoethanol (0.12 mL, 1.58 mmol) and potassium carbonate (436 mg, 3.16 mmol) were dissolved in dimethylformamide (2 mL), followed by stirring at 50° C. for 12 hours. After the completion of the reaction, the reaction mixture was added with water, and extracted with ethyl acetate. The obtained organic layer was washed with brine, dried over magnesium sulfate, and purified by column chromatography to obtain Compound 177 (121 mg, 0.32 mmol, 41%).

$^1$H NMR (400 MHz, DMSO-d$_6$): δ 11.33 (bs, 1H), 8.37 (s, 1H), 7.44 (d, J=7.92 Hz, 1H), 7.39 (t, J=2.88 Hz, 1H), 7.26 (d, J=7.08 Hz, 1H), 7.12 (t, J=7.8 Hz, 1H), 6.82 (s, 2H), 6.79 (m, 1H), 4.99 (m, 2H), 4.96 (s, 2H), 4.14 (t, J=5.76 Hz, 2H), 3.3 (m, 2H), 2.20 (s, 6H), 2.16 (s, 3H).

EXAMPLE 105

Synthesis of Compound 195

Compound 108 (265 mg, 0.79 mmol), 2-iodoethanol (0.12 mL, 1.58 mmol) and potassium carbonate (436 mg, 3.16 mmol) were dissolved in dimethylformamide (2 mL), followed by stirring at 50° C. for 12 hours. After the completion of the reaction, the reaction mixture was added with water, and extracted with ethyl acetate. The obtained organic layer was washed with brine, dried over magnesium sulfate, and purified by column chromatography to obtain Compound 195 (50 mg, 17%).

$^1$H NMR (400 MHz, DMSO-d$_6$): δ 11.27 (bs, 1H), 8.19 (s, 1H), 7.64 (s, 1H), 7.50 (d, J=8.2 Hz, 1H), 7.39 (t, J=2.96 Hz, 1H), 7.30 (m, 1H), 6.83 (s, 2H), 6.41 (m, 1H), 4.9 (m, 1H), 4.88 (s 2H), 4.08 (t, J=6.28 Hz, 2H), 3.58 (m, 2H), 2.18 (d, J=4.28 Hz, 9H).

EXAMPLE 106

Synthesis of Compound 198

Compound 108 (100 mg, 0.29 mmol), 4-(2-chloroethyl)morpholine (0.11 g, 0.58 mmol) and potassium carbonate (164 mg, 1.2 mmol) were dissolved in dimethylformamide (2 mL), followed by stirring at 90° C. for 12 hours. After the completion of the reaction, the reaction mixture was added with water, and extracted with ethyl acetate. The obtained organic layer was dried over magnesium sulfate, and purified by column chromatography to obtain Compound 198.

$^1$H NMR (400 MHz, DMSO-d$_6$): δ 11.26 (bs, 1H), 8.13 (s, 1H), 7.66 (s, 1H), 7.52 (d, J=8.2 Hz, 1H), 7.39 (t, J=2.96 Hz, 1H), 7.30 (m, 1H), 6.82 (s, 2H), 6.41 (m, 1H), 4.87 (s, 2H), 4.16 (m 2H), 3.46 (m, 4H), 2.22 (d, J=4.28 Hz, 9H).

EXAMPLE 107

Synthesis of Compound 201

Compound 108 (40 mg, 0.12 mmol), 1-(2-chloroethyl)pyrrolidine (40 mg, 0.24 mmol) and cesium carbonate (116 mg, 0.36 mmol) were dissolved in dimethylformamide, followed by stirring at 100° C. for 12 hours. After the completion of the reaction, the reaction mixture was added with water, and extracted with dichloromethane. The obtained organic layer was dried over magnesium sulfate, and purified by column chromatography to obtain Compound 201 (17 mg, 33%).

$^1$H NMR (400 MHz, DMSO-d$_6$): δ 11.26 (bs, 1H), 8.11 (s, 1H), 7.65 (s, 1H), 7.52 (d, J=8.2 Hz, 1H), 7.39 (t, J=2.96 Hz, 1H), 7.31 (m, 1H), 6.82 (s, 2H), 6.4 (m, 1H), 4.87 (s, 2H), 4.15 (s, 2H), 2.53 (m, 6H), 2.18 (d, J=3.2 Hz, 9H), 1.68 (m, 4H).

EXAMPLE 108

Synthesis of Compound 243

Compound 065 (30 mg, 0.08 mmol), acetic acid anhydrous (9 mg, 0.08 mmol) and potassium carbonate (12 mg, 0.08 mmol) were dissolved in dimethylformamide 2 mL, followed by stirring at room temperature for 12 hours. After the completion of the reaction, the reaction mixture was added with water, and extracted with ethyl acetate. The obtained organic layer was dried over magnesium sulfate, and concentrated under reduced pressure. The concentrate was purified by column chromatography to obtain Compound 243 (517 mg, 64%).

$^1$H NMR (400 MHz, DMSO-d$_6$): δ 11.62 (m, 1H), 8.44-8.37 (m, 1H), 8.25 (s, 0.5H), 8.80 (m, 1H), 7.51-7.33 (m, 2.5H), 7.02 (d, J=3.48 Hz, 0.5H), 6.85 (d, J=5.8 Hz, 1H), 4.83 (s, 1H), 4.37 (s, 1H), 2.66 (m, 3H), 2.10 (m, 9H).

The following scheme 4 shows the preparation methods of compounds 072, 232, 237 and 239.

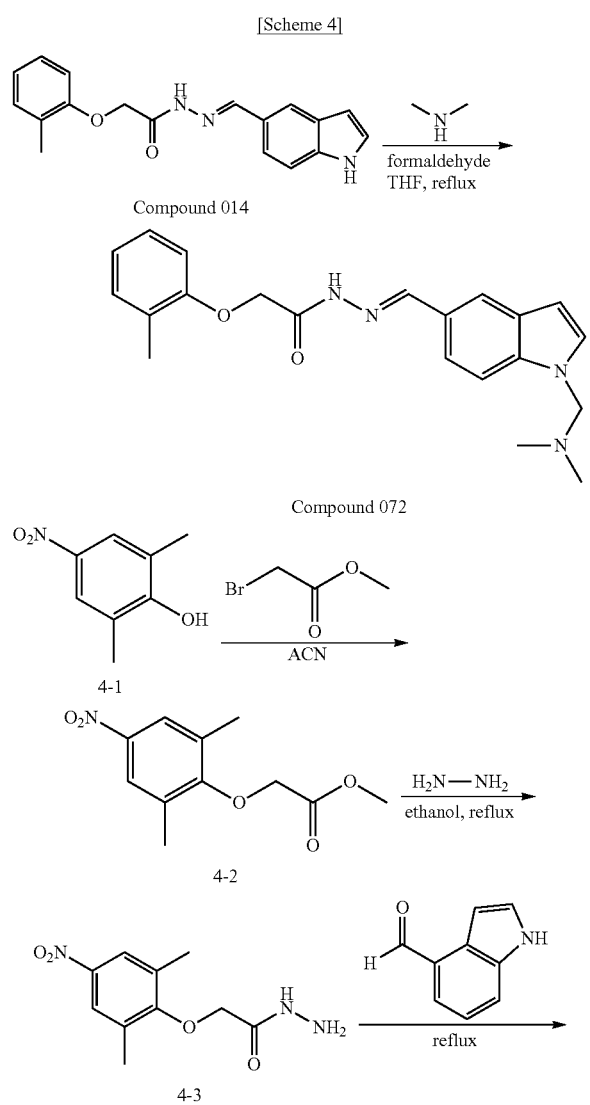

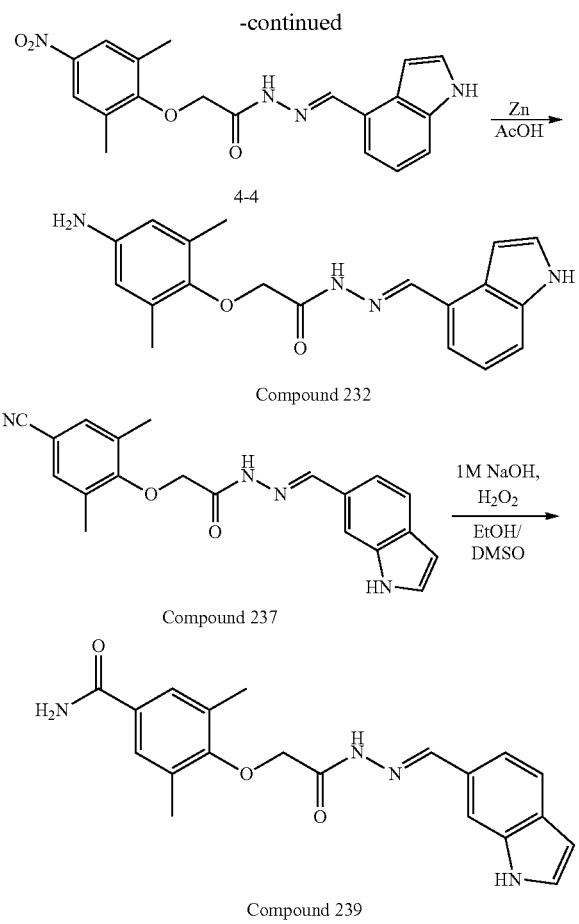

Compound 232

Compound 237

Compound 239

EXAMPLE 109

Synthesis of Compound 072

Compound 014 (100 mg, 1.52 mmol), formaldehyde (48.6 mg, 1.62 mmol), and 2 M dimethylamine solution in tetrahydrofuran (1.62 mL, 3.24 mmol) were stirred for 6 hours under reflux. After the completion of the reaction, the reaction mixture was added with water, and extracted with ethyl acetate. The obtained organic layer was dried over magnesium sulfate, and concentrated under reduced pressure. The concentrate was purified by column chromatography to obtain Compound 072 (6 mg, 5%).

$^1$H NMR (400 MHz, DMSO-$d_6$ δ 11.4 (bs, 0.8H), 8.32-8.06 (m, 0.7H), 7.80-7.79 (m, 1H), 7.63-7.61 (m, 1H), 7.57-7.55 (m, 1H), 7.41-7.40 (m, 1H), 7.14-7.10 (m, 2H), 6.87-6.79 (m, 2H), 6.51-6.50 (m, 1H), 5.14-4.63 (m, 4H), 2.23-2.18 (m, 9H).

EXAMPLE 110

Synthesis of Compound 232

Step 1. Synthesis of methyl 2-(2,6-dimethyl-4-nitrophenoxy)acetate (Compound 4-2): 2,6-dimethyl-4-nitrophenol (1000 mg, 5.98 mmol) and methyl bromoacetate (0.6 mL, 5.98 mmol) and cesium carbonate (2.9 g, 8.97 mmol) were dissolved in acetonitrile 10 mL, followed by stirring at 80° C. for 12 hours. The reaction mixture was added with water, and extracted with ethyl acetate. The obtained organic layer was dried over magnesium sulfate, and purified by column chromatography (ethyl acetate:hexane=1:1) to obtain methyl 2-(2,6-dimethyl-4-nitrophenoxy)acetate (682 mg, 48%).

Step 2. Synthesis of 2-(2,6-dimethyl-4-nitrophenoxy)acetohydrazide (Compound 4-3): methyl 2-(2,6-dimethyl-4-nitrophenoxy)acetate (300 mg, 1.25 mmol), hydrazine monohydrate (0.07 mL, 1.40 mmol) were dissolved in EtOH 3 mL, followed by stirring at 90° C. for 12 hours. The reaction mixture was purified by column chromatography (ethyl acetate:hexane=1:1) to obtain 2-(2,6-dimethyl-4-nitro-phenoxy)acetohydrazide (280 mg, 96%).

Step 3. Synthesis of (E)-N'-((1H-indol-4-yl)methylene)-2-(2,6-dimethyl-4-nitrophenoxy)acetohydrazide (Compound 4-4): 2-(2,6-dimethyl-4-nitrophenoxy)acetohydrazide (289 mg, 1.21 mmol), 1H-indol-4-carbaldehyde (175 mg, 1.21 mmol) were dissolved in EtOH 3 mL, followed by stirring at 90° C. for 12 hours. The reaction mixture was purified by column chromatography (ethyl acetate:hexane=1:1) to obtain (E)-N'-((1H-indol-4-yl)methylene)-2-(2,6-dimethyl-4-nitrophenoxy)acetohydrazide (127 mg, 29%).

Step 4. Synthesis of (E)-N'-((1H-indol-4-yl)methylene)-2-(4-amino-2,6-dimethylphenoxy)acetohydrazide (Compound 232): (E)-N'-((1H-indol-4-yl)methylene)-2-(2,6-dimethyl-4-nitrophenoxy)acetohydrazide (20 mg, 0.05 mmol) and zinc (74 mg, 1 mmol) were dissolved in acetic acid 1 mL, followed by stirring for 6 hours at room temperature. The reaction mixture was purified by column chromatography (ethyl acetate:hexane=2:1) to obtain Compound 232 (2 mg, 11%).

$^1$H NMR (400 MHz, CD$_3$OD): δ 8.68 (s, 0.6H), 8.20 (s, 0.4H), 7.51-7.30 (m, 3H), 7.21-7.15 (m, 2H), 6.83 (m, 0.5H), 6.45 (d, J=8.04H, 1.5H), 4.62 (s, 1H), 4.40 (s, 1H), 2.25 (s, 6H).

EXAMPLE 111

Synthesis of Compound 239

Compound 237 (16 mg, 0.05 mmol) was dissolved in EtOH:dimethylsulfoxide=4 mL:1 mL.

The reaction mixture was cooled to 0° C., and added with 1 M sodium hydroxide and 30% H$_2$O$_2$. The temperature of the reaction mixture was increased to room temperature, followed by stirring for 2 hours. After the completion of the reaction, the reaction mixture was added with water, and extracted with ethyl acetate. The obtained organic layer was dried over magnesium sulfate, and concentrated under reduced pressure. The concentrate was purified by column chromatography to obtain Compound 239 (8 mg, 44%).

$^1$H NMR (400 MHz, DMSO-$d_6$): δ 11.43 (d, J=15.4 Hz, 1H), 11.32-11.21 (d, J=40.9 Hz, 1H), 8.48-8.04 (2s, 1H), 7.84 (m, 1H), 7.71 (s, 0.5H), 7.29-7.22 (m, 1.5H), 6.45 (m, 1H), 4.85 (s, 1H), 4.42 (s, 1H), 2.30 (d, J=5.16 Hz, 6H).

The following scheme 5 shows the preparation methods of aldehyde compounds (Compounds 1-5) of scheme 1.

[Scheme 5]

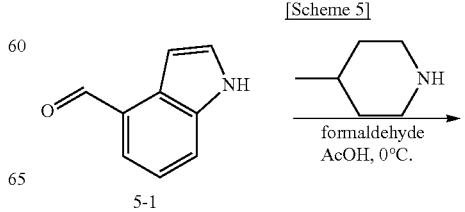

5-1

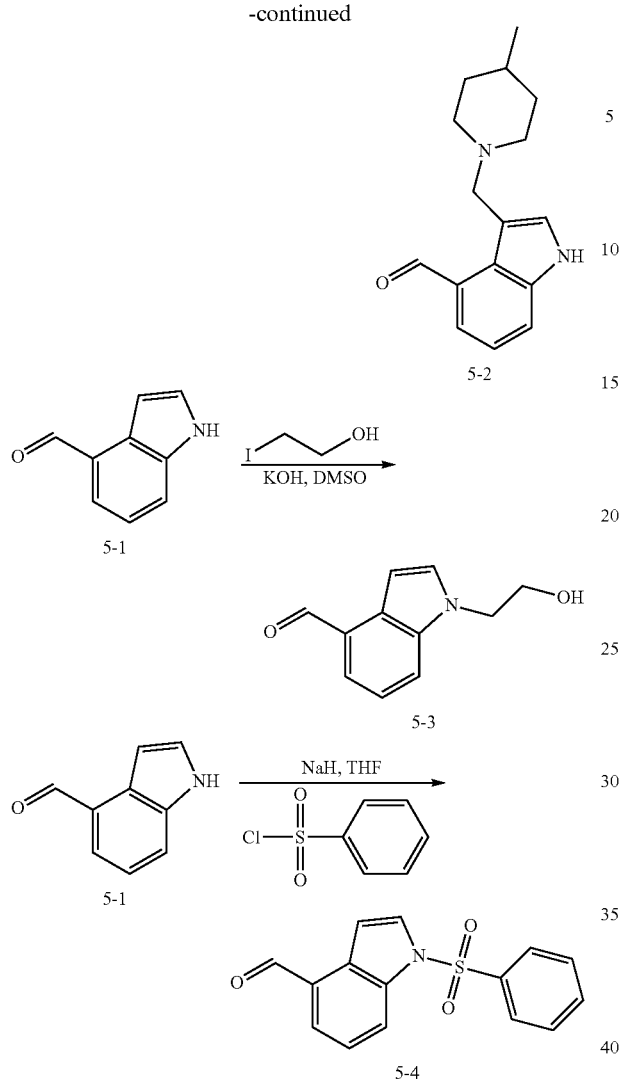

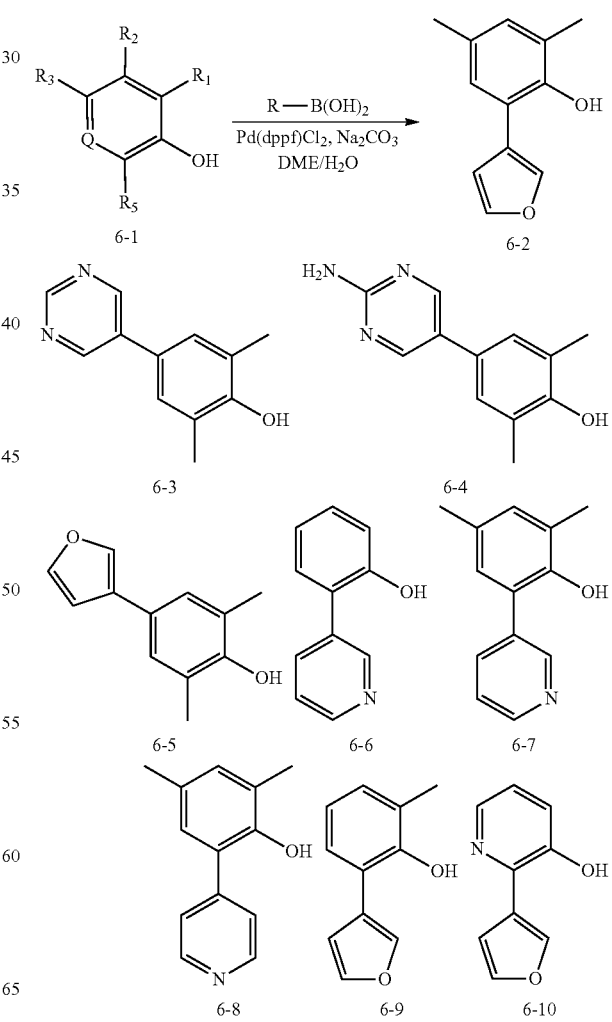

PREPARATION EXAMPLE 1

Synthesis of Compound 5-2 (an Intermediate of Compound 211)

Compound 5-1 (200 mg, 1.38 mmol) and formaldehyde 37%(1.1 mL, 1.66 mmol) were dissolved in acetic acid. The reaction mixture was cooled to 0° C., and added with 4-methylpiperidine (154 mL, 1.38 mmol), followed by stirring at room temperature for 3 hours. After the completion of the reaction, the reaction mixture was added with 1 M NaOH, and extracted with ethyl acetate. The obtained organic layer was washed with brine, dried over magnesium sulfate, and concentrated under reduced pressure to obtain Compound 5-2 (311 mg, 87%).

PREPARATION EXAMPLE 2

Synthesis of Compound 5-3 (an Intermediate of Compound 180)

Compound 5-1 (125 mg, 1.06 mmol), 2-iodoethanol (0.1 mL, 1.59 mmol) and KOH (96 mg, 2.12 mmol) were dissolved in dimethylsulfoxide (2 mL), followed by stirring at room temperature for 12 hours. After the completion of the reaction, the reaction mixture was added with water, and extracted with ethyl acetate. The obtained organic layer was purified by column chromatography to obtain Compound 5-3 (120 mg, 59.8%).

PREPARATION EXAMPLE 3

Synthesis of Compound 5-4 (an Intermediate of Compound 280)

Compound 5-1 (1 g, 6.89 mmol) was dissolved in tetrahydrofuran, and then sodium hydride (360 mg, 8.27 mmol) was added thereto. Benzenesulfonyl chloride (1.2 g, 6.89 mmol) was added thereto, followed by stirring at room temperature for 12 hours. After the completion of the reaction, the reaction mixture was added with water, and extracted with ethyl acetate. The obtained organic layer was purified by column chromatography to obtain Compound 5-4 (500 mg, 25%).

The following scheme 6 shows the preparation methods of starting compounds (Compounds 1-1) of schemes 1 and 7.

-continued

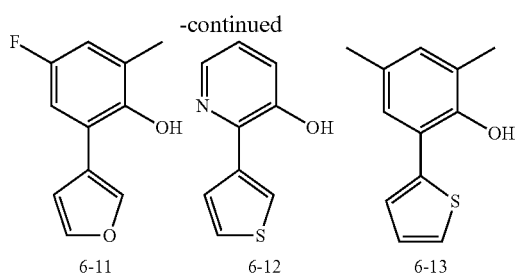

6-11    6-12    6-13

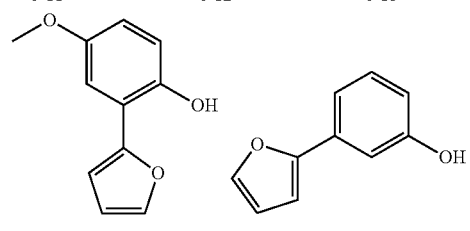

6-14    6-15

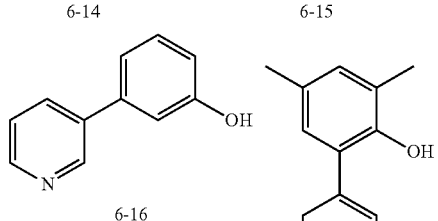

6-16    6-17

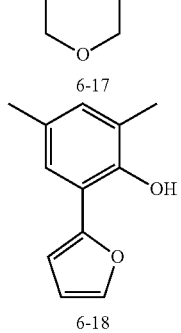

6-18

PREPARATION EXAMPLE 4

Synthesis of 2-(furan-3-yl)-4,6-dimethylphenol (Compound 6-2)

2-Bromo-4,6-dimethylphenol (1.8 g, 8.9 mmol) was dissolved in dimethoxyethane/water (2:1). Furan-3-ylboronic acid (1 g, 8.9 mmol), Pd(dppf)Cl$_2$ (0.36 g, 0.45 mmol) and sodium carbonate (3.7 g, 45 mmol) were added thereto, followed by stirring for 1 hour under reflux. After the completion of the reaction, the reaction mixture was added with a saturated sodium hydrogen carbonate aqueous solution, and extracted with ethyl acetate. The obtained organic layer was dried over magnesium sulfate, concentrated under reduced pressure, and purified by column chromatography to obtain 2-(furan-3-yl)-4,6-dimethylphenol (0.9 g, 54%).

PREPARATION EXAMPLE 5

Synthesis of 2,6-dimethyl-4-(pyrimidin-5-yl)phenol (Compound 6-3)

4-Bromo-2,6-dimethylphenol (0.5 g, 2.5 mmol) was dissolved in dimethoxyethane/water (2:1). pyrimidin-5-ylboronic acid (0.37 g, 2.8 mmol), Pd(dppf)Cl$_2$ (0.02 g, 0.13 mmol) and sodium carbonate (0.79 g, 7.5 mmol) were added thereto, followed by reacting in microwave reactor at 120° C. for 15 minutes. After the completion of the reaction, the reaction mixture was added with water, and extracted with ethyl acetate. The obtained organic layer was dried over magnesium sulfate, concentrated under reduced pressure, and purified by column chromatography to obtain 2,6-dimethyl-4-(pyrimidin-5-yl)phenol (0.1 g, 20%).

PREPARATION EXAMPLE 6

Synthesis of 4-(2-aminopyrimidin-5-yl)-2,6-dimethylphenol (Compound 6-4)

2-Aminopyrimidin-5-ylboronic acid (0.76 g, 5.4 mmol) was dissolved in dimethoxyethane/water (2:1). 4-Bromo-2,6-dimethylphenol (0.91 g, 4.52 mmol) and Pd(dppf)Cl$_2$ (0.19 g, 0.14 mmol), sodium carbonate (1.4 g, 14 mmol) were added thereto, followed by reacting in microwave reactor at 120° C. for 15 minutes. After the completion of the reaction, the reaction mixture was added with water, and extracted with dichloromethane. The obtained organic layer was dried over magnesium sulfate, concentrated under reduced pressure, and purified by column chromatography to obtain 4-(2-aminopyrimidin-5-yl)-2,6-dimethylphenol (0.27 g, 27%).

PREPARATION EXAMPLE 7

Synthesis of 4-(furan-3-yl)-2,6-dimethylphenol (Compound 6-5)

4-Bromo-2,6-dimethylphenol (350 mg, 1.74 mmol), 3-furanylboronic acid (269 mg, 2.26 mmol), Pd(dppf)Cl$_2$ (71 mg, 0.087 mmol) and sodium carbonate (553 mg, 5.22 mmol) were dissolved in DME:water=4 mL:2 mL, followed by stirring in microwave at 120° C. for 20 minutes. After the completion of the reaction, the reaction mixture was filtered using Celite. The obtained filtrate was extracted with ethyl acetate, dried over magnesium sulfate, and purified by column chromatography (hexane:ethyl acetate=9:1) to obtain 4-(furan-3-yl)-2,6-dimethylphenol (225 mg, 50%).

PREPARATION EXAMPLE 8

Synthesis of 2-(pyridin-3-yl)phenol (Compound 6-6)

2-Bromophenol (0.5 g, 2.9 mmol) was dissolved in dimethoxyethane/water (2:1). Pyridin-3-ylboronic acid (0.71 g, 5.8 mmol) and Pd(dppf)Cl$_2$ (0.12 g, 0.14 mmol), sodium carbonate (1.2 g, 14 mmol) were added thereto, followed by stirring for 1 hour under reflux. After the completion of the reaction, the reaction mixture was added with water, and extracted with ethyl acetate. The obtained organic layer was dried over magnesium sulfate under reduced pressure, and purified by column chromatography to obtain 2-(pyridin-3-yl)phenol (0.25 g, 20%).

PREPARATION EXAMPLE 9

Synthesis of 2,4-dimethyl-6-(pyridin-3-yl)phenol (Compound 6-7)

2-bromo-4,6-dimethylphenol (1 g, 5 mmol) was dissolved in dimethoxyethane/water (2:1). Pyridin-3-ylboronic acid (0.62 g, 5 mmol) and Pd(dppf)Cl$_2$ (0.20 g, 0.25 mmol), sodium carbonate (2.1 g, 25 mmol) were added thereto, followed by stirring for 1 hour under reflux. After the completion of the reaction, the reaction mixture was added with water, and extracted with ethyl acetate. The obtained organic layer was dried over magnesium sulfate, concentrated under reduced pressure, and purified by column chromatography to obtain 2,4-dimethyl-6-(pyridin-3-yl) phenol (0.7 g, 70%).

PREPARATION EXAMPLE 10

Synthesis of 2,4-dimethyl-6-(pyridin-4-yl)phenol (Compound 6-8)

2-Bromo-4,6-dimethylphenol (0.5 g, 2.5 mmol) was dissolved in dimethoxyethane/water (2:1). Pyridin-4-ylboronic acid (0.32 g, 2.5 mmol) and Pd(dppf)Cl$_2$ (0.10 g, 0.13 mmol), sodium carbonate (1 g, 13 mmol) were added thereto, followed by stirring for 1 hour under reflux. After the completion of the reaction, the reaction mixture was added with water, and extracted with ethyl acetate. The obtained organic layer was dried over magnesium sulfate, concentrated under reduced pressure, and purified by column chromatography to obtain 2,4-dimethyl-6-(pyridin-4-yl)phenol (0.15 g, 30%).

PREPARATION EXAMPLE 11

Synthesis of 2-(furan-3-yl)-6-methylphenol (Compound 6-9)

2-Bromo-6-methylphenol (800 mg, 4.28 mmol), 3-furan boronic acid (574 mg, 5.13 mmol), sodium carbonate (1400 mg, 12.8 mmol) and Pd$_2$(dppf)$_2$Cl$_2$ (699 mg, 0.82 mmol) were dissolved in dimethoxyethane/water 10 mL/10 mL, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (ethyl acetate:hexane=1:3) to obtain 2-(furan-3-yl)-6-methylphenol (273 mg, 26%).

PREPARATION EXAMPLE 12

Synthesis of 2-(furan-3-yl)pyridin-3-ol (Compound 6-10)

2-Bromopyridin-3-ol (200 mg, 1.15 mmol), 3-furan boronic acid (574 mg, 1.38 mmol), sodium carbonate (365 mg, 12.8 mmol) and Pd$_2$(dppf)$_2$Cl$_2$ (187 mg, 0.23 mmol) were dissolved in dimethoxyethane/water 2 mL/1 mL, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (ethyl acetate:hexane=1:3) to obtain 2-(furan-3-yl)pyridin-3-ol (50 mg, 27%).

PREPARATION EXAMPLE 13

Synthesis of 4-fluoro-2-(furan-3-yl)-6-methylphenol (Compound 6-11)

2-bromo-4-fluoro-6-methylphenol (337 mg, 1.20 mmol), 3-furanylboronic acid (162 mg, 1.45 mmol), Pd(dppf)Cl$_2$ (98.3 mg, 0.12 mmol) and sodium carbonate (383 mg, 3.61 mmol) were dissolved in DME:water=20 mL:10 mL, followed by stirring in microwave at 120° C. for 20 minutes. The reaction mixture was filtered through Celite. The filtrate was concentrated under reduced pressure, and purified by column chromatography (silica gel; hexane/ethyl acetate, 9/1) to obtain 4-fluoro-2-(furan-3-yl)-6-methylphenol (96 mg, 30%) as a yellow oil.

PREPARATION EXAMPLE 14

Synthesis of 2-(thiophene-3-yl)pyridin-3-ol (Compound 6-12)

2-Bromopyridin-3-ol (100 mg, 0.58 mmol), 3-thiophenyl boronic acid (88 mg, 0.69 mmol), sodium carbonate (184 mg, 2.07 mmol) and Pd$_2$(dppf)$_2$Cl$_2$ (94 mg, 0.12 mmol) were dissolved in dimethoxyethane/water of 1 mL/1 mL, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (ethyl acetate:hexane=1:3) to obtain 2-(thiophene-3-yl)pyridin-3-ol (50 mg, 48%).

PREPARATION EXAMPLE 15

Synthesis of 2,4-dimethyl-6-(thiophene-2-yl)phenol (Compound 6-13)

2-Bromo-4,6-dimethylphenol (500 mg, 2.49 mmol), 2-thiophenyl boronic acid (88 mg, 2.99 mmol), sodium carbonate (791 mg, 7.47 mmol) and Pd$_2$(dppf)$_2$Cl$_2$ (406 mg, 0.49 mmol) were dissolved in dimethoxyethane/water 6 mL/3 mL, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (ethyl acetate:hexane=1:3) to obtain 2,4-dimethyl-6-(thiophene-2-yl)phenol (231 mg, 45%).

PREPARATION EXAMPLE 16

Synthesis of 2-(furan-2-yl)-4-methoxyphenol (Compound 6-14)

2-Bromo-4-methoxyphenol (400 mg, 1.97 mmol), 2-furanylboronic acid (287 mg, 2.56 mmol), Pd(dppf)Cl$_2$ (81 mg, 0.1 mmol) and sodium carbonate (626 mg, 5.91 mmol) were dissolved in DME:water=4 mL:2 mL, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (hexane:ethyl acetate=9:1) to obtain 2-(furan-2-yl)-4-methoxyphenol (212 mg, 57%).

PREPARATION EXAMPLE 17

Synthesis of 3-(furan-2-yl)phenol (Compound 6-15)

3-Bromophenol (500 mg, 2.86 mmol) and furan-2-boronic acid (420 mg, 3.76 mmol) were dissolved in dimethoxyethane/water=5 mL/2.5 mL. Pd(dppf)Cl$_2$ (118 mg, 0.14 mmol) and sodium carbonate (919 mg, 8.67 mmol) were added thereto, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (hexane:ethyl acetate=9:1) to obtain 3-(furan-2-yl)phenol (191 mg, 41%).

PREPARATION EXAMPLE 18

Synthesis of 3-(pyridin-3-yl)phenol (Compound 6-16)

3-Bromophenol (500 mg, 2.86 mmol) and pyridin-3-ylboronic acid (422 mg, 3.76 mmol) were dissolved in dimethoxyethane/water=5 mL/2.5 mL. Pd(dppf)Cl$_2$ (118 mg, 0.14 mmol) and sodium carbonate (919 mg, 8.67 mmol) were added thereto, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (hexane:ethyl acetate=9:1) to obtain 3-(pyridin-3-yl)phenol (386 mg, 78%).

PREPARATION EXAMPLE 19

Synthesis of 2-(3,6-dihydro-2H-pyran-4-yl)-4,6-dimethylphenol (Compound 6-17)

2-Bromo-4,6-dimethylphenol (430 mg, 2.14 mmol), 2-(3,6-dihydro-2H-pyran-4-yl)-4,4,5,5-tetramethyl-1,3,2-dioxaborolane (494 mg, 2.35 mmol), Pd(dbpf)Cl$_2$ (69.7 mg, 0.11 mmol) and sodium carbonate (680 mg, 6.45 mmol) were dissolved in dimethoxyethane:water=3 mL:1 mL, followed by stirring in microwave at 120° C. for 30 minutes. The reaction mixture was filtered through Celite. The filtrate was concentrated under reduced pressure, and purified by column chromatography (silica gel; hexane/ethyl acetate, 9/1) to obtain 2-(3,6-dihydro-2H-pyran-4-yl)-4,6-dimethylphenol (160 mg, 37%) as a colorless oil.

PREPARATION EXAMPLE 20

Synthesis of 2-(furan-2-yl)-4,6-dimethylphenol (Compound 6-18)

2-Bromo-4,6-dimethylphenol (500 mg, 2.49 mmol), furan-2-ylboronic acid (88 mg, 2.99 mmol), sodium carbonate (791 mg, 7.47 mmol) and Pd$_2$(dppf)$_2$Cl$_2$ (406 mg, 0.49 mmol) were dissolved in dimethoxyethane/water 6 mL/3 mL, followed by stirring in microwave at 120° C. for 20 minutes. After the completion of the reaction, the reaction mixture was filtered using Celite. The filtrate was added with water, and extracted with ethyl acetate. The obtained organic layer was dried over magnesium sulfate, and purified by column chromatography (ethyl acetate:hexane=1:3) to obtain 2-(furan-2-yl)-4,6-dimethylphenol (231 mg, 45%).

The following scheme 7 shows the preparation methods of starting compounds (Compounds 1-1) of scheme 1.

[Scheme 7]

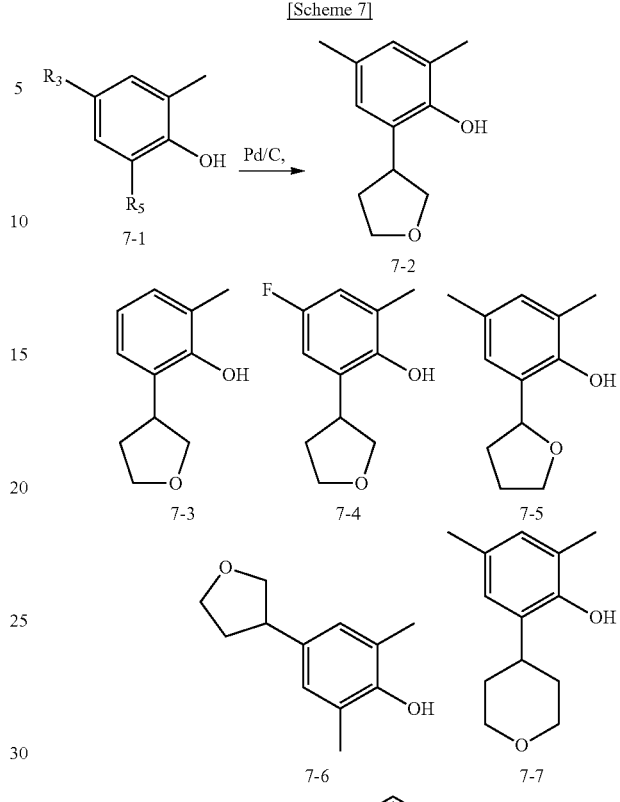

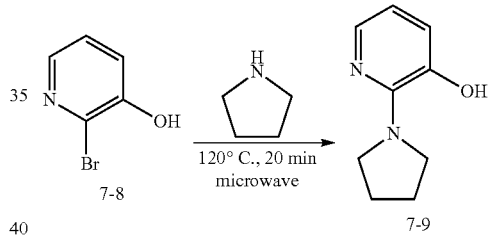

PREPARATION EXAMPLE 21

Synthesis of 2,4-dimethyl-6-(tetrahydrofuran-3-yl)phenol (Compound 7-2)

2-(furan-3-yl)-4,6-dimethylphenol (Compound 6-2) (0.6 g, 3.2 mmol) was dissolved in methanol. Palladium carbon (0.06 g) was added thereto, followed by stirring under hydrogen balloon at room temperature for 6 hours. After the completion of the reaction, the reaction mixture was filtered through Celite. The filtrate was concentrated under reduced pressure, and purified by column chromatography to obtain 2,4-dimethyl-6-(tetrahydrofuran-3-yl)phenol (0.45 g, 73%).

PREPARATION EXAMPLE 22

Synthesis of 2-methyl-6-(tetrahydrofuran-3-yl)phenol (Compound 7-3)

2-(furan-3-yl)-6-methylphenol (Compound 6-9) (173 mg, 0.70 mmol) and palladium carbon (25 mg, 15%) were dissolved in methanol:tetrahydrofuran=1 mL:1 mL, followed by stirring under hydrogen balloon for 48 hours. After the completion of the reaction, the reaction mixture was filtered through Celite. The filtrate was concentrated under reduced pressure, and purified by column chromatography (hexane:ethyl acetate=3:1) to obtain 2-methyl-6-(tetrahydrofuran-3-yl)phenol (117 mg, 93%).

PREPARATION EXAMPLE 23

Synthesis of 4-fluoro-2-methyl-6-(tetrahydrofuran-3-yl)phenol (Compound 7-4)

4-fluoro-2-(furan-3-yl)-6-methylphenol (Compound 6-11) (471 mg, 2.45 mmol) were dissolved in methanol. Palladium carbon (64.3 mg, 5 wt %) was added thereto, followed by stirring under hydrogen balloon for 24 hours. After the completion of the reaction, the reaction mixture was filtered through Celite. The filtrate was concentrated under reduced pressure. The concentrate was purified by column chromatography (silica gel; hexane/ethyl acetate, 9/1) to obtain 4-fluoro-2-methyl-6-(tetrahydrofuran-3-yl)phenol (368 mg, 76%) as a white solid.

PREPARATION EXAMPLE 24

Synthesis of 2,4-dimethyl-6-(tetrahydrofuran-2-yl)phenol (Compound 7-5)

2-(furan-2-yl)-4,6-dimethylphenol (Compound 6-18) (200 mg, 1.06 mmol) were dissolved in methanol 3 mL. Palladium carbon (30 mg) was added thereto, followed by stirring under hydrogen balloon for 12 hours. After the completion of the reaction, the reaction mixture was filtered through Celite. The filtrate was concentrated under reduced pressure to obtain 2,4-dimethyl-6-(tetrahydrofuran-2-yl)phenol (200 mg, 98%).

PREPARATION EXAMPLE 25

Synthesis of 2,6-dimethyl-4-(tetrahydrofuran-3-yl)phenol (Compound 7-6)

4-(furan-3-yl)-2,6-dimethylphenol (Compound 6-5) (110 mg, 0.74 mmol) were dissolved in tetrahydrofuran:methanol=1 mL:1 mL. Palladium carbon (15 mg, 15%) was added thereto, followed by stirring under hydrogen balloon for 18 hours. After the completion of the reaction, the reaction mixture was filtered through Celite. The filtrate was concentrated under reduced pressure to obtain 2,6-dimethyl-4-(tetrahydrofuran-3-yl)phenol (74 mg, 72%).

PREPARATION EXAMPLE 26

Synthesis of 2,4-dimethyl-6-(tetrahydro-2H-pyran-4-yl)phenol (Compound 7-7)

2-(3,6-dihydro-2H-pyran-4-yl)-4,6-dimethylphenol (Compound 6-17) (234 mg, 1.14 mmol) was dissolved in methanol. Palladium carbon (92 mg, 40 wt %) was added thereto, followed by stirring under hydrogen balloon for 24 hours. After the completion of the reaction, the reaction mixture was filtered through Celite. The filtrate was concentrated under reduced pressure. The residue was purified by column chromatography (silica gel; hexane/ethyl acetate, 9/1) to obtain 2,4-dimethyl-6-(tetrahydro-2H-pyran-4-yl)phenol (156 mg, 66%) as a white solid.

PREPARATION EXAMPLE 27

Synthesis of 2-(pyrrolidin-1-yl)pyridin-3-ol (Compound 7-9)

2-bromopyridin-3-ol (200 mg, 1.15 mmol) and pyrrolidine (184 mg, 2.58 mmol) were added in a reaction tube, followed by reacting in microwave at 120° C. for 20 minutes. The reaction mixture was added with 1 M HCl solution to neutralized, and extracted with ethyl acetate and dichloromethane. The obtained organic layer was dried over magnesium sulfate, and concentrated under reduced pressure. The concentrate was purified by column chromatography to obtain 2-(pyrrolidin-1-yl)pyridin-3-ol (78 mg, 41%).

The structural formulae are as following Tables 1-9.

TABLE 1

| Compound | Structure |
| --- | --- |
| 013 | 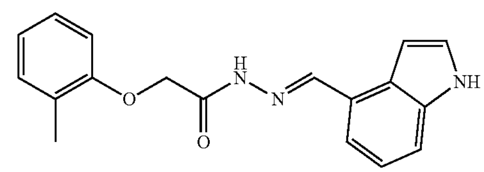 [SMILES: Cc1ccccc1OCC(=O)N/N=C/c1cccc2[nH]ccc12] |
| 014 | 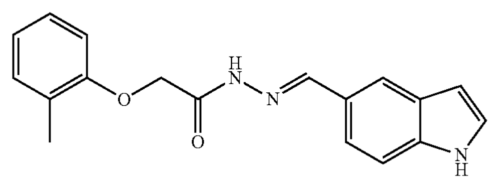 [SMILES: Cc1ccccc1OCC(=O)N/N=C/c1ccc2[nH]ccc2c1] |
| 034 | 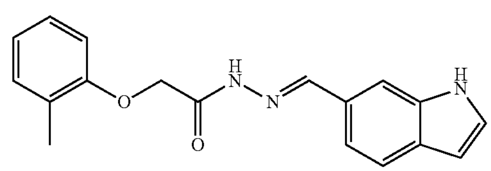 [SMILES: Cc1ccccc1OCC(=O)N/N=C/c1ccc2cc[nH]c2c1] |
| 065 | 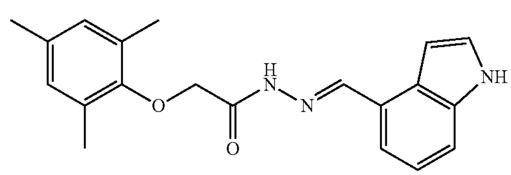 [SMILES: Cc1cc(C)c(OCC(=O)N/N=C/c2cccc3[nH]ccc23)c(C)c1] |
| 072 | 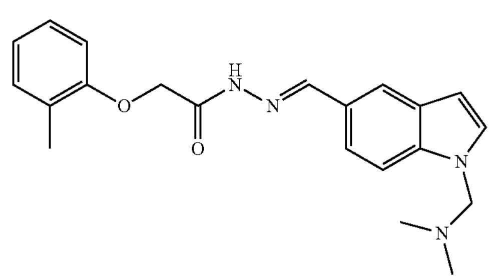 [SMILES: Cc1ccccc1OCC(=O)N/N=C/c1ccc2c(ccn2CN(C)C)c1] |

TABLE 1-continued

| Compound | Structure |
|---|---|
| 083 | (2-methylphenyl)amino-CH2-C(=O)-NH-N=CH-(1H-indol-5-yl) |
| 092 | (4-bromo-2,6-dimethylphenoxy)-CH2-C(=O)-NH-N=CH-(1H-indol-5-yl) |
| 100 | (2-methylphenoxy)-CH2-C(=O)-NH-N=CH-(1H-benzimidazol-5-yl) |
| 108 | (2,4,6-trimethylphenoxy)-CH2-C(=O)-NH-N=CH-(1H-indol-6-yl) |
| 109 | (2,4,6-trimethylphenoxy)-CH2-C(=O)-NH-N=CH-(1H-indol-2-yl) |
| 112 | (4-bromo-2,6-dimethylphenoxy)-CH2-C(=O)-NH-N=CH-(1H-indol-4-yl) |
| 118 | (2,6-dimethylphenoxy)-CH2-C(=O)-NH-N=CH-(1H-indol-4-yl) |
| 121 | (2,6-diisopropylphenoxy)-CH2-C(=O)-NH-N=CH-(1H-indol-4-yl) |

TABLE 1-continued

| Compound | Structure |
|---|---|
| 127 | (2,6-di-tert-butyl-4-methylphenoxy)-CH2-C(=O)-NH-N=CH-(1H-indol-4-yl) |

TABLE 2

| Compound | Structure |
|---|---|
| 133 | (4-bromo-2,6-dimethylphenoxy)-CH2-C(=O)-NH-N=CH-(1H-indol-6-yl) |
| 135 | (2,4,6-trimethylphenyl)amino-CH2-C(=O)-NH-N=CH-(1H-indol-4-yl) |
| 136 | (2,4,6-trimethylphenyl)amino-CH2-C(=O)-NH-N=CH-(1H-indol-3-yl) |
| 137 | (2,6-dimethyl-4-(pyridin-3-yl)phenoxy)-CH2-C(=O)-NH-N=CH-(1H-indol-4-yl) |
| 138 | (2,6-dimethyl-4-(pyridin-3-yl)phenoxy)-CH2-C(=O)-NH-N=CH-(1H-indol-3-yl) |

TABLE 2-continued

| Compound | Structure |
|---|---|
| 139 | 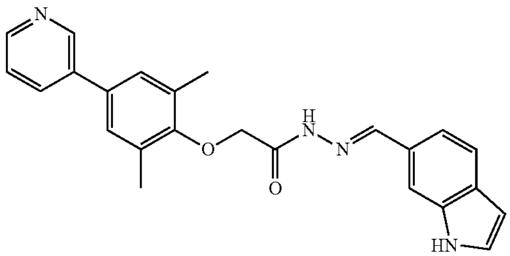 [SMILES: Cc1cc(-c2cccnc2)cc(C)c1OCC(=O)N/N=C/c1ccc2cc[nH]c2c1] |
| 146 | 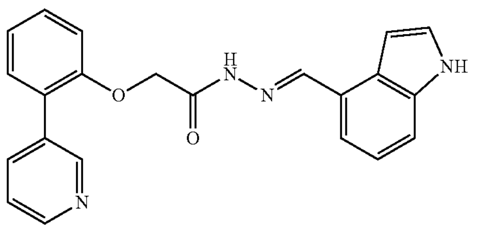 [SMILES: O=C(COc1ccccc1-c1cccnc1)N/N=C/c1cccc2[nH]ccc12] |
| 147 | 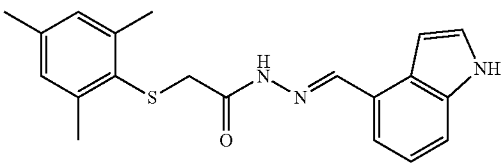 |
| 149 | 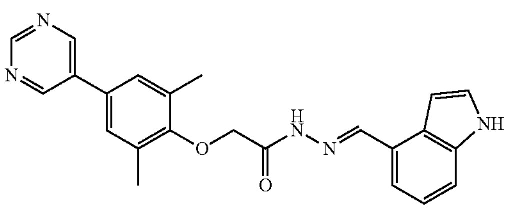 [SMILES: Cc1cc(-c2cncnc2)cc(C)c1OCC(=O)N/N=C/c1cccc2[nH]ccc12] |
| 152 | 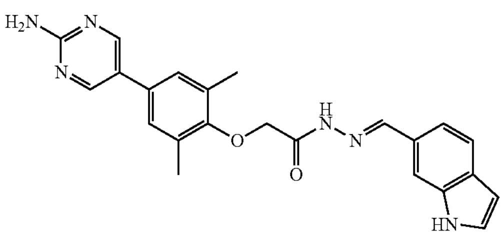 [SMILES: Cc1cc(-c2cnc(N)nc2)cc(C)c1OCC(=O)N/N=C/c1ccc2cc[nH]c2c1] |
| 155 | 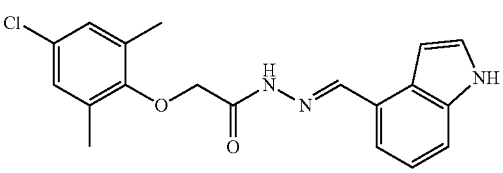 [SMILES: Cc1cc(Cl)cc(C)c1OCC(=O)N/N=C/c1cccc2[nH]ccc12] |
| 156 | 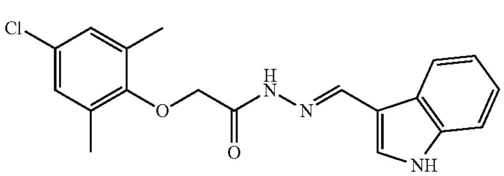 [SMILES: Cc1cc(Cl)cc(C)c1OCC(=O)N/N=C/c1c[nH]c2ccccc12] |

TABLE 2-continued

| Compound | Structure |
|---|---|
| 157 | |
| 158 | |

TABLE 3

| Compound | Structure |
|---|---|
| 159 | 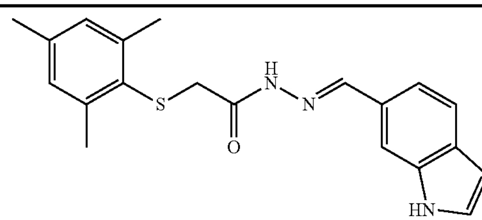 |
| 164 | 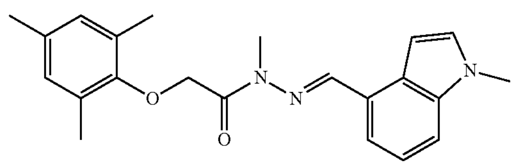 |
| 177 | 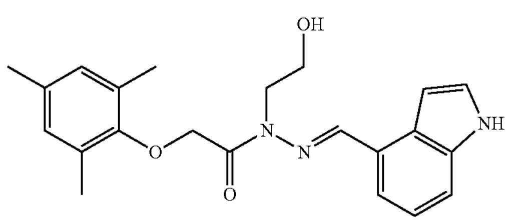 [SMILES: Cc1cc(C)c(OCC(=O)N(CCO)/N=C/c2cccc3[nH]ccc23)c(C)c1] |
| 180 | 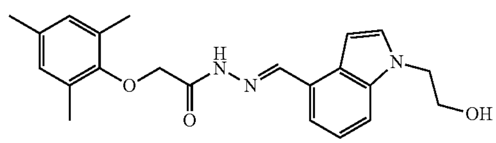 [SMILES: Cc1cc(C)c(OCC(=O)N/N=C/c2cccc3c2ccn3CCO)c(C)c1] |
| 182 | 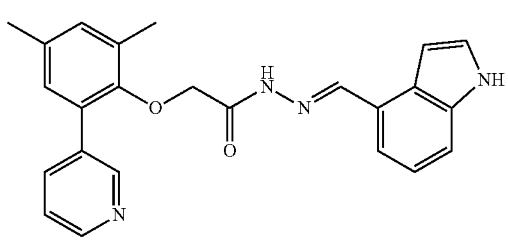 [SMILES: Cc1cc(C)c(OCC(=O)N/N=C/c2cccc3[nH]ccc23)c(-c2cccnc2)c1] |

TABLE 3-continued

| Compound | Structure |
|---|---|
| 183 | 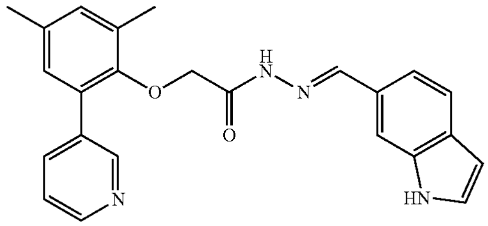 [SMILES: Cc1cc(C)c(OCC(=O)N/N=C/c2ccc3cc[nH]c3c2)c(-c2cccnc2)c1] |
| 184 | 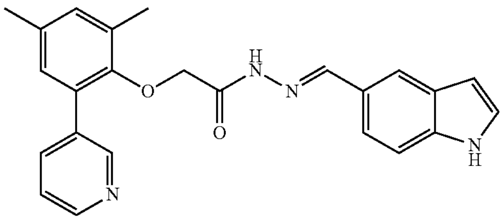 [SMILES: Cc1cc(C)c(OCC(=O)N/N=C/c2ccc3[nH]ccc3c2)c(-c2cccnc2)c1] |
| 187 | 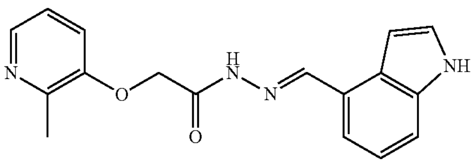 [SMILES: Cc1ncccc1OCC(=O)N/N=C/c1cccc2[nH]ccc12] |
| 190 | 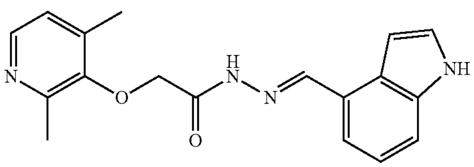 [SMILES: Cc1ccnc(C)c1OCC(=O)N/N=C/c1cccc2[nH]ccc12] |
| 191 | 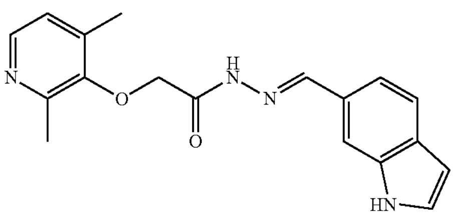 [SMILES: Cc1ccnc(C)c1OCC(=O)N/N=C/c1ccc2cc[nH]c2c1] |
| 192 | 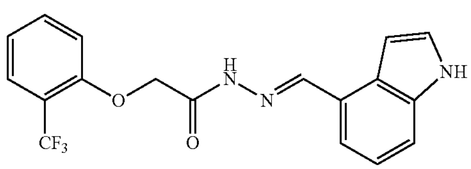 [SMILES: O=C(COc1ccccc1C(F)(F)F)N/N=C/c1cccc2[nH]ccc12] |
| 193 | 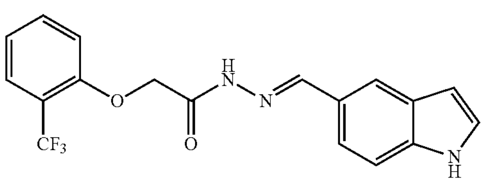 [SMILES: O=C(COc1ccccc1C(F)(F)F)N/N=C/c1ccc2[nH]ccc2c1] |
| 194 | 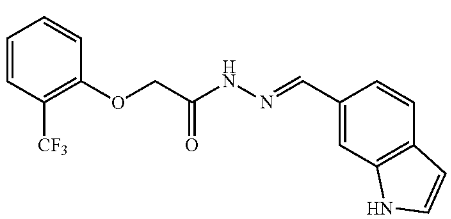 [SMILES: O=C(COc1ccccc1C(F)(F)F)N/N=C/c1ccc2cc[nH]c2c1] |

TABLE 3-continued

| Compound | Structure |
|---|---|
| 195 | 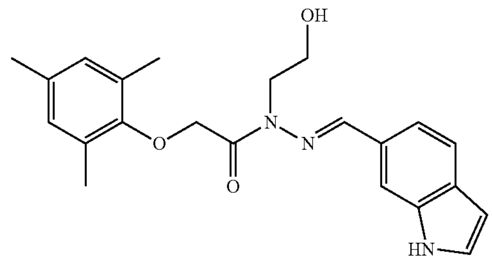 [SMILES: Cc1cc(C)c(OCC(=O)N(CCO)/N=C/c2ccc3cc[nH]c3c2)c(C)c1] |

TABLE 4

| Compound | Structure |
|---|---|
| 196 | 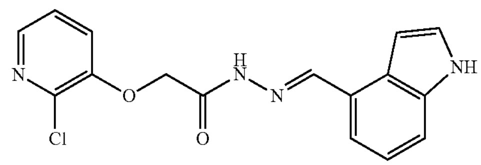 [SMILES: O=C(COc1cccnc1Cl)N/N=C/c1cccc2[nH]ccc12] |
| 198 | 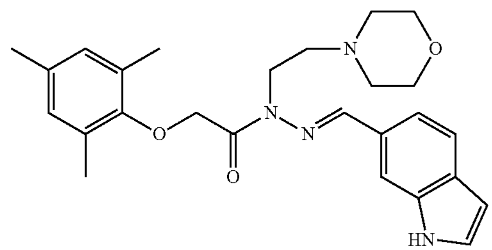 [SMILES: Cc1cc(C)c(OCC(=O)N(CCN2CCOCC2)/N=C/c2ccc3cc[nH]c3c2)c(C)c1] |
| 201 | 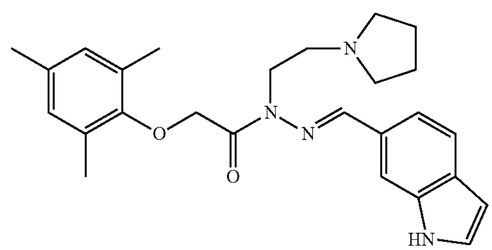 [SMILES: Cc1cc(C)c(OCC(=O)N(CCN2CCCC2)/N=C/c2ccc3cc[nH]c3c2)c(C)c1] |
| 205 | 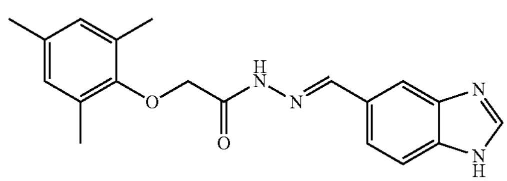 [SMILES: Cc1cc(C)c(OCC(=O)N/N=C/c2ccc3[nH]cnc3c2)c(C)c1] |
| 206 | 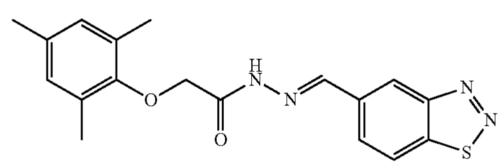 [SMILES: Cc1cc(C)c(OCC(=O)N/N=C/c2ccc3snnc3c2)c(C)c1] |

TABLE 4-continued

| Compound | Structure |
|---|---|
| 211 | 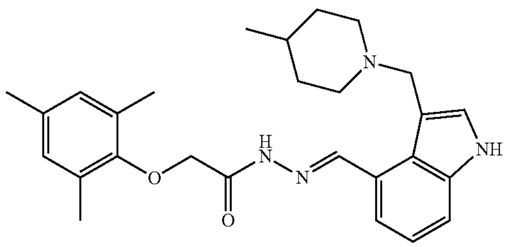 [SMILES: Cc1cc(C)c(OCC(=O)N/N=C/c2cccc3[nH]cc(CN4CCC(C)CC4)c23)c(C)c1] |
| 217 | 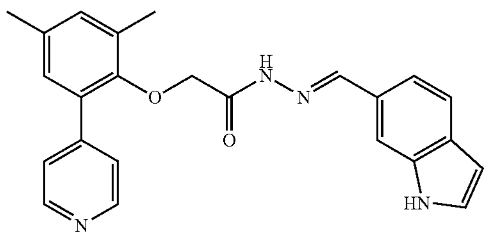 [SMILES: Cc1cc(C)c(OCC(=O)N/N=C/c2ccc3cc[nH]c3c2)c(-c2ccncc2)c1] |
| 218 | 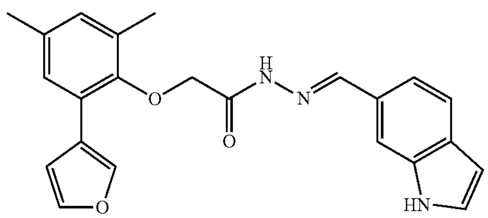 [SMILES: Cc1cc(C)c(OCC(=O)N/N=C/c2ccc3cc[nH]c3c2)c(-c2ccoc2)c1] |
| 227 | 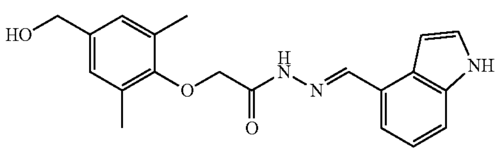 [SMILES: Cc1cc(CO)cc(C)c1OCC(=O)N/N=C/c1cccc2[nH]ccc12] |
| 228 | 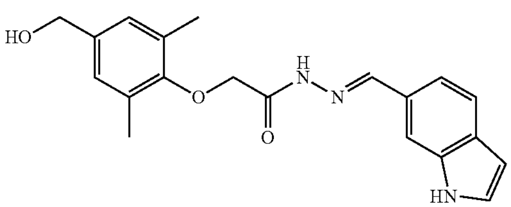 [SMILES: Cc1cc(CO)cc(C)c1OCC(=O)N/N=C/c1ccc2cc[nH]c2c1] |
| 229 | 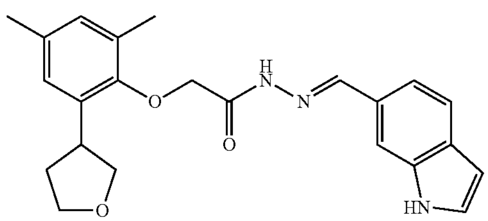 [SMILES: Cc1cc(C)c(OCC(=O)N/N=C/c2ccc3cc[nH]c3c2)c(C2CCOC2)c1] |
| 232 | 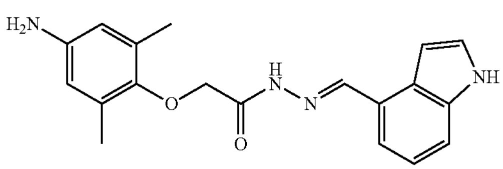 [SMILES: Cc1cc(N)cc(C)c1OCC(=O)N/N=C/c1cccc2[nH]ccc12] |

TABLE 5

| Compound | Structure |
|---|---|
| 233 | 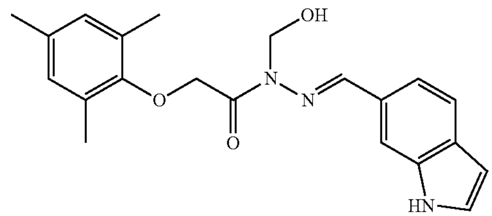 [SMILES: Cc1cc(C)c(OCC(=O)N(CO)/N=C/c2ccc3cc[nH]c3c2)c(C)c1] |
| 236 | 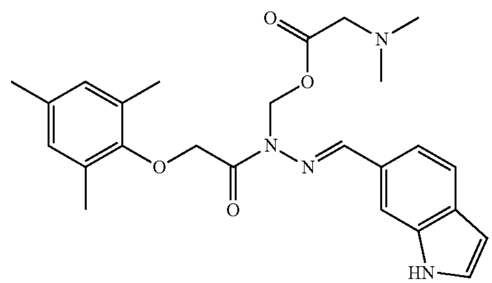 [SMILES: Cc1cc(C)c(OCC(=O)N(COC(=O)CN(C)C)/N=C/c2ccc3cc[nH]c3c2)c(C)c1] |
| 237 | 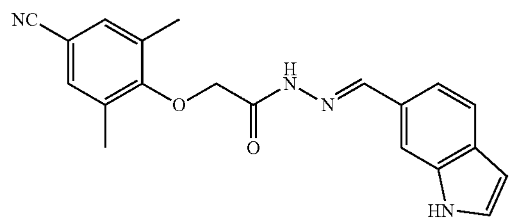 [SMILES: Cc1cc(C#N)cc(C)c1OCC(=O)N/N=C/c1ccc2cc[nH]c2c1] |
| 238 | 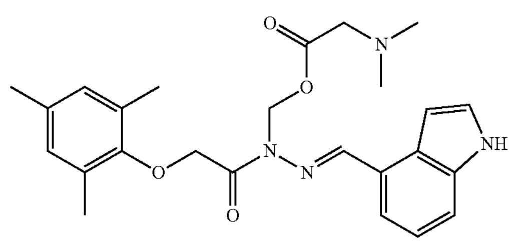 [SMILES: Cc1cc(C)c(OCC(=O)N(COC(=O)CN(C)C)/N=C/c2cccc3[nH]ccc23)c(C)c1] |
| 239 | 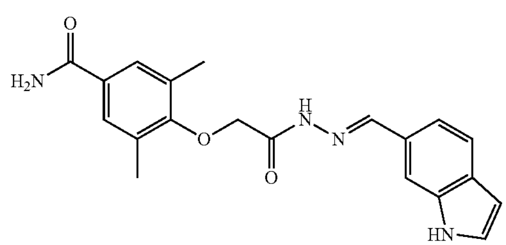 [SMILES: Cc1cc(C(N)=O)cc(C)c1OCC(=O)N/N=C/c1ccc2cc[nH]c2c1] |
| 243 | 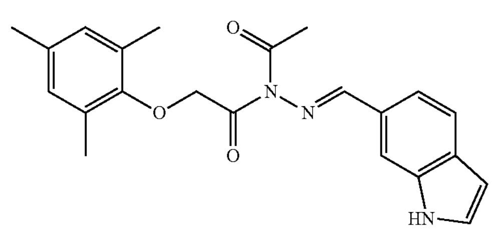 [SMILES: CC(=O)N(/N=C/c1ccc2cc[nH]c2c1)C(=O)COc1c(C)cc(C)cc1C] |

TABLE 5-continued

| Compound | Structure |
|---|---|
| 244 | (structure) |
| 245 | (structure) |
| 252 | (structure) |
| 256 | (structure) |
| 258 | (structure) |
| 259 | (structure) |

TABLE 6

| Compound | Structure |
|---|---|
| 260 | (structure) |
| 272 | (structure) |
| 279 | (structure) |
| 280 | (structure) |
| 286 | (structure) |
| 288 | (structure) |
| 289 | (structure) |

TABLE 6-continued

| Compound | Structure |
|---|---|
| 291 | 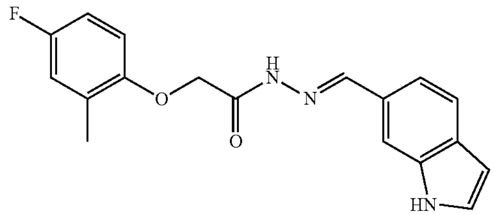 [SMILES: Cc1cc(F)ccc1OCC(=O)N/N=C/c1ccc2cc[nH]c2c1] |
| 293 | 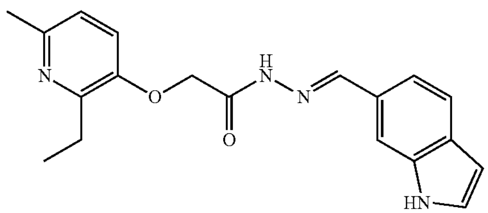 [SMILES: CCc1nc(C)ccc1OCC(=O)N/N=C/c1ccc2cc[nH]c2c1] |
| 301 | 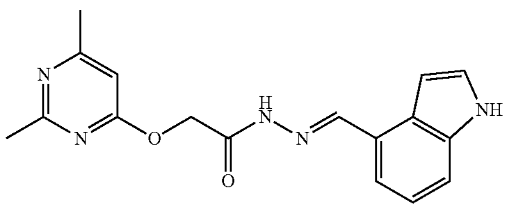 [SMILES: Cc1cc(OCC(=O)N/N=C/c2cccc3[nH]ccc23)nc(C)n1] |
| 302 | 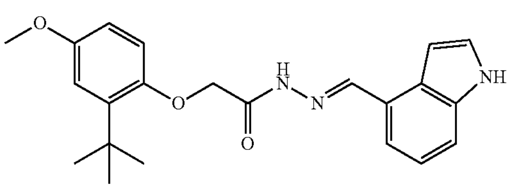 [SMILES: COc1ccc(OCC(=O)N/N=C/c2cccc3[nH]ccc23)c(C(C)(C)C)c1] |
| 303 | 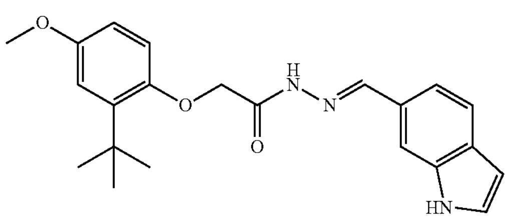 [SMILES: COc1ccc(OCC(=O)N/N=C/c2ccc3cc[nH]c3c2)c(C(C)(C)C)c1] |

TABLE 7

| Compound | Structure |
|---|---|
| 304 | |
| 310 | 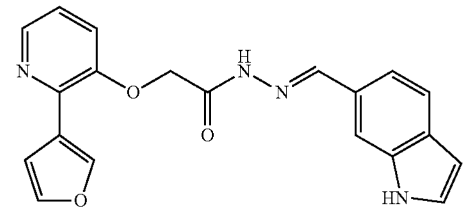 [SMILES: O=C(COc1cccnc1-c1ccoc1)N/N=C/c1ccc2cc[nH]c2c1] |
| 311 | 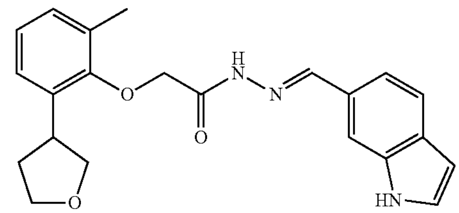 [SMILES: Cc1cccc(C2CCOC2)c1OCC(=O)N/N=C/c1ccc2cc[nH]c2c1] |
| 312 | 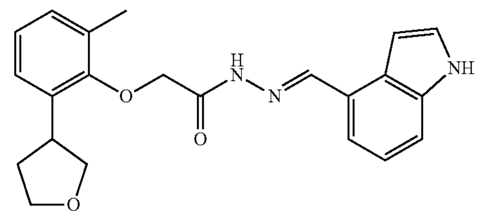 [SMILES: Cc1cccc(C2CCOC2)c1OCC(=O)N/N=C/c1cccc2[nH]ccc12] |
| 313 | 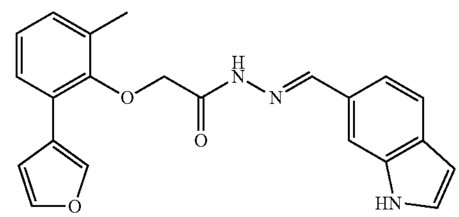 [SMILES: Cc1cccc(-c2ccoc2)c1OCC(=O)N/N=C/c1ccc2cc[nH]c2c1] |
| 314 | 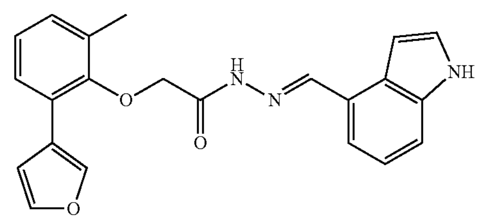 [SMILES: Cc1cccc(-c2ccoc2)c1OCC(=O)N/N=C/c1cccc2[nH]ccc12] |
| 317 | 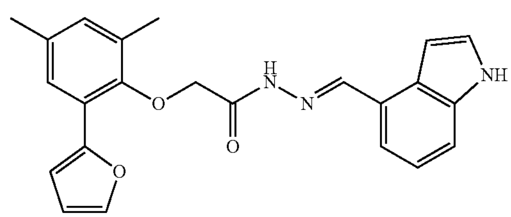 [SMILES: Cc1cc(C)c(OCC(=O)N/N=C/c2cccc3[nH]ccc23)c(-c2ccco2)c1] |
| 318 | 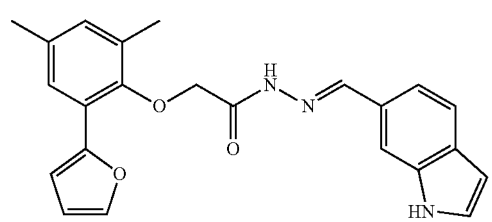 [SMILES: Cc1cc(C)c(OCC(=O)N/N=C/c2ccc3cc[nH]c3c2)c(-c2ccco2)c1] |

TABLE 7-continued

| Compound | Structure |
|---|---|
| 319 | 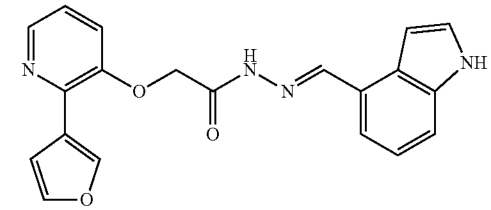 [SMILES: O=C(COc1cccnc1-c1ccoc1)N/N=C/c1cccc2[nH]ccc12] |
| 320 | 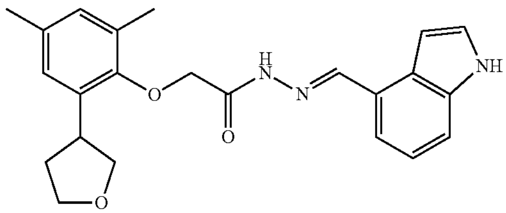 [SMILES: Cc1cc(C)c(OCC(=O)N/N=C/c2cccc3[nH]ccc23)c(C2CCOC2)c1] |
| 322 | 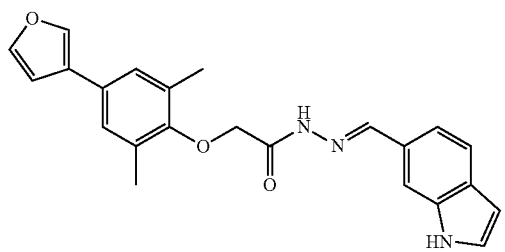 [SMILES: Cc1cc(-c2ccoc2)cc(C)c1OCC(=O)N/N=C/c1ccc2cc[nH]c2c1] |
| 323 | 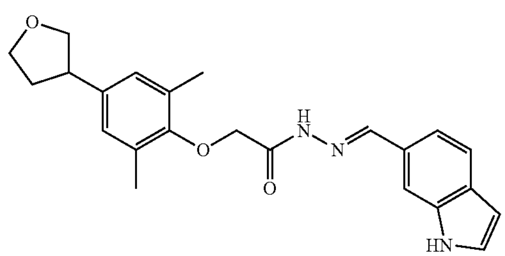 [SMILES: Cc1cc(C2CCOC2)cc(C)c1OCC(=O)N/N=C/c1ccc2cc[nH]c2c1] |

TABLE 8

| Compound | Structure |
|---|---|
| 326 | 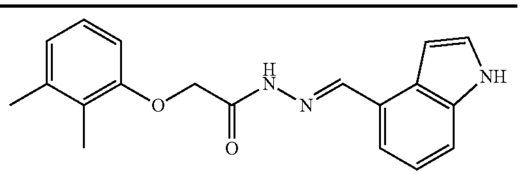 |
| 327 | 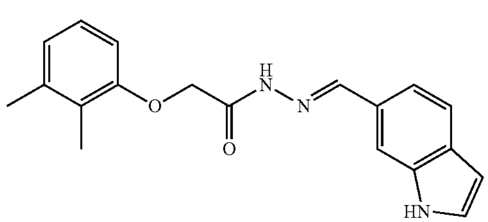 [SMILES: Cc1cccc(OCC(=O)N/N=C/c2ccc3cc[nH]c3c2)c1C] |

TABLE 8-continued

| Compound | Structure |
|---|---|
| 329 | 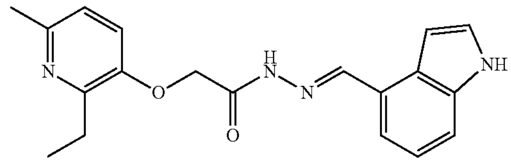 [SMILES: CCc1nc(C)ccc1OCC(=O)N/N=C/c1cccc2[nH]ccc12] |
| 330 | 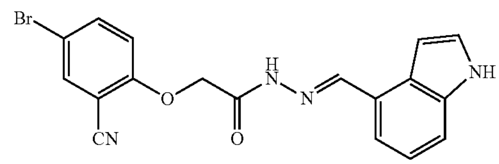 [SMILES: N#Cc1cc(Br)ccc1OCC(=O)N/N=C/c1cccc2[nH]ccc12] |
| 331 | 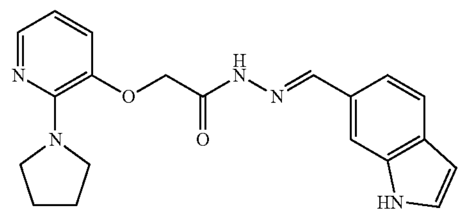 [SMILES: O=C(COc1cccnc1N1CCCC1)N/N=C/c1ccc2cc[nH]c2c1] |
| 332 | 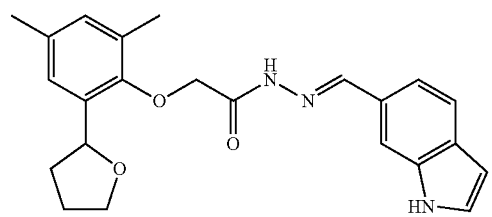 [SMILES: Cc1cc(C)c(OCC(=O)N/N=C/c2ccc3cc[nH]c3c2)c(C2CCCO2)c1] |
| 333 | 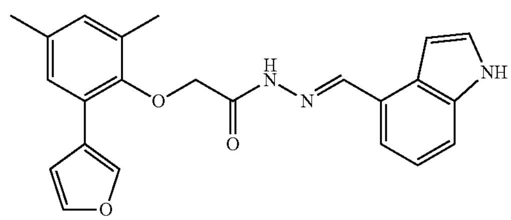 [SMILES: Cc1cc(C)c(OCC(=O)N/N=C/c2cccc3[nH]ccc23)c(-c2ccoc2)c1] |
| 336 | 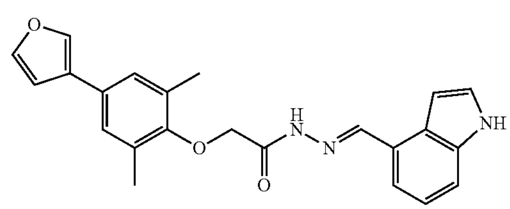 [SMILES: Cc1cc(-c2ccoc2)cc(C)c1OCC(=O)N/N=C/c1cccc2[nH]ccc12] |
| 337 | 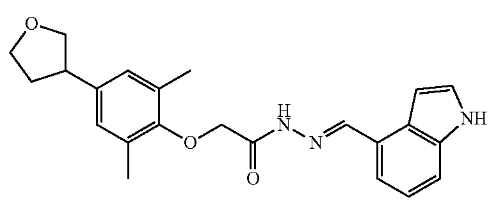 [SMILES: Cc1cc(C2CCOC2)cc(C)c1OCC(=O)N/N=C/c1cccc2[nH]ccc12] |

TABLE 8-continued

| Compound | Structure |
|---|---|
| 343 | 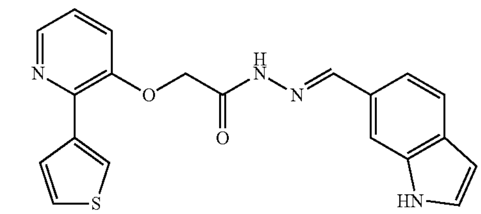 [SMILES: O=C(COc1cccnc1-c1ccsc1)N/N=C/c1ccc2cc[nH]c2c1] |
| 344 | 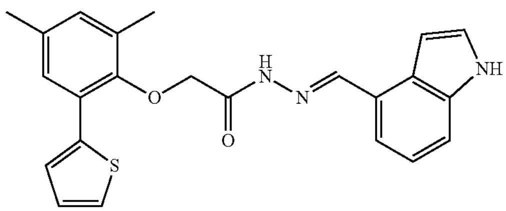 |
| 345 | 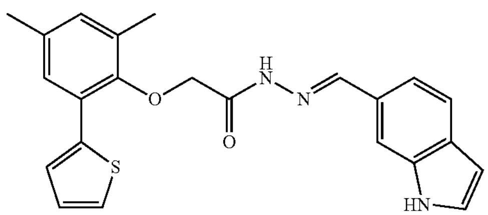 [SMILES: Cc1cc(C)c(OCC(=O)N/N=C/c2ccc3cc[nH]c3c2)c(-c2cccs2)c1] |

TABLE 9

| Compound | Structure |
|---|---|
| 346 | 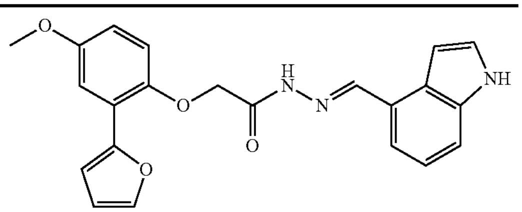 |
| 347 | 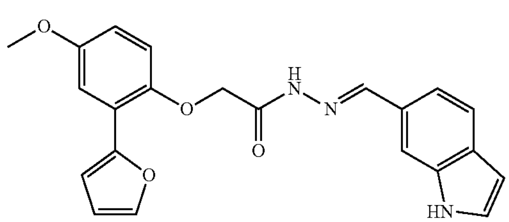 [SMILES: COc1ccc(OCC(=O)N/N=C/c2ccc3cc[nH]c3c2)c(-c2ccco2)c1] |
| 356 | 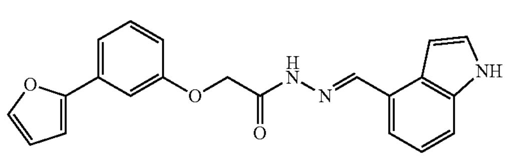 [SMILES: O=C(COc1cccc(-c2ccco2)c1)N/N=C/c1cccc2[nH]ccc12] |
| 358 | 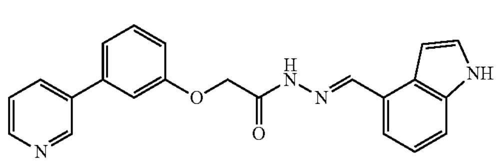 [SMILES: O=C(COc1cccc(-c2cccnc2)c1)N/N=C/c1cccc2[nH]ccc12] |

TABLE 9-continued

| Compound | Structure |
|---|---|
| 359 | 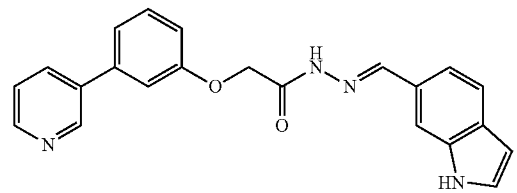 [SMILES: O=C(COc1cccc(-c2cccnc2)c1)N/N=C/c1ccc2cc[nH]c2c1] |
| 375 | 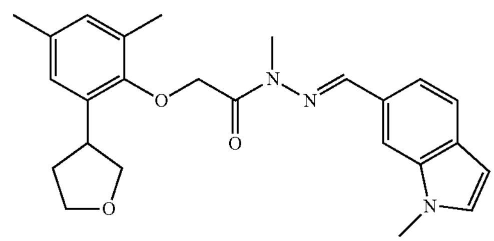 [SMILES: Cc1cc(C)c(OCC(=O)N(C)/N=C/c2ccc3ccn(C)c3c2)c(C2CCOC2)c1] |
| 378 | 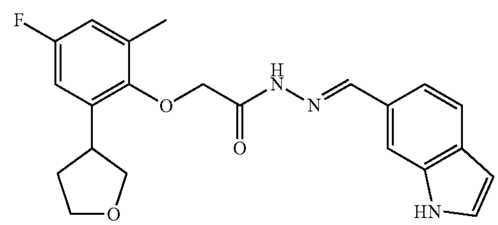 [SMILES: Cc1cc(F)cc(C2CCOC2)c1OCC(=O)N/N=C/c1ccc2cc[nH]c2c1] |
| 379 | 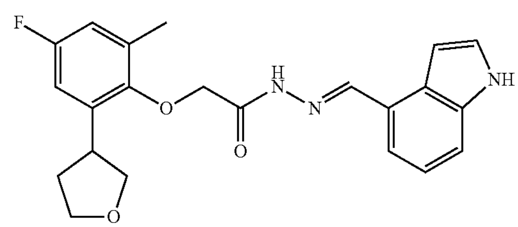 [SMILES: Cc1cc(F)cc(C2CCOC2)c1OCC(=O)N/N=C/c1cccc2[nH]ccc12] |
| 380 | 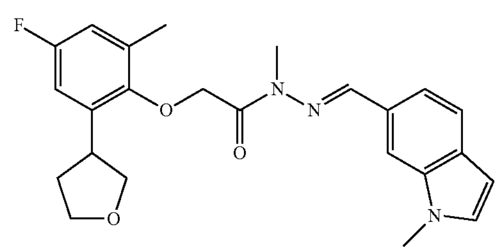 [SMILES: Cc1cc(F)cc(C2CCOC2)c1OCC(=O)N(C)/N=C/c1ccc2ccn(C)c2c1] |
| 457 | 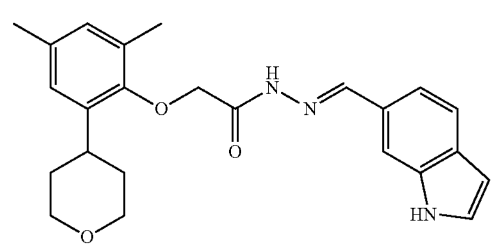 [SMILES: Cc1cc(C)c(OCC(=O)N/N=C/c2ccc3cc[nH]c3c2)c(C2CCOCC2)c1] |

Measurement of Activities of Compounds—Experimental Protocol

EXPERIMENTAL EXAMPLE 1

Measurement of Pro-Apoptotic Activities of Compounds

In order to investigate the effects of the prepared compounds, the apoptosis-inducing effects of the compounds on human T cell acute lymphoblastic leukemia cell line, Jurkat T cells, were evaluated in the following manner.

Jurkat T cells cultured in RPMI medium containing 10% fetal bovine serum (FBS) were collected and stained with trypan blue (Sigma). The results of the staining showed that the viability of the cells was 97% or higher. Then, the cells were centrifuged at 1200 rpm at room temperature for 5 minutes and re-suspended in 10% FBS-containing RPMI medium at a concentration of $1.5 \times 10^5$ cells/mL. 200 μL of the cell suspension was dispensed into each well of a flat bottom 96-well plate (Costar). Then, the cells were treated with 10 μL of the diluted compounds in RPMI medium at final concentrations of 1 M or 5 μM, and incubated in a 5% $CO_2$ incubator at 37° C. for 72 hours. In a vehicle control group, the cells were treated with 10 μL of RPMI medium containing 1% of dimetylsulfoxide (DMSO, Sigma). The incubated cells were harvested, put into 5-mL FACS tubes (BD Falcon), washed with 1 mL of phosphate buffered saline (PBS), and then re-suspended in 0.1 mL of binding buffer (10 mM Hepes-NaOH, pH 7.4, 140 mM NaCl, 2.5 mM $CaCl_2$). The suspended cells were stained with fluorescein isothiocyanate (FITC)-Annexin V (BD Biosciences) and 7-amino-actinomycin D (7-AAD, e-Biosciences) at room temperature for 15 minutes. The stained cells were suspended in 0.3 mL of binding buffer and analyzed by a flow cytometer. Apoptosis was determined by the ratio (%) of cells stained with FITC-Annexin V and 7-AAD among the total cells (see Tables 10 and 11).

TABLE 10

| Compound | Cell Apoptosis Effect to Jurkat T Cell (% in 5 μM) | Compound | Cell Apoptosis Effect to Jurkat T Cell (% in 5 μM) |
| --- | --- | --- | --- |
| Compound 013 | 100 | Compound 014 | 100 |
| Compound 034 | 90 | Compound 457 | 100 |
| Compound 065 | 100 | Compound 072 | 95 |
| Compound 083 | 95 | Compound 092 | 100 |
| Compound 100 | 90 | Compound 108 | 100 |
| Compound 109 | 100 | Compound 112 | 100 |
| Compound 118 | 100 | Compound 121 | 100 |
| Compound 127 | 100 | Compound 133 | 100 |
| Compound 135 | 100 | Compound 136 | 100 |
| Compound 137 | 100 | Compound 138 | 90 |
| Compound 139 | 100 | Compound 146 | 100 |
| Compound 147 | 100 | Compound 149 | 100 |
| Compound 152 | 90 | Compound 155 | 100 |
| Compound 156 | 90 | Compound 157 | 100 |
| Compound 158 | 100 | Compound 159 | 100 |
| Compound 164 | 100 | Compound 177 | 100 |
| Compound 180 | 90 | Compound 182 | 100 |
| Compound 183 | 100 | Compound 184 | 100 |
| Compound 187 | 100 | Compound 190 | 100 |
| Compound 191 | 100 | Compound 192 | 90 |
| Compound 193 | 100 | Compound 194 | 100 |
| Compound 195 | 100 | Compound 196 | 100 |
| Compound 198 | 100 | Compound 201 | 100 |
| Compound 202 | 100 | Compound 205 | 100 |
| Compound 206 | 100 | Compound 209 | 100 |
| Compound 211 | 100 | Compound 217 | 100 |
| Compound 218 | 100 | Compound 227 | 90 |
| Compound 228 | 100 | Compound 229 | 100 |
| Compound 232 | 100 | Compound 233 | 100 |
| Compound 236 | 100 | Compound 237 | 100 |
| Compound 238 | 100 | Compound 239 | 100 |
| Compound 243 | 100 | Compound 244 | 100 |
| Compound 245 | 100 | Compound 252 | 100 |
| Compound 256 | 100 | Compound 258 | 100 |

TABLE 11

| Compound | Jurkat T Cell Apoptosis (% in 5 μM) | Compound | Jurkat T Cell Apoptosis (% in 5 μM) |
| --- | --- | --- | --- |
| Compound 259 | 100 | Compound 260 | 100 |
| Compound 272 | 100 | Compound 279 | 100 |
| Compound 280 | 100 | Compound 286 | 100 |
| Compound 288 | 90 | Compound 289 | 100 |
| Compound 291 | 100 | Compound 293 | 100 |
| Compound 301 | 100 | Compound 302 | 100 |
| Compound 303 | 100 | Compound 304 | 90 |
| Compound 310 | 100 | Compound 311 | 100 |
| Compound 312 | 100 | Compound 313 | 100 |
| Compound 314 | 100 | Compound 317 | 100 |
| Compound 318 | 100 | Compound 319 | 100 |
| Compound 320 | 100 | Compound 322 | 100 |
| Compound 323 | 100 | Compound 326 | 95 |
| Compound 327 | 95 | Compound 329 | 100 |
| Compound 330 | 80 | Compound 331 | 100 |
| Compound 332 | 100 | Compound 333 | 100 |
| Compound 336 | 100 | Compound 337 | 100 |
| Compound 343 | 100 | Compound 344 | 100 |
| Compound 345 | 95 | Compound 346 | 100 |
| Compound 347 | 100 | Compound 356 | 90 |
| Compound 358 | 100 | Compound 359 | 80 |
| Compound 375 | 100 | Compound 378 | 100 |
| Compound 379 | 100 | Compound 380 | 100 |

EXPERIMENTAL EXAMPLE 2

Inhibitory Effect Against Alloantigen-Specific T Cells In Vitro

In order to evaluate the inhibitory effect of compound 229 of the present invention against alloantigen-specific T cells, the following experiment was performed.

The lymph nodes and spleens were aseptically collected from normal C57BL/6 mice (8-12 week old, female, 20±2 g) and were ground with adding of RPMI medium. Then, the ground tissues were passed through a cell strainer (BD Falcon) to make single cell suspensions. The single cell suspension of the spleen was centrifuged at 1200 rpm for 5 minutes. The supernatant was removed, and then 1 mL of ammonium chloride/potassium bicarbonate (ACK) lysis buffer (0.15 M $NH_4Cl$, 1 mM $KHCO_3$, 0.1 mM $Na_2EDTA$) was added to the cells, which were then vortexed for 1 minute and washed with RPMI medium. The erythrocyte-lysed spleen cells were centrifuged together with the lymph node cells, and then re-suspended in 1 mL of magnetic activated cell sorting (MACS) buffer (0.5% BSA, 2 mM EDTA in PBS), and 100 μL of mouse CD90.2 microbeads (Miltenyi Biotec) were added to the cells which were then incubated at 4° C. for 15 minutes. The incubated cell suspension was added with 10 mL of MACS buffer, centrifuged for 5 minutes, washed, and then re-suspended in 2 mL of MACS buffer. The suspended cells were placed in the autoMACS Pro Separator (Miltenyi Biotec), and T cells bound to CD90.2 microbeads were isolated. The isolated T cells were washed with phosphate buffered saline (PBS), and then re-suspended in PBS at a concentration of $1\times10^8$ cells/mL. Normal BALB/c mice (10-12 week old, female, 20-23 g) were irradiated with 950 rad of γ radiation using IBL 437C irradiator (CIS bio international), and then 100 μL of the above-prepared T cell suspension of C57BL/6 mice were injected into the tail vein of the BALB/c mice. At 3 days after the cell injection, the mice were sacrificed, and the spleens were obtained. An erythrocyte-free single cell suspension was made from the obtained spleens in the same manner as described above, and donor T cells were separated from the spleen cell suspension using the autoMACS Pro Separator, thereby preparing secondary responder cells. Meanwhile, T cells were isolated from normal C57BL/6 mice in the same manner as described above, thereby preparing primary responder cells. Each of the primary and secondary responder cells were re-suspended in 1 mL of 1% FBS-containing PBS, and treated with 3 μM of carboxyfluorescein diacetate succinimidyl ester (CFSE, Invitrogen), and then allowed to react at room temperature for 4 minutes. To stop the reaction, cold-stored 5% FBS-containing PBS was added to the cell suspension, followed by washing. The washed cells were re-suspended in 10% FBS-containing RPMI medium at a concentration of $2\times10^6$/mL. The spleens of normal BALB/c mice (8-12 week old, female, 20±2 g) were aseptically collected. The erythrocyte-free spleen cells were prepared in the same manner as described above, and then re-suspended in 1 mL of PBS. 0.5 mg/mL of Mitomycin-C(Sigma) was added to the suspension at a concentration of 0.5 μg/mL, and the cells were incubated at 37° C. for 20 minutes, and then washed three times with an excessive amount of PBS. The washed cells were re-suspended in 10% FBS-containing RPMI medium at a concentration of $4\times10^6$ cells/mL, thereby preparing stimulator cells. The primary and secondary responder cells were mixed with the stimulator cells at a ratio of 1:1 separately, and 200 μL of each cell mixtures was dispensed into each well of a round bottom 96-well plate (Costar). Then, the cells were treated with 10 μL of Compound 229 diluted in RPMI medium at various concentrations, and incubated in a 5% $CO_2$ incubator at 37° C. for 72 hours. In a vehicle control group, the cells were 10 μL of 0.2% DMSO-containing RPMI medium. The incubated cells were placed into 5-mL FACS tubes and washed with 1 mL of fluorescence activated cell sorting (FACS) buffer (1% FBS and 0.1% sodium azide in PBS). The washed cells were re-suspended in 0.1 mL of FACS buffer, and then treated with 1 μg of mouse immunoglobulin G (IgG, e-Biosciences) in order to prevent the non-specific binding of antibody, followed by incubation at 4° C. for 15 minutes. Then, the cells were stained with 0.5 μg of phycoerythrin-conjugated anti-mouse H-$2K^b$ mAb (e-Biosciences) and stained at 4° C. for 30 minutes. After the staining, the cells were washed twice with 1 mL of FACS buffer, re-suspended in 0.1 mL of FACS buffer, stained with 7-AAD at room temperature for 5 minutes. The stained cells were suspended in 0.3 mL of FACS buffer and then analyzed by a flow cytometer. The inhibition of T cell proliferation was determined by measuring the ratio (%) of a cell fraction having a low fluorescence intensity of CFSE among the total live responder cells, and the apoptosis of the T cells was determined by measuring the ratio (%) of cells stained with 7-amino-actinomycin D (7-AAD) among the total responder cells.

Figure 2:
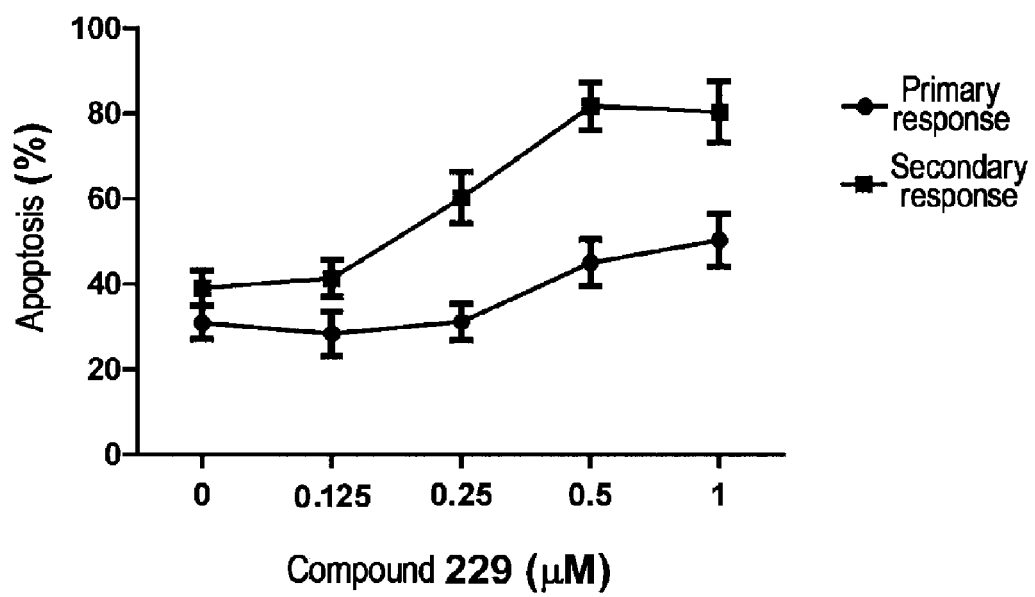

The results indicated that the ratio of T cells ($CFSE^{low}$) that proliferated in response to the alloantigen in vehicle control group was 50% of the total T cells, but was reduced to 3% or less in the test group treated with 0.5 μM or higher of compound 229, suggesting that the proliferation of T cells that responded to the alloantigen was significantly inhibited. In addition, under the conditions of secondary response in which T cells activated primarily by the alloantigen in vivo reacted with the same antigen in vitro, compound 229 effectively inhibited the proliferation of the alloantigen-specific T cells (see FIG. 1). In order to examine whether the inhibitory effect of compound 229 against the alloantigen-specific T cells is attributable to the induction of apoptosis, the cells were stained with 7-AAD and analyzed by flow cytometry. As a result, it was shown that, in the primary response, the apoptosis of the test group treated with 0.5 μM or higher of compound 229 increased by 14-19% compared to that of the vehicle control group, and in the secondary response, the apoptosis of the test group treated with 0.25 μM or higher of compound 229 significantly increased (21-42%) compared to the vehicle control group (see FIG. 2 and Table 12).

TABLE 12

| Concentrations of Compound 229 (μM) | Apoptosis % (mean ± SD) | |
|---|---|---|
| | Primary Response | Secondary Response |
| 0 | 30.91 ± 3.80 | 39.10 ± 4.10 |
| 0.125 | 28.42 ± 5.31 | 41.40 ± 4.35 |
| 0.25 | 31.20 ± 4.26 | 60.27 ± 6.10 ** |
| 0.5 | 45.01 ± 5.48 * | 81.70 ± 5.62 *** |
| 1 | 50.37 ± 6.19 ** | 80.37 ± 7.16 *** |

* $p < 0.05$,
** $p < 0.01$,
*** $p < 0.001$

Thus, compound 229 according to the present invention has an inhibitory effect on the proliferation of all T cells that primarily and secondarily respond to the alloantigen, and this proliferation-inhibitory effect is caused by the induction of apoptosis. In addition, the proliferation of the secondarily activated T cells is inhibited even at a lower concentration of compound 229, and thus compound 229 can be effectively used as an immunosuppressive agent not only for preventing, but also for treating transplant rejection.

EXPERIMENTAL EXAMPLE 3

Inhibitory Effect on Alloantigen-Specific T Cells In Vivo

In order to examine whether compound 229 according to the present invention has an inhibitory effect against T cells that respond to an alloantigen in vivo, an experiment was performed in animal models in the following manner.

Lymph nodes and spleens were aseptically collected from normal C57BL/6-Ly5.1 mice (8-12 week old, female, 20±2 g), and T cells were isolated in the same manner as described in Experimental Example 2, and were then re-suspended in PBS at a concentration of $1\times10^8$ cells/mL. Normal BDF1 mice (10-12 week old, female, 20-23 g) were irradiated with 950 rad of γ radiation, and then 100 μL of the above-prepared T cells of C57BL/6-Ly5.1 mice were injected into the tail vein of the BDF1 mice. Compound 229 was completely dissolved in a Cremophor EL (Sigma)/ethanol mixture (1:1, v/v) in an amount corresponding to 15% (v/v) of the administration volume for intraperitoneal administration and in an amount corresponding to 7.5% (v/v) for oral administration, and the compound solution was diluted in PBS. The dilution was administered intraperitoneally (200 µL/mouse) or orally (500 µL/mouse) every day for 5 days from the day of the cell injection. A vehicle control group was administered with a Cremophor EL-ethanol-PBS mixture in the same ratio and volume as those of the test group. At 6 days after the cell injection, the mice were sacrificed, the spleens were collected from the mice, and erythrocyte-free spleen cells were made in the same manner as described in Experimental Example 2. The spleen cells were stained with trypan blue, and the number of viable cells per organ of each animal was counted. Then, the spleen cells were put into 5 mL FACS tubes and washed with 1 mL of FACS buffer. The cells were re-suspended in 0.1 mL of FACS buffer, and then treated with 1 g of mouse immunoglobulin G in order to prevent the non-specific binding of antibody, followed by incubation at 4° C. for 15 minutes. Then, the cells were stained with 0.5 µg of phycoerythrin-conjugated anti-mouse Ly5.1 mAb (monoclonal antibody) at 4° C. for 30 minutes. The stained cells were washed twice with 1 mL of FACS buffer, re-suspended in 0.3 mL of FACS buffer and analyzed by a flow cytometer. The number of donor T cells in the spleen was determined by measuring the ratio (%) of a donor T cell fraction (Ly5.1$^+$ cells) relative to viable cells per spleen.

Figure 3:
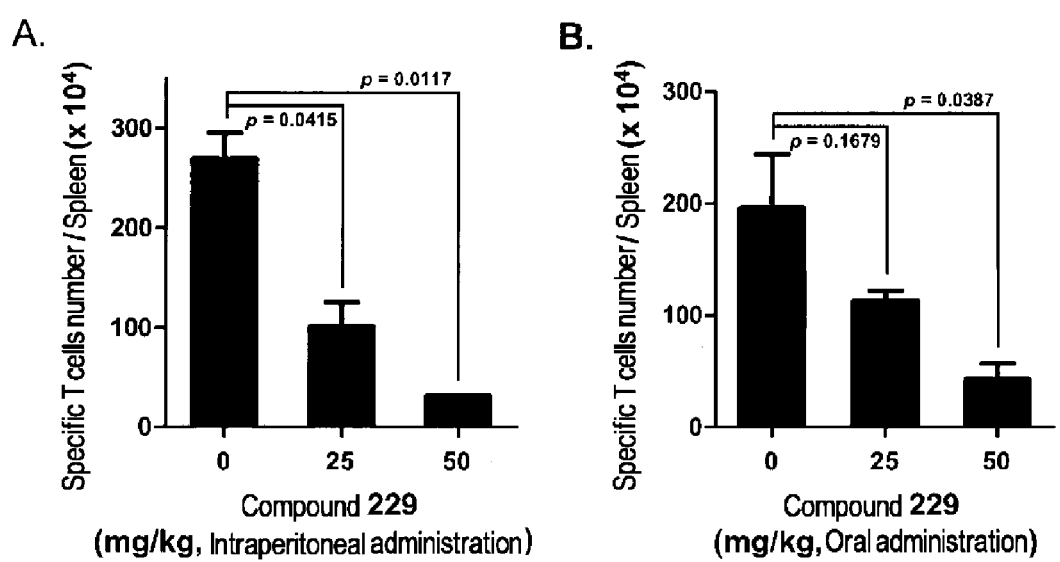
FIG. 3 shows the result of the inhibition activity test against alloantigen-specific T cells of the compound of the present invention.

As a result, it was shown that the number of alloantigen-specific T cells in the spleen of the mice administered intraperitoneally (FIG. 3A) or orally (FIG. 3B) with compound 229 of the present invention significantly decreased compared to that in the vehicle control group in a concentration-dependent manner, and when compound 229 was administered at a dose of 50 mg/kg, the number of activated T cells was significantly decreased, which suggests that the proliferation of T cells that responded to the alloantigen was completely inhibited (see FIGS. 3A and 3B).

Thus, compound 229 according to the present invention has the inhibitory effect on alloantigen-specific T cell in vivo, and is also likely to be developed as an oral immunosuppressive agent.

EXPERIMENTAL EXAMPLE 4

Inhibitory Effect Against Acute Graft-Versus-Host Disease

In order to examine the inhibitory effect of compound 229 of the present invention against acute graft-versus-host disease, acute graft-versus-host disease was induced in mouse model of allogeneic bone marrow transplantation as described below, the mice were treated with compound 229, and the effect of the compound was evaluated.

Lymph nodes, spleens, both femurs and tibias were aseptically collected from normal C57BL/6 mice (8-12 week old, female, 20-23 g), and T cells were isolated from the lymph nodes and spleens in the same manner as described in Experimental Example 2 and were re-suspended in PBS at a concentration of $8\times10^7$ cells/mL. The femurs and tibias were cut at the ends, and the bone marrow was flushed from femurs and tibias with RPMI medium using a syringe (21G for femur and 26G for tibia) to extract the marrow, which was then suspended and passed through a cell strainer to make a single cell suspension. The bone marrow cell suspension was centrifuged at 1200 rpm for 5 minutes, and the supernatant was removed, then the cells were added to 1 mL of ACK lysis buffer and vortexed for 1 minute, followed by washing with RPMI medium. The bone marrow cells collected by centrifugation were re-suspended on 300 µL of MACS buffer, and 30 µL of CD90.2 microbeads were added thereto, followed by incubation at 4° C. for 15 minutes. The incubated cell suspension was added with 5 mL of MACS buffer, centrifuged for 5 minutes, washed, and then re-suspended in 2 mL of MACS buffer. The suspended cells were placed in the autoMACS Pro Separator, and T cells bound to the CD90.2 microbeads were removed. The separated T cell-depleted bone marrow cells (TCD-BM) were washed with PBS and re-suspended in PBS at a concentration of $1\times10^8$ cells/mL. Normal BDF1 mice (10-12 week old, female, 20-23 g) were irradiated with 850 rad of γ radiation using an irradiator, and then 100 µL of a graft obtained by mixing the C57BL/6 mouse T cells and the TCD-BM at a ratio of 1:1 was injected into the tail vein of the BDF1 mice. In a group treated with compound 229 of the present invention, compound 229 was completely dissolved in a Cremophor EL-ethanol mixture (1:1, v/v) in an amount corresponding to 15% (v/v) of the administration volume, after which the compound solution was diluted in PBS, and the dilution was administered intraperitoneally to each mouse at a dose of 25 mg/kg daily for 10 days from the day of the graft injection. Meanwhile, Tacrolimus that is a currently clinically used immunosuppressive agent was administered to mice of another group in the same amount as compound 229 in order to compare the inhibitory effect on acute graft-versus-host disease, and mice of a vehicle control group were administered with 200 µL of a Cremophor EL-ethanol-PBS (7.5:7.5:85, v/v/v) in the same manner as the treated groups. Then, the survival of mice was monitored daily, and the severity of GVHD was assessed twice a week with clinical GVHD scoring system for each a decrease in weight loss, hunched posture, decreased activity, fur ruffling and skin lesions. Each parameters were scored on a 3-point (0 to 2) scale.

Figure 4:
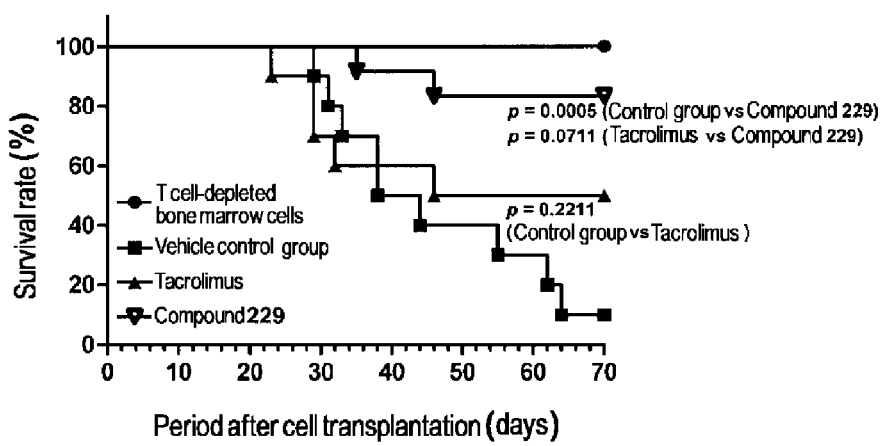
FIG. 4 shows the result of the inhibition activity test against acute graft-versus-host disease of the compound of the present invention.
Figure 4:
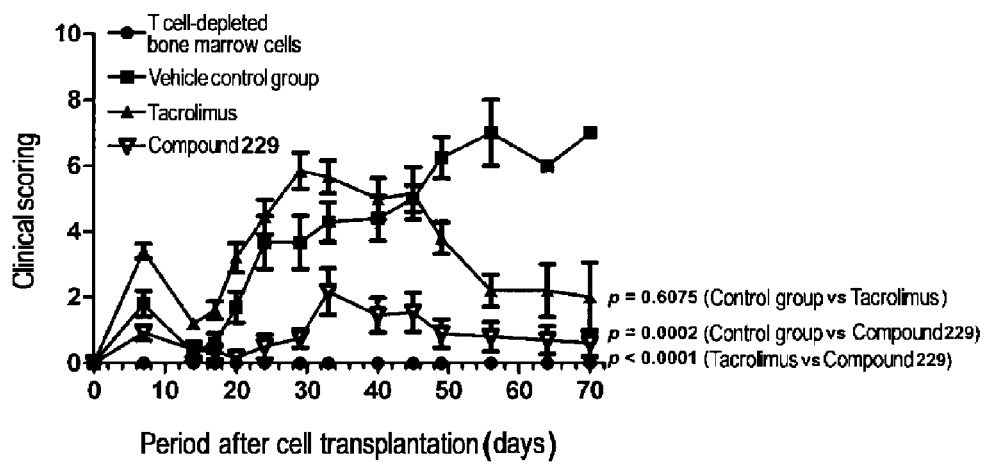

As a result, the mice of the vehicle control group started to die from 29 days after cell transplantation and showed a survival rate of 10% at day 70, and the mice of the group treated with Tacrolimus started to die from 23 days and finally showed a survival rate of 50%. Meanwhile, the group treated with compound 229 of the present invention showed mouse death at 35 days and 46 days after cell transplantation, but finally showed a mouse survival rate of 80%, which was significantly higher than that of the vehicle control group. Also, the survival rate of the group treated with compound 229 increased compared to that of the Tacrolimus-treated group, but this increase was not significant (see FIG. 4A). In the results of evaluating the severity of GVHD using the clinical scoring system, in the mice treated with Tacrolimus, ruffled fur and severe skin lesions were observed, whereas in the mice treated with compound 229, slight symptoms of GVHD, including a slight weight loss, were observed. This reduction in GVHD symptoms by treatment with compound 229 was statistically significant (see FIG. 4B).

Accordingly, compound 229 of the present invention has the inhibitory effect on GVHD in mouse models, and the inhibitory effect of compound 229 is superior to that of the conventional immunosuppressive agent Tacrolimus. Thus, compound 229 of the present invention can be effectively used as a novel immunosuppressive agent.

EXPERIMENTAL EXAMPLE 5

Effect on Treatment of Multiple Sclerosis

In order to examine the therapeutic effect of compound 229 of the present invention against multiple sclerosis, Experimental Autoimmune Encephalomyelitis (EAE) was induced in murine models as described below, the mice were treated with compound 229, and the effect of the compound was evaluated.

At the first day of induction, myelin oligodendrocyte glycoprotein$_{35-55}$ (MOG$_{35-55}$, Peptron) (200 ug), *mycobacterium tuberculosis* (Difco, Cat No. 231141) (500 μg) and complete Freund's adjuvant (Sigma Aldrich, Cat No. F5506) were mixed with each other and immersed for 5 minutes. 0.1 mL of the immersed peptide was injected subcutaneously into both the flanks of each of C57BL/6 mice (9 week old, female, 18±2 g), followed by that 0.1 mg of pertussis toxin (Sigma Aldrich, Cat No. P2980) (200 ng) was injected by intravenously. At 2 days, the same amount of pertussis toxin was administered intravenously. Whether the immersion leaked from the injected portion of the mice was checked, and whether EAE was induced was also examined by visual observation from 7 days.

Compound 229 and Fingolimod that is currently clinically used for the treatment of multiple sclerosis were completely dissolved in a Cremophor EL-ethanol mixture (1:1, v/v) in an amount corresponding to 7.5% (v/v) of the administration volume, and the compound solution was diluted in PBS. The two groups of the mice were administered orally with 200 μL of the diluted solution of compound 229 at each doses of 25 and 50 mg/kg separately, and the third group of the mice was administered orally with 200 μL of the diluted solution of fingolimode at a dose of 1 mg/kg on a daily basis from 17 days to 37 days (for total 21 times) after starting of the experiment. In a vehicle control group, 200 μL of a Cremophor EL-ethanol-PBS mixture (3.75:3.75:92.5, v/v/v) was administered to each mouse in the same manner as the treated group. The index of EAE was recorded daily based on visual observation using a severity index system (6-point (0 to 5) scale) from 7 days of the experiment. The symptoms of multiple sclerosis were evaluated based on the following criteria:

0: no abnormality;
1: limp tail;
2: limp tail and hind limb weakness;
3: hind limb paralysis;
4: hind limb paralysis and forelimb weakness; and
5: Moribund.

Figure 5:
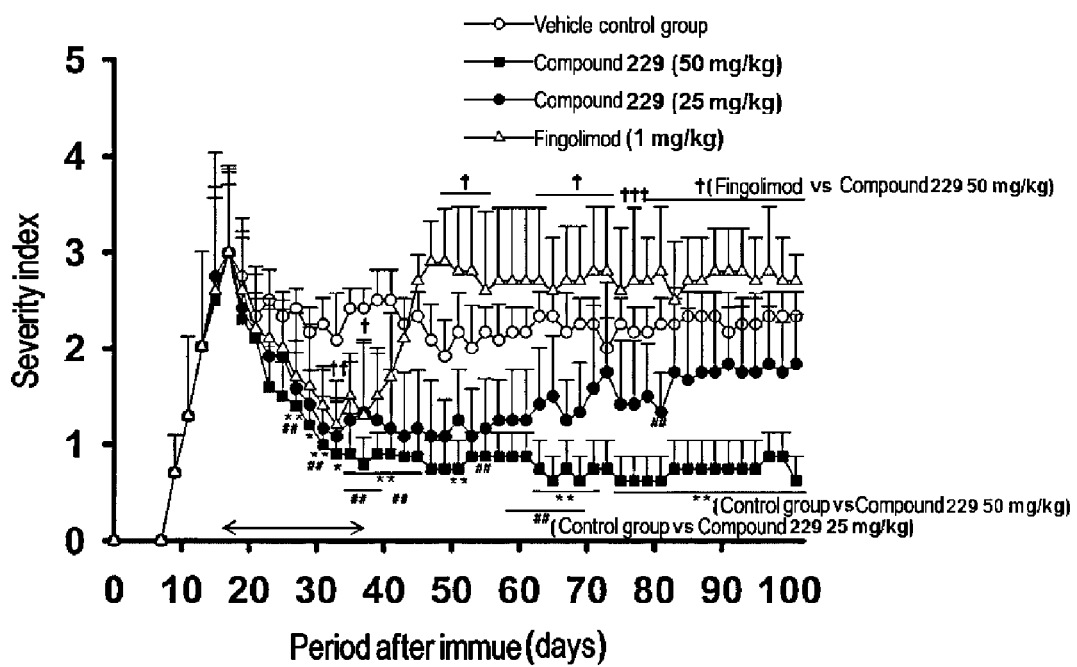
FIG. 5 shows the result of the treatment activity test for multiple sclerosis of the compound of the present invention.

The results of the analysis indicated that, in all the test groups, EAE was developed from 7 days of the experiment, and the severity index at 17 days of the experiment was 3±1.25, indicating that a 100% acute reaction was induced. In the case of the mice of the vehicle control group, the severity index was 3±1 at 17 days of the experiment, 2.5±0.75 at 39 days (chronic reaction period) and 2.33±0.25 at 101 days of the experiment. The vehicle control group showed a relapse-remitting pattern and a high severity index throughout the experiment period. In the Fingolimod-treated group, the severity index was 3±1 at 17 days of the experiment, but was 1.5±0.5 at 39 days of the experiment, indicating that the Fingolimod-treated group showed an alleviated acute reaction and a mild chronic reaction therapeutic effect, compared to the vehicle control group. However, the Fingolimod-treated group showed an increase in the severity index from 39 days of the experiment after completion of administration of the drug and showed a high severity index of 2.7±0.25 at 101 days of the experiment. Also, the group treated with 25 mg/kg of compound 229 of the present invention showed a severity index of 3±1 at 17 days of the experiment, which was similar to that of the vehicle control group, but it showed severity index of 1.25±0.75 at 39 days of the experiment and 1.17±0.75 at 55 days of the experiment, suggesting that a statistically significant therapeutic effect compared to that in the vehicle control group appeared. However, in the group treated with 25 mg/kg of compound 229, the severity index started to increase from 57 days of the experiment and was 1.83±0.5 at 101 days of the experiment, which was lower than that of the vehicle control group, but was slightly higher than that in the initial stage of the experiment (#, p<0.05; ##, p<0.01; and ###, p<0.001, compared to the vehicle control group; see FIG. 5). Moreover, the group treated with 50 mg/kg of compound 229 of the present invention showed a severity index of 3±0.75 at 17 days of the experiment, which was similar to that of the vehicle control group, but it showed severity index of 0.9±0.25 at 39 days of the experiment and 0.63±0.25 at 101 days of the experiment, suggesting that a statistically significant therapeutic effect compared to that in the vehicle control group appeared (*, p<0.05; , p<0.01; and *, p<0.001, compared to the vehicle control group; see FIG. 5). In the group treated with 50 mg/kg of compound 229, the therapeutic effect was continuously maintained after oral administration of the compound, and this effect did statistically significant differ from that in the Fingolimod-treated group at 49 days of the experiment (†, p<0.05; †, p<0.01; and †††, p<0.001, compared to the Fingolimod-treated group; see FIG. 5). When compound 229 of the present invention was used at a dose of 25 mg/kg, it showed an excellent therapeutic effect in the initial stage, but showed a slightly insignificant effect on the prevention of relapse, and when compound 229 of the present invention was used at a dose of 50 mg/kg, it showed a therapeutic effect in the initial stage and a continuous effect on the prevention of relapse. Consequently, compound 229 of the present invention has a therapeutic effect against EAE in the murine models, and the therapeutic effect thereof is superior and maintained for a long period of time compared to Fingolimod that is a conventional therapeutic agent against multiple sclerosis. Thus, compound 229 of the present invention is a novel oral therapeutic agent against multiple sclerosis, which can present a more attractive therapeutic strategy.

EXPERIMENTAL EXAMPLE 6

Effect on Apoptosis of Lymphoid Malignancy Cell Lines

In order to evaluate the inhibitory effects of compound 457 against lymphoid malignancy cell lines, the following experiment was performed.

Each of the acute T cell leukemia cell lines Jurkat, Molt4 and CCRF-CEM, the acute B cell leukemia cell line Raji and the multiple sclerosis cell lines KMS11, KMS12BM, KMS26, KMS28BM, and IM9 was re-suspended in 10% FBS-containing RPMI medium at a concentration of 1.5×10$^5$ cells/mL, and 200 μL of each of the cell suspensions was cultured in a flat bottom 96-well plate (Costar). The acute NK cell lymphoma cell line NK-92MI was re-suspended in α-MEM medium (supplemented with 20% FBS, 1×MEM vitamine solution, 50 μM 2-mercaptoethanol and 1× penicillin/streptomycin) at a concentration of 1.5×10$^5$ cells/mL, and 200 μL of the cell suspension was cultured in a flat bottom 96-well plate. The cells in each well was treated with 10 μL of each of 0.1, 0.25, 0.5, 0.75 and 1 μM of the compound diluted with RPMI medium, followed by that the cells were incubated in a 5% $CO_2$ incubator at 37° C. for 24 hours. In a vehicle control group, cells were treated with 10 μL of medium containing 0.05% dimetylsulfoxide (DMSO, Sigma).

The cells were collected, and then the apoptosis thereof was analyzed by a flow cytometer after staining with Annexin V-7-AAD. The incubated cells were collected, placed in a 5-mL FACS tube (BD Falcon) and washed with 1 mL of fluorescence activated cell sorting (FACS) buffer (1%. FBS and 0.1% sodium azaide in PBS). The cells were re-suspended in 0.1 mL of FACS buffer, followed by that the cells were treated and stained with phycoerythrin-Annexin V at room temperature for 10 minutes. After 10 minutes of staining, the cells were treated and stained with 7-AAD at room temperature for 5 minutes. The stained cells were suspended in 0.3 mL of FACS buffer, and then analyzed by a flow cytometer. As shown in Tables 12 to 15, compounds 065, 108, 229 and 457 of the present invention showed the effects of inducing the apoptosis of various lymphoid malignancy cells. Thus, compounds 065, 108, 229 and 457 of the present invention can be used as a novel anti-lymphoid malignancy drug.

TABLE 13

| Cell Line | Tumor Source | Administration Dose of Compound 065 (mean ± SD, μmol/L) Lethal Dose 50 (Apoptosis) |
|---|---|---|
| Jurkat | Acute T cell leukemia | 0.79 ± 0.01 |
| Molt4 | Acute T cell leukemia | 1.58 ± 0.03 |
| IM9 | Multiple myeloma | 1.21 ± 0.01 |

TABLE 14

| Cell Line | Tumor Source | Administration Dose of Compound 108 (mean ± SD, μmol/L) Lethal Dose 50 (Apoptosis) |
|---|---|---|
| Jurkat | Acute T cell leukemia | 0.78 ± 0.04 |
| Molt4 | Acute T cell leukemia | 1.38 ± 0.04 |
| IM9 | Multiple myeloma | 1.41 ± 0.03 |

TABLE 15

| Cell Line | Tumor Source | Administration Dose of Compound 229 (mean ± SD, μmol/L) Lethal Dose 50 (Apoptosis) |
|---|---|---|
| Jurkat | Acute T cell leukemia | 0.62 ± 0.00 |
| Molt4 | Acute T cell leukemia | 1.30 ± 0.05 |
| KMS11 | Multiple myeloma | 0.35 ± 0.09 |
| KMS12BM | Multiple myeloma | 0.94 ± 0.09 |
| KMS20 | Multiple myeloma | 0.74 ± 0.05 |
| KMS26 | Multiple myeloma | 1.31 ± 0.35 |
| KMS28BM | Multiple myeloma | 0.49 ± 0.08 |
| IM9 | Multiple myeloma | 0.90 ± 0.03 |

TABLE 16

| Cell Line | Tumor Source | Administration Dose of Compound 457 (mean ± SD, μmol/L) Lethal Dose 50 (Apoptosis) |
|---|---|---|
| Jurkat | Acute T cell leukemia | 0.20 ± 0.01 |
| Molt4 | Acute T cell leukemia | 0.25 ± 0.11 |
| CCRF-CEM | Acute T cell leukemia | 0.17 ± 0.00 |
| Raji | Acute B cell leukemia | 0.68 ± 0.05 |
| KMS11 | Multiple myeloma | 0.63 ± 0.31 |
| KMS12BM | Multiple myeloma | 0.22 ± 0.02 |

TABLE 16-continued

| Cell Line | Tumor Source | Administration Dose of Compound 457 (mean ± SD, μmol/L) Lethal Dose 50 (Apoptosis) |
|---|---|---|
| KMS26 | Multiple myeloma | 0.55 ± 0.12 |
| KMS28BM | Multiple myeloma | 0.47 ± 0.06 |
| IM9 | Multiple myeloma | 0.38 ± 0.01 |
| NK-92MI | Acute NK cell lymphoma | 0.46 ± 0.01 |

Experimental Example 7

Toxicity Test

To ICR male mice, a suspension of Compound 229 in 0.5% methylcellulose solution was administered orally once by each doses of 10 mg/kg, 50 mg/kg and 100 mg/kg, and the survival rate and body weight of the mice were investigated for 7 days. After such administration, mouse death or not, clinical condition and body weight change were monitored. Hematology test and biochemical examination of blood were carried out. After conducting autopsies, abnormality or not of organs in the abdominal and thoracic cavities were observed with the naked eye.

As the result, there is not any notable clinical condition or dead mouse. In the body weight change, the hematology test, the biochemical examination of blood, and the examination of autopsy, any change due to toxicity was also not observed. Such that, Compound 229 did not show any change due to toxicity until the dose of 100 mg/kg.

Therefore, Compound 229 has the lethal dose 50 (LD50) of 100 mg/kg, so it is safe.

The invention claimed is:

1. A compound of formula 1, a stereoisomer thereof, or a pharmaceutically acceptable salt thereof:

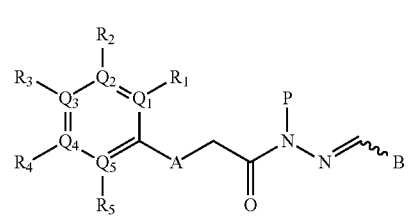

[Formula 1]

Wherein,

A is N-H, O or S;

$Q_1$, $Q_2$, $Q_3$, $Q_4$ and $Q_5$ are each independently C or N;

$R_1$, $R_2$, $R_3$, $R_4$ and $R_5$ are each independently absent, —H, —CF$_3$, —F, —Br, —Cl, cyanide, —CH$_2$OH, —(CO)NH$_2$, —(C$_1$-C$_6$)alkyl, —(C$_{1-3}$)alkoxy, —NH$_2$, —N(CH$_3$)$_2$, or 4, 5 or 6-membered heteroaryl or heterocycloalkyl comprising 1 to 3 members selected from the group consisting of N, O and S (said heteroaryl or heterocycloalkyl has at least one substituent selected from —H, halogen and amine);

P is —H, —(C$_1$-C$_3$)OH, —(C$_1$-C$_6$)alkyl, —(CO)(C$_1$-C$_6$)alkyl;

101

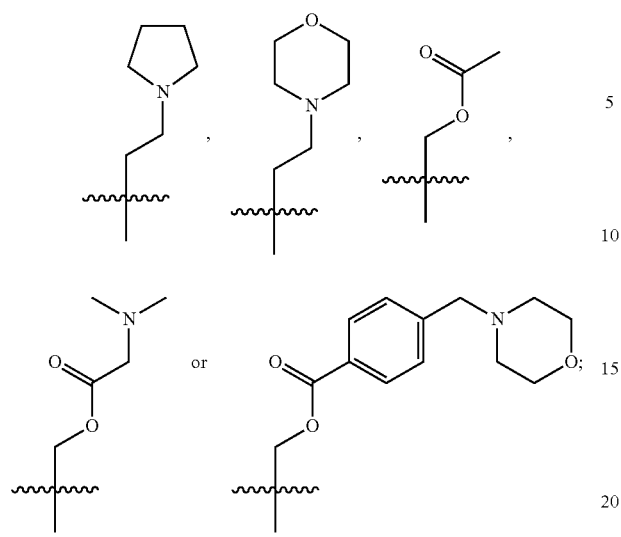

and

B is selected from the group consisting of:

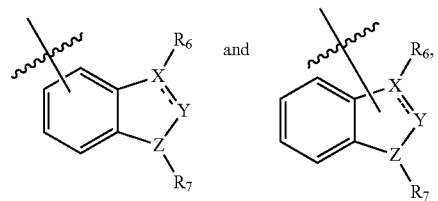

wherein, X, Y and Z are each independently C, N or S, and R$_6$ and R$_7$ are each independently absent, —H, —Br, —(C$_1$-C$_6$)alkyl, —(C$_1$-C$_3$)OH,

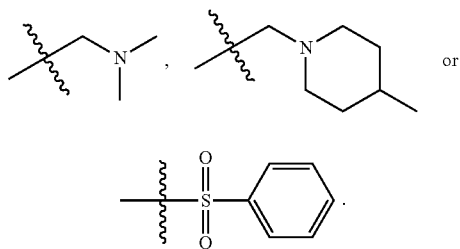

2. The compound according to claim 1, a stereoisomer thereof, or a pharmaceutically acceptable salt thereof, wherein A is N—H, O or S;

Q$_1$, Q$_2$, Q$_3$, Q$_4$ and Q$_5$ are C;

R$_2$ and R$_4$ is H;

R$_1$, R$_3$ and R$_5$ are each independently —H, —F, —Br, —Cl, methyl, ethyl, —CH$_2$OH, cyanide, —NH$_2$, or 4, 5 or 6-membered heteroaryl or heterocycloalkyl comprising 1 to 3 members selected from the group consisting of N, O and S;

P is —H, methyl, —CH$_2$OH, —CH$_2$CH$_2$OH,

102

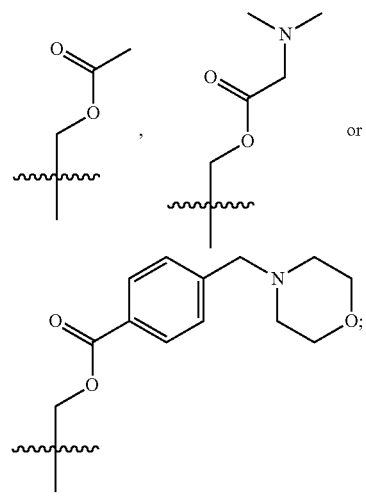

and

B is selected from the group consisting of:

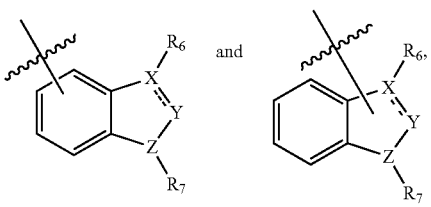

wherein X and Y is C,

Z is N, and

R$_6$ and R$_7$ are each independently —H, methyl or —CH$_2$CH$_2$OH.

3. The compound according to claim 1, a stereoisomer thereof, or a pharmaceutically acceptable salt thereof, wherein the compound is selected from the group consisting of:

(E)-N'-((1H-indol-4-yl)methylene)-2-(mesityloxy)acetohydrazide;

(E)-N'-((1H-indol-5-yl)methylene)-2-(4-bromo-2,6-dimethylphenoxy)acetohydrazide;

(E)-N'-((1H-indol-6-yl)methylene)-2-(mesityloxy)acetohydrazide;

(E)-N'-((1H-indol-2-yl)methylene)-2-(mesityloxy)acetohydrazide;

(E)-N'-((1H-indol-4-yl)methylene)-2-(4-bromo-2,6-dimethylphenoxy)acetohydrazide;

(E)-N'-((1H-indol-6-yl)methylene)-2-(4-bromo-2,6-dimethylphenoxy)acetohydrazide;

(E)-N'-((1H-indol-4-yl)methylene)-2-(mesitylamino)acetohydrazide;

(E)-N'-((1H-indol-4-yl)methylene)-2-(2,6-dimethyl-4-(pyridin-3-yl)phenoxy)acetohydrazide;

(E)-N'-((1H-indol-6-yl)methylene)-2-(2,6-dimethyl-4-(pyridin-3-yl)phenoxy)acetohydrazide;

(E)-N'-((1H-indol-4-yl)methylene)-2-(2-(pyridin-3-yl)phenoxy)acetohydrazide;

(E)-N'-((1H-indol-4-yl)methylene)-2-(mesitylthio)acetohydrazide;

(E)-N'-((1H-indol-4-yl)methylene)-2-(2,6-dimethyl-4-(pyrimidin-5-yl)phenoxy)acetohydrazide;

(E)-N'-((1H-indol-4-yl)methylene)-2-(4-chloro-2,6-dimethylphenoxy)acetohydrazide;
(E)-N'-((1H-indol-3-yl)methylene)-2-(4-chloro-2,6-dimethylphenoxy)acetohydrazide;
(E)-N'-((1H-indol-6-yl)methylene)-2-(4-chloro-2,6-dimethylphenoxy)acetohydrazide;
(E)-N'-((1H-indol-3-yl)methylene)-2-(mesitylthio)acetohydrazide;
(E)-N'-((1H-indol-6-yl)methylene)-2-(mesitylthio)acetohydrazide;
(E)-2-(mesityloxy)-N-methyl-N'-((1-methyl-1H-indol-4-yl)methylene)acetohydrazide;
(E)-N'-((1H-indol-4-yl)methylene)-N-(2-hydroxyethyl)-2-(mesityloxy)acetohydrazide;
(E)-N'-((1-(2-hydroxyethyl)-1H-indol-4-yl)methylene)-2-(mesityloxy)acetohydrazide;
(E)-N'-((1H-indol-4-yl)methylene)-2-(2,4-dimethyl-6-(pyridin-3-yl)phenoxy)acetohydrazide;
(E)-N'-((1H-indol-6-yl)methylene)-2-(2,4-dimethyl-6-(pyridin-3-yl)phenoxy)acetohydrazide;
(E)-N'-((1H-indol-5-yl)methylene)-2-(2,4-dimethyl-6-(pyridin-3-yl)phenoxy)acetohydrazide;
(E)-N'-((1H-indol-4-yl)methylene)-2-((2-methylpyridin-3-yl)oxy)acetohydrazide;
(E)-N'-((1H-indol-6-yl)methylene)-N-(2-hydroxyethyl)-2-(mesityloxy)acetohydrazide;
(E)-N'-((1H-indol-6-yl)methylene)-2-(2,4-dimethyl-6-(pyridin-4-yl)phenoxy)acetohydrazide;
(E)-N'-((1H-indol-6-yl)methylene)-2-(2-(furan-3-yl)-4,6-dimethylphenoxy)acetohydrazide;
(E)-N'-((1H-indol-4-yl)methylene)-2-(4-(hydroxymethyl)-2,6-dimethylphenoxy)acetohydrazide;
(E)-N'-((1H-indol-6-yl)methylene)-2-(4-(hydroxymethyl)-2,6-dimethylphenoxy)acetohydrazide;
(E)-N'-((1H-indol-6-yl)methylene)-2-(2,4-dimethyl-6-(tetrahydrofuran-3-yl)phenoxy)acetohydrazide;
(E)-N'-((1H-indol-4-yl)methylene)-2-(4-amino-2,6-dimethylphenoxy)acetohydrazide;
(E)-N'-((1H-indol-6-yl)methylene)-N-(hydroxymethyl)-2-(mesityloxy)acetohydrazide;
(E)-2-((1H-indol-6-yl)methylene)-1-(2-(mesityloxy)acetyl)hydrazinyl)methyl 2-(dimethylamino)acetate;
(E)-N'-((1H-indol-6-yl)methylene)-2-(4-cyano-2,6-dimethylphenoxy)acetohydrazide;
(E)-2-((1H-indol-4-yl)methylene)-1-(2-(mesityloxy)acety)phydrazinyl)methyl 2-(dimethylamino)acetate;
(E)-N'-((1H-indol-6-yl)methylene)-N-acetyl-2-(mesityloxy)acetohydrazide;
(E)-N'-((1H-indol-4-yl)methylene)-N-(hydroxymethyl)-2-(mesityloxy)acetohydrazide;
(E)-2-((1H-indol-4-yl)methylene)-1-(2-(mesityloxy)acety)phydrazinyl)methyl 4-(morpholinomethyl)benzoate;
(E)-2-((1H-indol-6-yl)methylene)-1-(2-(mesityloxy)acety)phydrazinyl)methyl acetate;
(E)-N'-((1H-indol-6-yl)methylene)-2-(2,6-dimethylphenoxy)acetohydrazide;
(E)-N'-((1H-indol-4-yl)methylene)-2-(2-bromo-4,6-dimethylphenoxy)acetohydrazide;
(E)-N'-((1H-indol-6-yl)methylene)-2-(2-bromo-4,6-dimethylphenoxy)acetohydrazide;
(E)-2-((1H-indol-6-yl)methylene)-1-(2-(mesityloxy)acety)phydrazinyl)methyl 4-(morpholinomethyl)benzoate;
(E)-N'-((1H-indol-6-yl)methylene)-2-(2-methyl-6-(tetrahydrofuran-3-yl)phenoxy)acetohydrazide;
(E)-N'-((1H-indol-4-yl)methylene)-2-(2-methyl-6-(tetrahydrofuran-3-yl)phenoxy)acetohydrazide;
(E)-N'-((1H-indol-6-yl)methylene)-2-(2-(furan-3-yl)-6-methylphenoxy)acetohydrazide;
(E)-N'-((1H-indol-4-yl)methylene)-2-(2-(furan-3-yl)-6-methylphenoxy)acetohydrazide;
(E)-N'-((1H-indol-4-yl)methylene)-2-(2-(furan-2-yl)-4,6-dimethylphenoxy)acetohydrazide;
(E)-N'-((1H-indol-4-yl)methylene)-2-((2-(furan-3-yl)pyridin-3-yl)oxy)acetohydrazide;
(E)-N'-((1H-indol-4-yl)methylene)-2-(2,4-dimethyl-6-(tetrahydrofuran-3-yl)phenoxy)acetohydrazide;
(E)-N'-((1H-indol-6-yl)methylene)-2-(4-(furan-3-yl)-2,6-dimethylphenoxy)acetohydrazide;
(E)-N'-((1H-indol-6-yl)methylene)-2-(2,6-dimethyl-4-(tetrahydrofuran-3-yl)phenoxy)acetohydrazide;
(E)-N'-((1H-indol-4-yl)methylene)-2-((2-ethyl-6-methylpyridin-3-yl)oxy)acetohydrazide;
(E)-N'-((1H-indol-6-yl)methylene)-2-((2-(pyrrolidin-l-yl)pyridin-3-yl)oxy)acetohydrazide;
(E)-N'-((1H-indol-6-yl)methylene)-2-(2,4-dimethyl-6-(tetrahydrofuran-2-yl)phenoxy)acetohydrazide;
(E)-N'-((1H-indol-4-yl)methylene)-2-(2-(furan-3-yl)-4,6-dimethylphenoxy)acetohydrazide;
(E)-N'-((1H-indol-4-yl)methylene)-2-(4-(furan-3-yl)-2,6-dimethylphenoxy)acetohydrazide;
(E)-N'-((1H-indol-4-yl)methylene)-2-(2,6-dimethyl-4-(tetrahydrofuran-3-yl)phenoxy)acetohydrazide;
(E)-N'-((1H-indol-6-yl)methylene)-2-((2-(thiophen-3-yl)pyridin-3-yl)oxy)acetohydrazide;
(E)-N'-((1H-indol-4-yl)methylene)-2-(2,4-dimethyl-6-(thiophen-2-yl)phenoxy)acetohydrazide;
(E)-N'-((1H-indol-4-yl)methylene)-2-(2-(furan-2-yl)-4-methoxyphenoxy)acetohydrazide;
(E)-2-(2,4-dimethyl-6-(tetrahydrofuran-3-yl)phenoxy)-N-methyl-N'((1-methyl-1H-indol-6-yl)methylene)acetohydrazide;
(E)-N'-((1H-indol-6-yl)methylene)-2-(4-fluoro-2-methyl-6-(tetrahydrofuran-3-yl)phenoxy)acetohydrazide;
(E)-N'-((1H-indol-4-yl)methylene)-2-(4-fluoro-2-methyl-6-(tetrahydrofuran-3-yl)phenoxy)acetohydrazide;
(E)-2-(4-fluoro-2-methyl-6-(tetrahydrofuran-3-yl)phenoxy)-N-methyl-N'-((1-methyl-1H-indol-6-yl)methylene)acetohydrazide; and
(E)-N'-((1H-indol-6-yl)methylene)-2-(2,4-dimethyl-6-(tetrahydro-2H-pyran-4-yl)phenoxy)acetohydrazide.

4. The compound according to claim 3, a stereoisomer thereof, or a pharmaceutically acceptable salt thereof, wherein the compound is selected from the group consisting of:
(E)-N'-((1H-indol-4-yl)methylene)-2-(mesityloxy)acetohydrazide;
(E)-N'-((1H-indol-6-yl)methylene)-2-(mesityloxy)acetohydrazide;
(E)-N'-((1H-indol-6-yl)methylene)-2-(2,4-dimethyl-6-(tetrahydrofuran-3-yl)phenoxy)acetohydrazide; and
(E)-N'-((1H-indol-6-yl)methylene)-2-(2,4-dimethyl-6-(tetrahydro-2H-pyran-4-yl)phenoxy)acetohydrazide.

5. A pharmaceutical composition comprising the compound according to claim 1, a stereoisomer thereof or a pharmaceutically acceptable salt thereof; and a pharmaceutically acceptable carrier.

6. The pharmaceutical composition according to claim 5, wherein the composition is used for treating acute T cell leukemia, multiple myeloma, acute B cell leukemia, acute NK cell lymphoma, multiple sclerosis, and acute graft-versus-host disease (GVHD).

7. A pharmaceutical composition comprising the compound according to claim 2, a stereoisomer thereof or a pharmaceutically acceptable salt thereof; and a pharmaceutically acceptable carrier.

8. The pharmaceutical composition according to claim 7, wherein the composition is used for treating acute T cell leukemia, multiple myeloma, acute B cell leukemia, acute NK cell lymphoma, multiple sclerosis, and acute graft-versus-host disease (GVHD).

* * * * *

UNITED STATES PATENT AND TRADEMARK OFFICE
CERTIFICATE OF CORRECTION

PATENT NO.        : 9,447,083 B2                       Page 1 of 1
APPLICATION NO.   : 14/424749
DATED             : September 20, 2016
INVENTOR(S)       : Choi et al.

It is certified that error appears in the above-identified patent and that said Letters Patent is hereby corrected as shown below:

In the Claims

Column 103, Line 47: Claim 3, Delete "acety)phydrazinyl)methyl" and insert
-- acetyl)hydrazinyl)methyl --

Column 103, Line 53: Claim 3, Delete "acety)phydrazinyl)methyl" and insert
-- acetyl)hydrazinyl)methyl --

Column 103, Line 56: Claim 3, Delete "acety)phydrazinyl)methyl" and insert
-- acetyl)hydrazinyl)methyl --

Column 103, Line 64: Claim 3, Delete "acety)phydrazinyl)methyl" and insert
-- acetyl)hydrazinyl)methyl --

Signed and Sealed this
Twenty-first Day of March, 2017

Michelle K. Lee
*Director of the United States Patent and Trademark Office*